US007741278B2

(12) United States Patent
Rosenblum et al.

(10) Patent No.: US 7,741,278 B2
(45) Date of Patent: Jun. 22, 2010

(54) MODIFIED PROTEINS, DESIGNER TOXINS, AND METHODS OF MAKING THEREOF

(75) Inventors: Michael G. Rosenblum, Sugarland, TX (US); Lawrence Cheung, Houston, TX (US)

(73) Assignee: Research Development Foundation, Houston, TX (US)

(*) Notice: Subject to any disclaimer, the term of this patent is extended or adjusted under 35 U.S.C. 154(b) by 49 days.

(21) Appl. No.: 11/856,606

(22) Filed: Sep. 17, 2007

(65) Prior Publication Data

US 2008/0292544 A1 Nov. 27, 2008

Related U.S. Application Data

(62) Division of application No. 11/410,514, filed on Apr. 25, 2006, now Pat. No. 7,285,635, which is a division of application No. 10/074,596, filed on Feb. 12, 2002, now Pat. No. 7,083,957.

(60) Provisional application No. 60/268,402, filed on Feb. 12, 2001.

(51) Int. Cl.
*C07K 14/00* (2006.01)

(52) U.S. Cl. .......................................... 514/2; 530/350

(58) Field of Classification Search ....................... None
See application file for complete search history.

(56) References Cited

U.S. PATENT DOCUMENTS

| | | | | |
|---|---|---|---|---|
| 4,263,279 | A | 4/1981 | Sela et al. | 424/181.1 |
| 4,414,148 | A | 11/1983 | Jansen et al. | 530/391.9 |
| 4,522,918 | A | 6/1985 | Schlom et al. | 435/70.21 |
| 4,590,071 | A | 5/1986 | Scannon et al. | 424/183.1 |
| 4,650,674 | A | 3/1987 | Aggarwal et al. | 424/85.5 |
| 4,666,845 | A | 5/1987 | Mattes et al. | 435/7.23 |
| 4,671,958 | A | 6/1987 | Rodwell et al. | 424/1.53 |
| 4,677,064 | A | 6/1987 | Mark et al. | 435/69.1 |
| 4,753,894 | A | 6/1988 | Frankel et al. | 435/7.23 |
| 4,771,128 | A | 9/1988 | Ferris et al. | 530/391.7 |

(Continued)

FOREIGN PATENT DOCUMENTS

| | | |
|---|---|---|
| AU | B79527/87 | 4/1988 |

(Continued)

OTHER PUBLICATIONS

Aboud-Pirak et al., "Cytotoxic activity of daunorubicin or vindesine conjugated to a monoclonal antibody on cultured MCF-7 breast carcinoma cells," *Biochem. Pharmacol.*, 38:641-648, 1989.

(Continued)

*Primary Examiner*—Karen Cochrane Carlson
(74) *Attorney, Agent, or Firm*—Fulbright & Jaworski

(57) ABSTRACT

The present invention concerns methods of reducing the antigenicity of a proteinaceous compound while maintaining the compounds biological activity, as well as proteinaceous compositions with biological activity but reduced antigenicity. These methods and compositions have significant benefits to a subject in need of such compounds and compositions. Also included are modified toxin compounds that are truncated and/or possess reduce antigenicity. Such designer toxins have therapeutic, diagnostic, and preventative benefits, particularly as immunotoxins. Methods of treating cancer using these immunotoxins are provided.

44 Claims, 11 Drawing Sheets

U.S. PATENT DOCUMENTS

| | | | | |
|---|---|---|---|---|
| 4,801,578 | A | 1/1989 | Monsigny et al. | 424/279.1 |
| 4,831,122 | A | 5/1989 | Buchsbaum et al. | 530/391.3 |
| 4,863,726 | A | 9/1989 | Stevens et al. | 424/85.2 |
| 4,870,163 | A | 9/1989 | Rubin et al. | 530/413 |
| 4,888,415 | A | 12/1989 | Lambert et al. | 530/391.9 |
| 4,894,225 | A | 1/1990 | Zimmerman | 424/85.1 |
| 4,894,227 | A | 1/1990 | Stevens et al. | 424/85.2 |
| 4,894,443 | A | 1/1990 | Greenfield et al. | 424/179.1 |
| 4,935,233 | A | 6/1990 | Bell et al. | 424/85.5 |
| 4,946,778 | A | 8/1990 | Ladner et al. | 435/69.6 |
| 4,962,188 | A | 10/1990 | Frankel | 530/391.7 |
| 4,963,354 | A | 10/1990 | Shepard et al. | 424/85.1 |
| 4,971,792 | A | 11/1990 | Steplewski et al. | 424/1.49 |
| 4,980,457 | A | 12/1990 | Jansen et al. | 530/391.9 |
| 5,017,371 | A | 5/1991 | Cummins | 424/85.6 |
| 5,019,368 | A | 5/1991 | Epstein et al. | 424/1.49 |
| 5,032,521 | A | 7/1991 | White et al. | 530/388.85 |
| 5,134,075 | A | 7/1992 | Hellstrom et al. | 530/387.3 |
| 5,135,736 | A | 8/1992 | Anderson et al. | 424/1.49 |
| 5,359,046 | A | 10/1994 | Capon et al. | 536/23.4 |
| 5,621,083 | A | 4/1997 | Better et al. | 530/391.9 |
| 5,624,827 | A | 4/1997 | Rosenblum et al. | 435/91.5 |
| 5,631,348 | A | 5/1997 | Rosenblum et al. | 530/370 |
| 5,720,954 | A | 2/1998 | Hudziak et al. | 424/130.1 |
| 5,744,580 | A | 4/1998 | Better et al. | 530/377 |
| 5,770,195 | A | 6/1998 | Hudziak et al. | 424/130.1 |
| 5,830,880 | A | 11/1998 | Sedlacek et al. | 514/44 |
| 5,837,491 | A | 11/1998 | Better et al. | 435/69.1 |
| 5,851,815 | A | 12/1998 | Alnemri et al. | 435/219 |
| 5,851,829 | A | 12/1998 | Marasco et al. | 435/328 |
| 6,084,073 | A | 7/2000 | Piatak, Jr. | 530/370 |
| 6,099,842 | A | 8/2000 | Pastan et al. | 424/183.1 |
| 6,140,066 | A | 10/2000 | Lorberboum-Galski et al. | 435/7.23 |
| 6,197,528 | B1 | 3/2001 | Wu et al. | 435/7.2 |
| 6,214,974 | B1 | 4/2001 | Rosenblum et al. | 530/391.9 |
| 6,218,165 | B1 | 4/2001 | Estell et al. | 435/221 |
| 6,306,626 | B1 | 10/2001 | Rosenblum et al. | 435/70.21 |
| 6,309,873 | B1 | 10/2001 | Torrens Madrazo et al. | 435/216 |
| RE37,462 | E | 12/2001 | Rosenblum et al. | 503/370 |
| 6,531,133 | B1 | 3/2003 | Lorberboum-Galski et al. | 424/197.11 |
| 6,599,505 | B1 | 7/2003 | Rosenblum | 424/134.1 |
| 6,639,054 | B1 | 10/2003 | Alibhai et al. | 530/350 |
| 6,645,490 | B2 | 11/2003 | Yarkoni et al. | 424/178.1 |
| 6,669,938 | B1 | 12/2003 | Rosenblum et al. | 424/183.1 |
| 6,703,020 | B1 | 3/2004 | Thorpe et al. | 424/178.1 |
| 6,750,329 | B1 | 6/2004 | Rosenblum et al. | 530/391.7 |
| 7,083,957 | B2 | 8/2006 | Rosenblum et al. | 435/183 |
| 2002/0090374 | A1 | 7/2002 | Yarkoni et al. | 424/178.1 |
| 2003/0073163 | A1 | 4/2003 | Fernandez et al. | 435/69.1 |
| 2003/0086919 | A1 | 5/2003 | Rosenblum et al. | 424/94.63 |
| 2003/0134302 | A1 | 7/2003 | Fernandez et al. | 435/6 |
| 2003/0176331 | A1 | 9/2003 | Rosenblum et al. | 514/12 |
| 2003/0186384 | A1 | 10/2003 | Barth et al. | 435/69.5 |
| 2004/0009477 | A1 | 1/2004 | Fernandez et al. | 435/6 |
| 2004/0013691 | A1 | 1/2004 | Rosenblum | 424/234.1 |
| 2005/0100528 | A1 | 5/2005 | Rosenblum | 424/85.1 |
| 2005/0214307 | A1 | 9/2005 | Rosenblum | 424/178.1 |

FOREIGN PATENT DOCUMENTS

| | | |
|---|---|---|
| AU | B82047/87 | 6/1988 |
| AU | A13017/88 | 9/1988 |
| AU | A21725/88 | 3/1989 |
| AU | A30753/89 | 8/1989 |
| CA | 1339798 | 4/1998 |
| EP | 0118365 | 3/1984 |
| EP | 0160446 | 4/1985 |
| EP | 0150126 | 7/1985 |
| EP | 0184369 | 11/1985 |
| EP | 0226418 | 12/1986 |
| EP | 0222360 | 5/1987 |
| EP | 0256714 | 2/1988 |
| EP | 0281070 | 9/1988 |
| EP | 0305967 | 3/1989 |
| EP | 0336631 | 10/1989 |
| EP | 0350230 | 1/1990 |
| EP | 0396387 | 11/1990 |
| EP | 0893493 | 1/1999 |
| GB | 1564666 | 1/1978 |
| GB | 2148299 | 5/1985 |
| JP | 86121 | 7/1981 |
| JP | 62209098 | 12/1986 |
| JP | 190200 | 8/1987 |
| JP | 8-510642 | 11/1996 |
| WO | WO 85/00974 | 3/1985 |
| WO | WO 86/02945 | 5/1986 |
| WO | WO 86/05098 | 9/1986 |
| WO | WO 87/00056 | 1/1987 |
| WO | WO 88/09343 | 12/1988 |
| WO | WO 88/09344 | 12/1988 |
| WO | WO 89/00999 | 2/1989 |
| WO | WO 89/06692 | 7/1989 |
| WO | WO 90/00405 | 1/1990 |
| WO | WO 90/13649 | 11/1990 |
| WO | WO 91/16071 | 10/1991 |
| WO | WO 94/26910 | 11/1994 |
| WO | WO 97/22364 | 6/1997 |
| WO | WO 97/46259 | 12/1997 |
| WO | WO 98/37901 | 9/1998 |
| WO | WO 99/09206 | 2/1999 |
| WO | WO 99/29721 | 6/1999 |
| WO | WO 99/40198 | 8/1999 |
| WO | WO 99/43840 | 9/1999 |
| WO | WO 99/45128 | 9/1999 |
| WO | WO 99/49059 | 9/1999 |
| WO | WO 99/51620 | 10/1999 |
| WO | WO 99/51766 | 10/1999 |
| WO | WO 00/26406 | 5/2000 |
| WO | WO 00/34317 | 6/2000 |
| WO | WO 00/42179 | 7/2000 |
| WO | WO 02/42420 | 5/2002 |
| WO | WO 02/074979 | 9/2002 |
| WO | WO 03/002598 | 1/2003 |

OTHER PUBLICATIONS

Adams et al., "The Bcl-2 Protein Family: Arbiters of Cell Survival," *Science*, 281:1322-1326, 1998.

Aggarwal and Kohr, "Human tumor necrosis factor," *Methods in Enzymology*, 116:448-456, 1986.

Alfthan et al., "Properties of single-chain antibody containing different linker peptides," *Protein Engineering*, 8:725-731, 1995.

Alkan et al., "Antiviral and antiproliferative effects of interferons delivered via monoclonal antibodies," *J. Interferon Res.*, 4(3):355-363, 1984.

Alley et al., "Feasibility of drug screening with panels of human tumor cell lines using a microculture tetrazolium assay," *Cancer Res.*, 48:589-601, 1988.

Aqeilan et al., "Interleukin 2-Bax: a novel prototype of human chimeric proteins for targeted therapy," *FEBS Letters*, 457:271-276, 1999.

Ardekani et al., "Molecular profiling of cancer and drug-induced toxicity using new proteomic technologies," *Current Therapeutic Res.*, 62:803-819, 2001.

Arnon et al., "Monoclonal antibodies for immunotargeting of drugs in cancer therapy," Monoclonal Antibodies and Cancer Therapy, Alan R. Liss, Inc. pp. 243-256, 1985.

Arora, "Vascular endothelial growth facto chimeric toxin is highly active against endothelial cells," *Cancer Research*, 59:183-188, 1999.

Atkinson et al., "Conjugation of folate via gelonin carbohydrate residues retains ribosomal-activating properties of the toxin and permits targeting to folate receptor positive cells," *Biochem Molec. Biol.*, 276(30):27930-27935, 2001.

Barbieri and Stirpe, "Ribosome-inactivating proteins from plants: Properties and possible uses," *Cancer Surveys*, 1(3):489-520.

Batra et al., "Antitumor activity in mice of an immunotoxin made with anti-transferrin receptor and a recombinant form of Pseudomonas exotoxin," *Proc. Natl. Acad. Sci.*, 86:8545-8549, 1989.

Batra at al., "Single-chain immunotoxins directed at the human transferrin receptor containing Pseudomonas exotoxin A or diphtheria toxin: anti-TFR(Fv)-PE40 and DT388-anti-TFR(Fv)," *Mol. Cell. Biol.* 11:2200-2205, 1991.

Bendig, "Humanization of rodent monoclonal antibodies by CDR grafting," *Methods: A Companion to Methods in Enzymology*, 8:83-93, 1995.

Berkower, "The promise and pitfalls of monoclonal antibody therapeutics," *Current Opinion in Biotechnology*, 7:622-628, 1996.

Better et al., "Gelonin analogs with engineered cysteine residues form antibody immunoconjugates with unique properties," *J. Biological Chem.*, 269:9644-9650, 1994.

Bird et al., "Single-chain antigen-binding proteins," *Science*;242:423-426, 1988.

Bjorn et al., "Evaluation of monoclonal antibodies for the development of breast cancer immunotoxins," *Cancer Res.*, 45:1214-1221, 1985.

Blair et al., "Linkage of cytotoxic agents to immunoglobulins," *J. Immunol. Methods*, 59:129-143, 1983.

Blakey et al., "Antibody toxin conjugates: a perspective," *Monoclonal Antibody Therapy*. Waldmann (ed). 45:50-90, 1988.

Blick et al., "Phase I study of recombinant tumor necrosis factor in cancer patients," *Cancer Res.*, 47:2986-2989, 1987.

Blink et al., "Curtin Conference: Perforin-dependent nuclear targeting of granzymes: A central role in the nuclear events of granule-exocytosis-mediated apoptosis?," *Immunology and Cell Biology*, 77:206-215, 1999.

Bolognesi et al., "In vitro anti-tumour activity of anti-CD80 and anti-CD86 immunotoxins containing type 1 ribosome-inactivating proteins," *Br. J. Haematol.*, 110(2):351-361, 2000.

Bradford et al., "A rapid and sensitive method for the quantitation of microgram quantities of protein utilizing the principle of protein-dye binding," *Analy. Biochem.*, 72:248-252, 1976.

Bregman and Meyskens, "Human recombinant alpha- and gamma-interferons enhance the cytotoxic properties of tumor necrosis factor on human melanoma," *J. Biol. Response Mod.*, 7:384-389, 1988.

Brunet et al., "The inducible cytotoxic T-lymphocyte-associated gene transcript CTLA-1 sequence and gene localization to mouse chromosome 14," *Nature*, 322(6076):268-271, 1986.

Bumol et al., "Biosynthetic studies of proteoglycans in human melanoma cells with a monoclonal antibody to a core glycoprotein of chondroitin sulfate proteoglycans," *J. Biol. Chem.*, 259:12733-12741, 1984.

Chan et al., "Comparison of gallium-67 versus indium-111 monoclonal antibody (96.5, ZME-018) in detection of human melanoma in athymic mice," *J. Nucl. Med.*, 28:1441-1446, 1987.

Chaudhary et al., "A recombinant immunotoxin consisting of two antibody variable domains fused to Pseudomonas exotoxin," *Nature*, 339:394-397, 1989.

Collen et al., "Recombinant staphylokinase variants with altered immunoreactivity," *Circulation*, 94:197-206, 1996.

Cotton et al., "Somatic mutation and the origin of the antibody diversity. Clonal variability of the immunoglobulin produced by MOPC 21 cells in culture," *Eur. J. Immunol.*, 3:135-140, 1973.

Crosby et al., "A complex of serine protease gene expressed preferentially in cytotoxic T-lymphyocytes is closely linked to the T-cell receptor alpha- and delta-chain genes on mouse chromosome 14," *Genomics*, 6(2):252-259, 1990.

Dahl et al., "Isolation of a cDNA clone encoding a novel form of granzyme B from human NK cells and mapping to chromosome 14," *Hum. Genet.*, 84(5):465-470, 1990.

DeLand et al, "A perspective of monoclonal antibodies: past, present, and future," *Seminars in Nuc. Med.*, 19(3):158-165.

Dermer, "Another anniversary for the war on cancer," *Bio/technology*, 12:320, 1994.

Dillman, "Monoclonal antibodies for treating cancer," *Ann. Intern. Med.*, 111:592-603. 1989.

Dumontet, "[Immunotherapy and cancer: the role of monoclonal antibodies]," *J. Chir.* (Paris), 126:682-686, 1989.

Engert et al., "Resistance of myeloid leukaemia cell lines to ricin A-chain immunotoxins," *Leuk. Res.*, 15:1079-1086, 1991.

Falasca et al., "Properties of the ribosome-inactivating proteins gelonin, Momordica charantia inhibitor, and dianthins," *Biochem. J.*, 207:505-509, 1982.

Fiers et al. "Tumor necrosis factor: a potential anti tumor agent," *J. Interferon Res.*, 7:627-634, 1987.

Fitzgerald et al., "Why toxins!," *Seminars in Cancer Biology*, 7:87-95, 1996.

Flannery et al., "Immunomodulation: NK cells activated by interferon-conjugated monoclonal antibody against human osteosarcoma" *Eur. J. Cancer Clin. Oncol.*, 20:791-798, 1984.

Frankel et al., "Prospects for immunotoxin therapy in cancer," *Ann. Rev. Med.*, 37:125-142, 1986.

Freeman and Mayhew, "Targeted Drug Delivery," *Cancer*, 67:573-583, 1986.

Freshney, "Culture of animal cells, a manual of basic technique," Alan R. Liss, Inc, 1983.

Friedman et al., "BR96 sFv-PE40, a potent single-chain immunotoxin that selectively kills carcinoma cells," *Cancer Res.*, 53:334-339, 1993.

Frontiera et al., "Sequential use of indium-111 labeled monoclonal antibodies 96.5 and ZME-018 does not increase detection sensitivity for metastatic melanoma," *Clin. Nucl, Med.*, 14:357-366, 1989.

Gallego et al., "Preparation of four duanomycin-monoclonal antibody 791T/16 conjugates with anti-tumor activity," *Int. J. Cancer*, 33:737-744, 1984.

Gase et al., "Functional significance of NH2- and COOH- terminal regions of staphylokinase in plasminogen activation," *Thrombosis and Haemostasis*, 76(5):755-760, 1996.

GenBank Accession No. L12243.

Ghose and Blair, "The design of cytotoxic-agent-antibody conjugates," *Crit. Rev. Ther. Drug Carrier Syst.*, 3:263-359, 1987.

Giacomini et al., "Modulation by recombinant DNA leukocyte (alpha) and fibroblast (beta) interferons of the expression and shedding of HLA- and tumor-associated antigens by human melanoma cells," *J. Immunol.*, 133(3):1649-1655, 1984.

Gillies et al., "Antigen binding and biological activities of engineered mutant chimeric antibodies with human tumor specificities," *Hum. Antibodies Hybridomas.*, 1:47-54, 1990.

Gould et al., "Phase I study of an anti-breast cancer immunotoxin by continuous infusion: report of a targeted toxic effect not predicted by animal studies," *J. Natl. Cancer Inst.*, 81:775-781, 1989.

Green et al., "Monoclonal antibody therapy for solid tumors," *Cancer Treat Rev.*, 26:269-286, 2000.

Greiner et al., "Differential effects of recombinant human leukocyte interferons on cell surface antigen expression," *Cancer Res.*, 46:4984-4990, 1986.

Greiner et al., "Enhanced expression of surface tumor-associated antigens on human breast and colon tumor cells after recombinant human leukocyte alpha-interferon treatment," *Cancer Res.*, 44:3208-3214, 1984.

Haddad et al., "Structural organization of the hCTLA-1 gene encoding human granzyme B," *Gene*, 87(2):265-271, 1990.

Hamawy et al., "Activation of T lymphocytes for adhesion and cytokine expression by toxin-conjugated anti-CD3 monoclonal antibodies," *Transplantation*, 68:693-698, 1999.

Hamburger and Salmon, "Primary bioassay of human tumor stem cells," *Science*, 197:461-463, 1977.

Hann et al., "Building 'validated' mouse models of human cancer," *Curr. Opin. Cell Biol.*, 13:778-784, 2001.

Hanson et al., "A cluster of hematopoietic serine protease genes is found on the same chromosomal band as the human α/δ T-cell receptor locus," *Proc. Natl. Acad. Sci.*, USA, 87:960-963, 1990.

Harlow et al., *Antibodies: A laboratory Manuel*, Cold Spring Harbor Press, pp. 72-77, 92-97, 128-135, and 141-157, 1988.

Harper et al., "Proximity of the CTLA-1 serine esterase and Tcr alpha loci in mouse and man," *Immunogenetics*, 28(6):439-444, 1988.

Henkart, "Mechanism of Lymphocyte-mediated Cytotoxicity," *Ann. Rev. Immunol.*, 3:31-58, 1985.

Hertler et al., "A phase I study of T101-ricin A chain immunotoxin in refractory chronic lymphocytic leukemia," *J. Biol. Response Mod.*, 7:97-113, 1987.

Hoogenboom et al., "Targeting of tumor necrosis factor to tumor cells: secretion by myeloma cells of a genetically engineered antibody-tumor necrosis factor hybrid molecule," *Biochim Biophys Acta.*, 1096:345-354, 1991.

Huston et al., "Single-chain immunotechnology of Fv analogues and fusion proteins," in *Immunotechnology*, Gosling and Reen (eds), p. 47-60, 1993.

Imai et al, "[Current status of monoclonal antibodies to human melanoma and its application]," *Gan to Kagaku Ryoho.*, 10:852-860, 1983 (abstract in English).

Imai et al., "Differential effect of interferon on the expression of tumor-associated antigens and histocompatibility antigens on human melanoma cells: relationship to susceptibility to immune lysis mediated by monoclonal antibodies," *J. Immunol.*, 127(2):505-509, 1981.

Ivanov, "Therapeutic monoclonal antibodies in oncology," *Medicinal Immunol.*, 3:268, 2001.

Johnson et al., "Construction of an epitope vector utilising the diphtheria toxin B-subunit," *FEMS Microbiol. Lett.*, 146:91-96, 1997.

Johnson, "Review: Noncaspase proteases in apoptosis," *Leukemia*, 14:1695-1703, 2000.

Juhl et al., "New approaches in gastric cancer research: I. Monoclonal antibodies in diagnosis and therapy, " *Hepatogastroenterol.* 36:27-32, 1989.

Julius et al., "Induction of resting B cells to DNA synthesis by soluble monoclonal anti-immunoglobulin," *Eur. J. Immunol.*, 14:753-757, 1984.

Kagawa et al., "A binary adenoviral vector system for expressing high levels of the proapoptotic gene bax," *Gene Therapy*, 7:75-79, 2000.

Kagawa et al., "Antitumor Effect of Adenovirus-mediated Bax Gene Transfer on p53-sensitive and p53-resistant Cancer Lines," *Cancer Research*, 60:1157-1161, 2000.

Kam et al., "Review: Granzymes (lymphocyte serine proteases): characterization with natural and synthetic substrates and inhibitors," *Biochimica et Biophysica Acta*, 1477:307-323, 2000.

Kaneta et al., "Effect of gelonin immunoconjugate with monoclonal antibody MSN-1 to endometrial adenocarcinoma on antigen-producing tumor cells in vivo," *Jpn. J Cancer Res.*, 89(5):583-588, 1998.

Kim and Weaver, "Construction of a recombinant expression plasmid encoding a staphylococcal protein A-ricin A fusion protein," *Gene*; 68:315-321, 1988.

Kimmel et al., "In vitro drug sensitivity testing in human gliomas," *J. Neurosurg.* 66:161-171, 1987.

Kipriyanov et al., "Recombinant single-chain Fv fragments carrying c-terminal cysteine residues: production of bivalent and biotinylated miniantibodies," *Molecular Immunology*, 31:1047-1058, 1994.

Kirkwood et al., "Scintigraphic detection of metastatic melanoma using indium 111/DTPA conjugated anti-gp240 antibody (ZME-018)," *J. Clin. Oncol.*, 5:1247-1255, 1987.

Klein et al., "Genomic organization and chromosomal assignment for a serine protease gene (CSPB) expressed by human cytotoxic lymphocytes," *Genomics*, 5(1):110-117, 1989.

Koizumi et al., "Immunoscintigraphy and pharmacokinetics of indium-111-labeled ZME-018 monoclonal antibody in patients with malignant melanoma," *Japanese J of Cancer Res*, 79:973-981, 1988.

Kovarik et al., "Biochemical and histochemical characteristic of target antigen detected by monoclonal antibody HBCa-12 against a membrane component of human mammary carcinoma cell line," *Neoplasma*, 31(6):625-630, 1984.

Krizan et al., "Increased labeling of human melanoma cells in vitro using combinations of monoclonal antibodies recognizing separate cell surface antigenic determinants," *Cancer Res.*, 45:4904-4909, 1985.

Kudlicki et al., "Elongation and folding of nascent ricin chains as peptidy-rRNA on ribosomes: the effect of amino acid deletions on these processes," *J. Mol. Biol.*, 252:203-212, 1995.

Kufe et al., "Differential reactivity of a novel monoclonal antibody (DF3) with human malignant vs. benign breast tumors," *Hybridoma*, 3(3):223-232, 1984.

Kung et al., "A mouse IgM allotypic determinant (Igh-6.5) recognized by a monoclonal rat antibody," *J. Immunol.* 127:873-876, 1981.

Kurucz et al., "A bacterial expressed single-chain Fv construct from the 2B4 T-cell receptor," *Proc Natl Acad Sci* USA; 90: 3830-3834, 1993.

Lambert et al., "Immunotoxins containing single chain ribosome-inactivating proteins," in *Immunotoxins*, Frankel ed., p. 175-209, 1988.

Lambert et al., "Purified immunotoxins that are reactive with human lymphoid cells. Monoclonal antibodies conjugated to the ribosome-inactivating proteins gelonin and the pokeweed antiviral proteins," *J. Biol. Chem.*, 260(22):12035-12041, 1985.

Lazar et al., "Transforming growth factor alpha: mutation of aspartic acid 47 and leucine 48 results in different biological activities," *Mol. Cell. Biol.*, 8:1247-1252, 1988.

Leibovitz et al., "A hypo-osmotic medium to disaggregate tumor cell clumps into viable and clonogenic single cells for the human tumor stem cell clonogenic assay," *Int. J. Cell Cloning*, 1:478-485, 1983.

Levy et al., "Retroviral transfer and expression of a humanized, red-shifted green fluorescent protein gene into human tumor cells," *Nat. Biotechnol.*, 14:610-614, 1996.

Lewis and Crowe, "Generation of humanized monoclonal antibodies by 'best' fit framework selection and recombinant polymerase chain reaction," *Year Immunol.*, 7:110-118, 1993.

Lin et al., "Chromosomal localization of two human serine protease genes to region 14q11.2-q12 by in situ hybridization," *Cytogenet Cell Genet.*, 53(2-3):169-171, 1990.

Liu, "Mechanistic studies of a novel, human fusion toxin composed of vascular endothelial growth factor (VEGF)$_{121}$ and the serine protease granzyme B: Directed apoptotic events in vascular endothelial cells," *Molecular Cancer Therapeutics*, 2:949-959, 2003.

Lubin et al., "Analysis of the human factor VIII A2 inhibitor epitope by alanine scanning mutagenesis," *J. Biol. Chem.*, 272(48)30191-30195, 1997.

Macey et al., "Uptake of Indium-111-labeled monoclonal antibody ZME-018 as a function of tumor size in a patient with melanoma," *Am J of Physiologic Imaging*; 3:1-6, 1988.

Mazurier et al., "Rapid analysis and efficient selection of human transduced primitive hematopoietic cells using the humanized S65T green fluorescent protein," *Gene Ther.*, 5:556-562, 1998.

McCartney et al., "Engineering disulfide-linked singl-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides," *Protein Engineering*; 8:301-314, 1994.

McGraw et al., "Characterization of murine and humanized anti-CD33, gelonin immunotoxins reactive against myeloid leukemias," *Cancer Immunol. Immunother.*, 39:367-374, 1994.

Miescher-Granger et al., "Biological activities of human recombinant interferon alpha/beta targeted by anti-Epstein-Barr virus monoclonal antibodies," *FEBS Lett.*, 179:29-33, 1985.

Mihich, "Future perspectives for biological response modifiers: a viewpoint," *Sem Oncol.*, 13:234-254, 1986.

Montanaro et al., "A metalloproteinase associated with gelonin, a ribosome inactivating protein," *Ital. J. Biochem.*, p. 1-10, 1984.

Moola et al., "Erwinia chrysanthemi L-asparaginase: epitope mapping and production of antigenically modified enzymes," *Biochem J.*, 302( Pt 3):921-7, 1994.

Morris and Wool, "Determination by systematic deletion of the amino acids essential for catlysis by ricin A chain," *Proc. Natl. Acad. Sci. USA*, 89:4869-4873, 1992.

Motyka et al., "Mannose 6-phosphate/insulin-like growth factor II receptor is a death receptor for granzyme B during cytotoxic T cell-induced apoptosis," *Cell*, 103(3):491-500, 2000.

Mujoo et al., "Pharmacokinetics, tissue distribution, and in vivo antitumor effects of the antimelanoma immunotoxin ZME-gelonin," *Cancer Immunology, Immunotherapy*; 40:339-345, 1995.

Mujoo et al., "Pharmacology and therapeutic studies with ZME-gelonin immunotoxin," *Proc. Am Assoc. Cancer Res*, 32:266, #1580, 1991.

Muldoon et al., "Tracking and quantitation of retroviral-mediated transfer using a completely humanized, red-shifted green fluorescent protein gene," *Biotechniques*, 22:162-167, 1997.

Munishkin and Wool, "Systematic deletion analysis of ricin A-chain function," *J Biol. Chem.*, 270:30581-30587, 1995.

Murray et al., "Clinical parameters related to optimal tumor localization of indium-111-labeled mouse antimelanoma monoclonal antibody ZME-018" *J. Nuclear Med.*, 28:25-33,1987.

Murray et al., "Differential in vitro effects of alpha recombinant interferon and gamma recombinant interferon on the expression of melanoma-associated antigens and 240 Kd on melanoma cell line Ts294," *AACR*, 27:313, 1986.

Murray et al., "Differential in vitro effects of recombinant alpha-interferon and recombinant gamma-interferon alone or in combination on the expression of melanoma-associated surface antigens," *J. Biol. Response Modifiers*, 7:152-161, 1988.

Murray et al., "Radioimmunoimaging in Malignant Melanoma Patients With the Use of Indium-111-labeled Antimelanoma Monoclonal Antibody (ZME-018) to High-molecular-weight Antigen," *NCI Monogr.*, 3:3-9, 1987.

Nechushtan et al., "Conformation of the Bax C-terminus regulates subcellular location and cell death," *EMBO Journal*, 18:2330-2341, 1999.

Neville et al., "Monoclonal antibody-ricin or ricin A chain hybrids: kinetic analysis of cell killing for tumor therapy," *Immunol. Rev.*, 62:75-91, 1982.

Nolan et al., "Cloning and expression of a gene encoding gelonin, a ribosome-inactivating protein from Gelonium multiflorum," *Gene*, 134:223-227, 1993.

Nuti et al., "A monoclonal antibody (B72.3) defines patterns of distribution of a novel tumor-associated antigen in human mammary carcinoma cell populations," *Int. J. Cancer*, 29(5):539-546, 1982.

O'Boyle et al., "Potentiation of antiproliferative effects of monoclonal antibody IYm-1 and immunoconjugate Lym-1-gelonin on human Burkitt's lymphoma cells with γ-interferon and tumor necrosis factor," *Journal of Immunotherapy*, 18:221-230, 1995.

O'Hare et al., "Cytotoxicity of a recombinant ricin-A-chain fusion protein containg a proteolytically-cleavable spacer sequence," *FEBS Lett,*; 273:200-204, 1990.

Oldham et al., "Lymphokines, monoclonal antibodies, and other biological response modifiers in the treatment of cancer," *Cancer*, 54:2795-2806, 1984.

Owens and Young, "The genetic engineering of monclonal antibodies," *Journal of Immunological Methods*; 168:149-165, 1994.

Ozawa et al., "Selective killing of squamous carcinoma cells by an immunotoxin that recognizes the EGF receptor," *Int. J. Cancer*, 43:152-157, 1989.

Pagliaro et al., "Humanized M195 monoclonal antibody conjugated to recombinant gelonin: an anti-CD33 immunotoxin with antileukemic activity," *Clin. Cancer Res.*, 4(8):1971-1976, 1998.

Pai and Pastan "Immunotoxin therapy for cancer," *JAMA*, 269:78-81, 1993.

Panchagnula et al., "Monoclonal antibodies in drug targeting," *Journal of Clinical Pharmacy & Therapeutics*, 22:7-19, 1997.

Panchal, "Novel therapeutic strategies to selectively kill cancer cells," *Biochemical Pharmacology*, 55:247-252, 1998.

Parakh et al., *Proceedings of the American Association for Cancer Research Annual Meeting*, 36: 488, abstract #2909, 1995.

Pastan et al., "Recombinant toxins for cancer treatment," *Science*, 254:1173-1177, 1991.

Pearson et al., "Enhanced therapeutic efficacy against an ovarian tumor xenograft of immunotoxins used in conjunction with recombinant alpha-interferon," *Cancer Res.* 50:6379-6388, 1990.

Pelham et al., "Interferon-alpha conjugation to human osteogenic sarcoma monoclonal antibody 791T/36," *Cancer Immunol. Immunother.*, 15:210-216, 1983.

Peterson and Krohn, "Mapping of B cell epitopes on steroid 17 α-hydroxylase, and autoantigen in autoimmune polyglandular syndrome type I," *Clin. Exp. Immunol.*, 98:104-109, 1994.

Porter, "Human immune response to recombinant human proteins," *J. Pharmaceutical Sciences*, 90:1-11, 2001.

Pullyblank and Monson, "Monoclonal antibody treatment of colorectal cancer," *British Journal of Surgery*; 84:1511-1517, 1997.

Ramakrishnan and Houston, "Prevention of growth of leukemia cells in mice by monoclonal antibodies directed against Thy 1.1 antigen disulfide linked to two ribosomal inhibitors: pokeweed antiviral protein or ricin A chain," *Cancer Res.*, 44(4):1398-404, 1984.

Raso et al., "Monoclonal antibody-ricin a chain conjugate selectively cytotoxic for cells bearing the common acute lymphoblastic leukemia antigen." *Cancer Res.*, 42:457-464, 1982.

Reimann et al., "In vivo administration of lymphocyte-specific monoclonal antibodies in nonhuman primates. IV. Cytotoxic effect of an anti-T11-gelonin immunotoxin," *J. Clin. Invest.*, 82:129-138, 1988.

Rissoan et al., "Subtractive hybridization reveals the expression of immunoglobulinlike transcript 7, Eph-B1, granzyme B and 3 novel transcripts in human plasmacytoid dendiritic cells," *Blood*, 100(9):3295-3303, 2002.

Roscoe et al., "Primate antibody resposne to immunotoxin: serological and computer-aided analysis of epitopes on a truncated form of *pseudomonas* exotoxin" *Infection and Immunity*, 62:5055-5065, 1994.

Roselli et al., "Clinical value of radiolabeled monoclonal antibodies in the management of carcinoma patients," In Vivo, 7:615-622, 1993.

Rosenblum et al., "Comparative cytotoxicity and pharmacokinetics of antimelanoma immunotoxins containing either natural or recombinant gelonin," *Cancer Chemotherapy and Pharmacology*; 44:343-348, 1999.

Rosenblum et al., "A gelonin-containing immunotoxin directed against human breast carcinoma," *Mol. Biother.* 4:122-129, 1992.

Rosenblum et al., "A specific and potent immunotoxin composed of antibody ZME-018 and the plant toxin gelonin," *Molecular Biotherapy*; 3:6-13, 1991.

Rosenblum et al., "Amino acid sequence analysis, gene construction, cloning and expression of gelonin, a toxin derived from Gelonium multiflorum," *Journal of Interferon & Cytokine Research*, 15: 547-555, 1995.

Rosenblum et al., "An antimelanoma immunotoxin composed of antibody AMI-018 and the plant toxin gelonin," *Proc. Am. Assoc. Cancer Res. Annu. Meet.*, 29:427, #1700, 1988 (Abstract).

Rosenblum et al., "Antibody-mediated delivery of tumor necrosis factor (TNF-α)," *Proc. Am Cancer Res.*, 30:410, #1522, 1987.

Rosenblum et al., "Antibody-mediated delivery of tumor necrosis factor (TNF-alpha): improvement of cytotoxicity and reduction of cellular resistance," *Cancer Commun.* 3:21-27, 1991.

Rosenblum et al., "Cellular resistance to the antimelanoma immunotoxin ZME-gelonin and strategies to target resistant cells," *Cancer Immunol. Immunother.*, 42:115-121, 1996.

Rosenblum et al., "Growth inhibitory effects of interferon-beta but not interferon-alpha on human glioma cells: correlation of receptor binding, 2',5'-oligoadenylate synthetase and protein kinase activity," *Interferon Res.*, 10:141-151, 1990.

Rosenblum et al., "Monoclonal Antibodies for delivery of cytokines," *Cancer Bull*, 46(1):34-39, 1994.

Rosenblum et al., "Recombinant immunotoxins directed against the c-erb-2/HER2/neu oncogene product: in vitro cytotoxicity, pharmacokinetics, and in vivo efficacy studies in Xenograft models," *Clin Cancer Res*; 5:865-874, 1999.

Rosenblum et al., "Tumor necrosis factor a: multifaceted peptide hormone," *Critical Reviews in Immunology*, pp. 21-44, 1989.

Ross et al., "Increased toxicity of diphtheria toxin for human lymphoblastoid cells following covalent linkage to anti-(human lymphocyte) globulin or its F(ab')2 fragment," *Eur. J. Biochem.* 104:381-390, 1980.

Rowlinson-Busza et al., "Target delivery of biologic and other antineoplastic agents," *Current Opinion in Oncology*, 4:1142-1148, 1992.

Roy et al., "Anti-MY9-blocked-ricin: an immunotoxin for selective targeting of acute myeloid leukemia cells," *Blood*, 77:2404-2412, 1991.

Sairam et al., "Structural characterization of gelonin: evidence for separate antigenic and cytotoxic domains" *Biochemistry and Molecular Biology International*, 31:575-581, 1993.

Salmon and Liu "Effects of granulocyte-macrophage colony-stimulating factor on in vitro growth of human solid tumors," *J. Clin. Oncol.*, 7:1346-1350, 1989.

Salmon et al., "Evaluation of an automated image analysis system for counting human tumor colonies," *Internat. J. Cell Cloning*, 2:142-160, 1984.

Salmon et al., "Quantitation of differential sensativity of human-tumor stem cells to anticancer drugs," *New Eng. J. Med.*, 298:1321-1327, 1978.

Schienberg et al., "Monoclonal Antibody M195: A diagnostic marker for acute myelogenous leukemia," *Leukemia*, 3(6):440-445, 1989.

Scholz et al., "Correlation of drug response in patients and in the clonogenic assay with solid human tumour xenografts," *Eur. J. Cancer*, 26(8):901-905, 1990.

Schulz et al., "Monoclonal antibody-directed effector cells selectively lyse human melanoma cells in vitro and in vivo," *Proc. Natl. Acad. Sci. USA*, 80:5407-5411, 1983.

Scott et al., "An immunotoxin composed of a monoclonal antitransferrin receptor antibody linked by a disulfide bond to the ribosome-inactivating protein gelonin: potent in vitro and in vivo effects against human tumors," *J. Natl. Cancer Inst.*, 79:1163-1172, 1987.

Shoemaker et al, "Application of a human tumor colony-forming assay to new drug screening," *Cancer Res.*, 45:2145-2153, 1985.

Singh et al., "Hormonotoxins. Preparation and characterization of ovine luteinizing hormone-gelonin conjugate," *J. Biol. Chem.*, 264(6):3089-3095, 1989.

Sivam et al., "Immunotoxins to a human melanoma-associated antigen: comparison of gelonin with ricin and other a chain conjugates," *Cancer Res.*, 47:3169-3173, 1987.

Smyth and Trapani, "Granzymes: exogenous proteinases that induce target cell apoptosis," *Immunol. Today*, 16:202-206, 1995.

Smyth et al., "Granzymes: exogenous proteinases that induce target cell apoptosis," *Immunology Today*, 16(4):202-206, 1995.

Soule et al., "A human cell line from a pleural effusion derived from a breast carcinoma," *JNCI*, 51:1409-1416, 1973.

Soule et al., "Membrane 126-kilodalton phosphoglycoprotein associated with human carcinomas identified by a hybridoma antibody to mammary carcinoma cells," *Proc. Natl. Acad. Sci. USA*, 80:1332-1336, 1983.

Spitler et al., "Immunotoxin therapy of malignant melanoma," *Med Oncol Tumor Pharmacother.*, 3:147-152, 1986.

Spitler et al., "Therapy of metastatic malignant melanoma using XomaZyme Mel, a murine monoclonal anti-melanoma ricin A chain immunotoxin," *Nuc. Med. And Biol.s.*, 16:625-627, 1989.

Spitler et al., "Therapy of patients with malignant melanoma using a monoclonal antimelanoma antibody-ricin A chain immunotoxin," *Cancer Res.*, 47:1717-1723, 1987.

Stirpe et al., "Gelonin, a new inhibitor of protein synthesis, nontoxic to intact cells," *A Journal of Biological Chemistry*, 255:6947-6953, 1980.

Stremovskii et al., "Functional construction of anti-ferritin mini-antibody/ribonuclease," *Medicinal Immunol.*, 3:279, 2001.

Suhrbier et al., "Role of single amino acids in the recognition of a T cell epitope," *J. Immunol.*, 147:2507-2513, 1991.

Tai et al., "In Vivo Cytotoxicity of Ovarian Cancer Cells through Tumor-selective Expression of the BAX Gene," *Cancer Res.*, 59:2121-2126, 1999.

Tao et al., "Studies of aglycosylated chimeric mouse-human IgG. Role of carbohydrate in the structure and effector functions mediated by the human IgG constant region," *J Immunol.*, 143:2595-2601, 1989.

Tedder et al., "Epstein Ban virus binding induces internalization of the C3d receptor: a novel immunotoxin delivery system," *J. Immunol.* 137(4):1387-1391, 1986.

Thorpe et al., "An immunotoxin composed of monoclonal anti-thy 1.1 antibody and a ribosome-inactivating protein from saponaria oddicinalis: potent antitumor effects in vitro and in vivo," *J. Natl. Cancer Inst*, 75(1):151-159, 1985.

Thorpe et al., "Cytotoxicity acquired by conjugation of an anti-Thy1.1 monoclonal antibody and the ribosome-inactivating protein, gelonin," *Eur. J. Biochem.*, 116:447-454, 1981.

Thorpe et al., "Monoclonal antibodies: clinical and regulatory issues," *Trends Biotechnol.* 11:40-42, 1993.

Till et al., "An assay that predicts the ability of monoclonal antibodies to form potent ricin A chain-containing immunotoxins," *Cancer Res.* 48:1119-1123, 1988.

Trowbridge et al., "Anti-transferrin receptor monoclonal antibody and toxin-antibody conjugates affect growth of human tumour cells," *Nature*, 294:171-173, 1981.

Vitetta et al., "Neoplastic B cells as targets for antibody-ricin A chain immunotoxins," ., 62:15-183, 1982.

Vitetta et al., "Redesigning nature's poisons to create anti-tumor reagents," *Science*, 238:1098-1104, 1987.

Vogel et al., "In vivo studies with covalent conjugates of cobra venom factor and monoclonal antibodies to human tumors," *Hematology and Blood Transfusion*, 29:514-517, 1989.

Von Hoff, "Human tumor cloning assays: applications in clinical oncology and new antineoplastic agent development," *Cancer and Metastasis Reviews*, 7:357-371, 1988.

Wahl et al., "Experimental radioimmunotherapy," *Cancer*, 73:989-992, 1994.

Waldenamn, "Multichain interleukin-2 receptor: a target for immunotherapy in lymphoma," *J. Natl. Cancer Inst.* 81:914-923, 1989.

Waldmann at al., "Monoclonal antibodies in diagnosis and therapy," *Science,* 252:1657-1662, 1991.

Wels et al., "Diminution of antibodies directed against tumor cell surface epitopes: a single chain Fv fusion molecule specifically recognizes the extracellular domain of the c-erbB-2 receptor," *Journal of Steroid Biochemistry & Molecular Biology*, 43:1-7, 1992.

White et al., "Two monoclonal antibodies selective for human mammary carcinoma" *Cancer Res.*, 45:1337-1343, 1985.

Wild et al., "Inhibition of angiogenesis and tumour growth by VEGF121-toxin conjugate: differential effect on proliferating endothelial cells," *Br. J. Cancer*, 83:1077-1083, 2000.

Williams et al., "Targeting and therapy of human glioma xenografts in vivo utilizing radiolabeled antibodies," *Cancer Res*, 50:974s-979s, 1990.

Wilson et al, "Distribution and molecular characterization of a cell-surface and a cytoplasmic antigen detectable in human melanoma cells with monoclonal antibodies," *Int. J. Cancer*, 28:293-300, 1981.

Wool et al., "Structure and evolution of mammalian ribosomal proteins," *Biochem Cell Biol.*, 73:933-947, 1995.

Worn and Pluckthun, "Mutual stabilization of $V_L$ and $V_H$ in single-chain antibody fragments, investigated with mutants engineered for stability," *Biochemistry*; 37:13120-13127, 1998.

Xu et al., "Antileukemic activity of recombinant humanized M195-gelonin immunotoxin in nude mice," *Leukemia*, 10:321-326, 1996.

Yeung et al., "Trichosanthin, α-momorcharin and β-momorcharin: identity of aborifacient and ribosome-inactivating proteins," *Int. J. Pept. Protein Res.*, 31(3):265-8, 1988.

Yokota et al., "Synergistic potentiation of in vivo antitumor activity of anti-human T-leukemia immunotoxins by recombinant alpha-interferon and daunorubicin," *Cancer Res.*, 50:32-37, 1990.

Young, "Cell-Mediated Killing: A common Mechanism?" *Cell*, 46:641-642, 1986.

Yudina et al., "Study of interaction between anti-HER-2/NEU-mini-antibodies with SKOV-3 ovarian adenocarcinoma cells," *Medicinal Immunol.*, 3:285, 2001.

Yung et al., "In vitro chemosensitivity testing and its clinical application in human gliomas," *Neurosurg. Rev.*, 12:197-203, 1989.

Zuckerman et al., "Preparation and biological activity of recombinant leukocyte interferon A [rIFN alpha A] conjugated to an antimelanoma murine monoclonal antibody [ZME-018]," *Proc. Amer. Assoc. Cancer Res.*, 28:384, 1987.

Office Communication, issued in Japanese Patent Application No. 2003-513498, dated Jul. 1, 2008.

Desai et al., "Characterization of human anti-high molecular weight-melanoma-associated antigen single-chain Fv fragments isolated from a phage display antibody library," *Cancer Research*, 58:2417-2425, 1998.

Kang et al., "In vivo targeting of malignant melanoma by $^{125}$Iodine- and $^{99m}$Technetium-labeled single-chain Fv fragments against high molecular weight melanoma-associated antigen," *Clinical Cancer Research*, 6:4921-4931, 2000.

Wang et al., "Human single-chain Fv immunoconjugates targeted to a melanom-associated chondroitin sulfate proteoglycan mediate specific lysis of human melanoma cells by natural killer cells and complement," *Proc. Natl. Acad. Sci*, 96:1627-1632, 1999.

Office Communication, issued in Korean Patent Application No. 10-2008-7012188, dated Sep. 16, 2008. (English Translation).

GenBank Accession No. P33186, "Gelonium multiflorum," 1993.

Ashcroft et al., "Fullerene ($C_{60}$) immunoconjugates: interaction of water-soluble $C_{60}$ derivatives with the murine anti-gp240 melanoma antibody," *Chem. Commun.*, 3004-3006, 2004.

Azar et al., "GnRH-Bik/Bax/bak chimeric proteins target and kill adenocarcinoma cells; the general use of pro-apoptotic proteins of the Bcl-2 family as novel killing components of targeting chimeric proteins," *Apoptosis*, 5:531-542, 2000.

Canadian Office Action, issued in Canadian Patent Application No. 2,454,048, dated Apr. 17, 2008.

Ferrone and Kageshita, "Human high molecular weight-melanoma associated antigen as a target for active specific immunotherapy—a phase I clinical trial with murine antiidiotypic monoclonal antibodies," *J. Dermatol.*, 15:457-465, 1988.

Martin et al., "Retroviral vector targeting to melanoma cells by single-chain antibody incorporation in envelope," *Human Gene Therapy*, 9:737-746, 1998.

Office Communication issued in Australian Application No. 2002327310, mailed Apr. 28, 1996.

Oratz et al., "Antimelanoma monoclonal antibody-ricin A chain immunoconjugate (XMMME-001-RTA) plus cyclophosphamide in the treatment of metastatic malignant melanoma: results of a phase II trial," *J. Biol. Response Mod.*, 9:345-354, 1990.

Clarke et al., "Gene expression microarray analysis in cancer biology, pharmacology, and drug development: progress and potentialm," *Biochemical Pharmacology*, 62:1311-1336, 2001.

Fischer et al., "Difluoromethylornithine is effective as both a preventive and therapeutic agent against the development of UV carcinogenesis in SKH hairless mice," *Carcinogenesis*, 22(1):83-88, 2001.

Shoemaker et al., "Development of human tumor cell line panels for use in disease-oriented drug screening," In: *Prediction of Response Cancer Therapy*, 265-286, 1988.

Japanese Office Action, issued in Japanese Patent Application No. 2002-569065, dated Dec. 11, 2007.

Office Communication issued in Japanese Patent Application No. 2002-569065, dated Feb. 24, 2009.

Liu et al., "Targeted delivery of human pro-apoptotic enzymes to tumor cells: In vitro studies describing a novel class of recombinant highly cytotoxic agents," *Mol. Cancer Ther.*, 2:1341-1350, 2003.

Office Communication issued in Korean Patent Application No. 10-2003-7010616, dated Mar. 31, 2009.

Office Communication issued in Korean Patent Application No. 10-2008-7012188, dated Mar. 31, 2009.

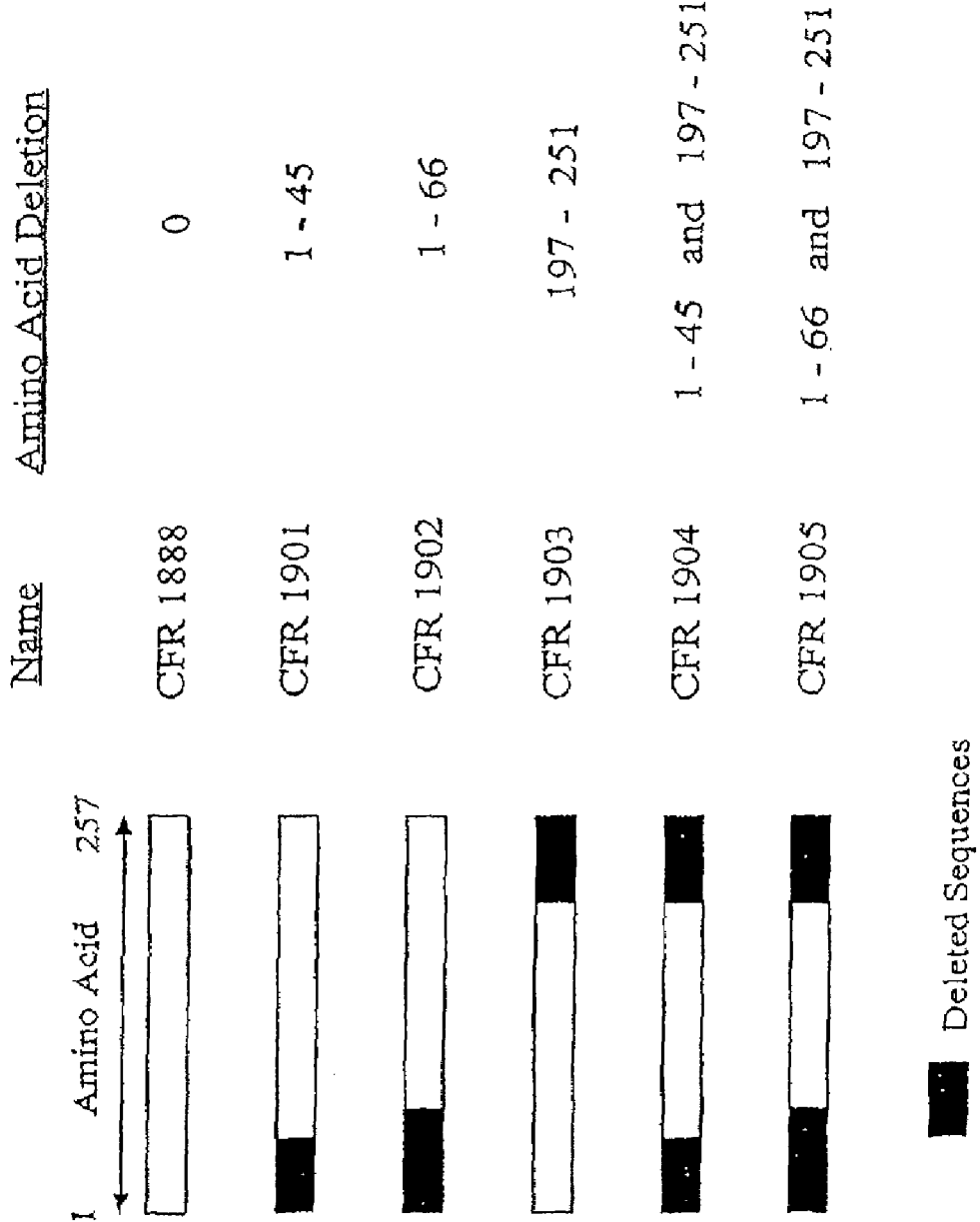

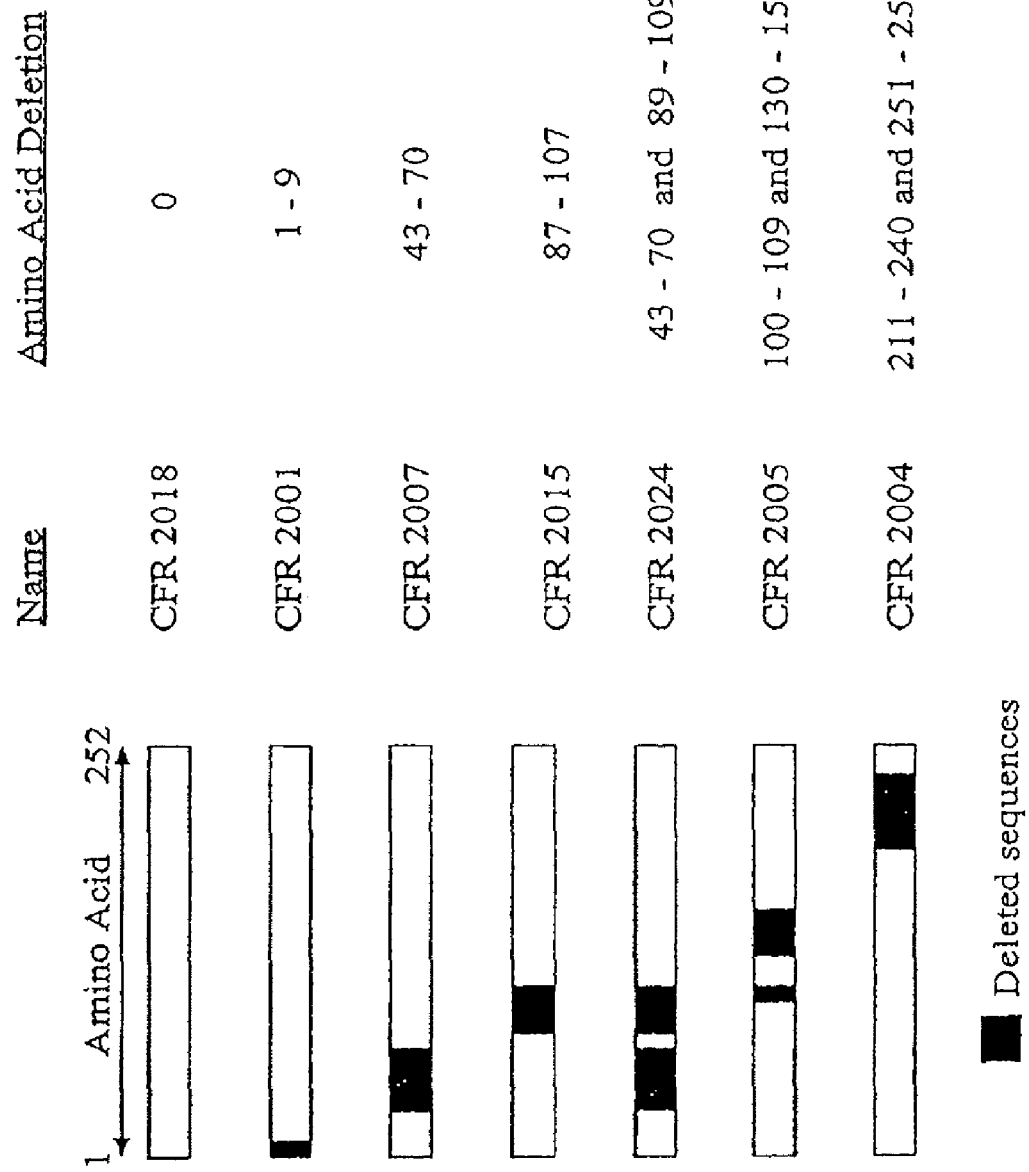

Construction of sFvMEL-Gel

FIG.4

```
SCFV-MEL→
ATG ACG GAC ATT GTG ATG ACC CAG TCT CAA AAA TTC ATG TCC ACA TCA GTA GGA  18
                                                        LCDR1
GAC AGG GTC AGC GTC ACC TGC AAG GCC AGT CAG AAT GTG GAT ACT AAT GTA GCC  36

TGG TAT CAA CAA AAA CCA GGG CAA TCT CCT GAA CCA CTG CTT TTC TCG GCA TCC  54
                                   LCDR2
TAC CGT TAC ACT GGA GTC CCT GAT CGC TTC ACA GGC AGT GGA TCT GGG ACA GAT  72

TTC ACT CTC ACC ATC AGC AAT GTG CAG TCT GAA GAC TTG GCA GAG TAT TTC TGT  90
                                                        LCDR3
CAG CAA TAT AAC AGC TAT CCT CTC ACG TTC GGT GGA GGC ACC AAG CTG GAG ATC 108
                                                 218 Linker
AAA GGC TCC ACC AGC GGC AGC GGT AAG CCA GGC TCC GGC GAA GGC AGC ACC AAA 126

GGC GAA GTG AAG GTT GAG GAG TCT GGA GGA GGC TTG GTG CAA CCT GGA GGA TCC 144
                                                           HCDR1
ATG AAA CTC TCC TGT GTT GTC TCT GGA TTC ACT TTC GGT AAT TAC TGG ATG AAC 162

TGG GTC CGC CAG TCT CCA GAG AAG GGG CTT GAG TGG ATT GCA GAA ATT AGA TTG 180
HCDR2
AAA TCC AAT AAT TTT GCA AGA TAT TAT GCG GAG TCT GTG AAA GGG AGG TTC ACC 198

ATC TCA AGA GAT GAT TCC AAA AGT AGT GTC TAC CTG CAA ATG ATC AAC CTA AGA 216
                                                                   HCDR3
GCT GAA GAT ACT GGC ATT TAT TAC TGT ACC AGT TAT GGT AAC TAC GTT GGG CAC 234

TAT TTT GAC CAC TGG GGC CAA GGC ACC ACT CTC ACC GTC TCC TCA GCT AGC GGT 252
G₄S Linker       Colonin→
CGC GGT GGC TCC GGT CTA GAC ACC GTG AGC TTT AGC ACT AAA GGT GCC ACT TAT 270

ATT ACC TAC GTG AAT TTC TTG AAT GAG CTA CGA GTT AAA TTG AAA CCC GAA GGT 288

AAC AGC CAT GGA ATC CCA TTG CTC GCA AAA AAA TGT GAT GAT CCT GGA AAG TGT 306

TTC GTT TTG GTA GCG CTT TCA AAT GAC AAT GGA CAG TTC GCG GAA ATA GCT ATA 324

GAT GTT ACA AGT GTT TAT GTG GTG GGC TAT CAA GTA AGA AAC AGA TCT TAC TTC 342

TTT AAA GAT GCT CCA GAT GCT GCT TAC GAA GGC CTC TTC AAA AAC ACA ATT AAA 360

ACA AGA CTT CAT TTT GGC GGC AGC TAT CCC TCG CTG GAA GGT GAG AAG GCA TAT 378

AGA GAG ACA ACA GAC TTG GCC ATT CAA CTA TTA AGC ATT GCC ATC AAG AAA CTT 396

GAT GAA AAT CCG ATA GAC AAT TAT AAA CCA ACG GAG ATA GCT AGT CTC TTA ATT 414

GTT GTT ATT CAA ATG GTG TCT GAA GCA GCT CGA TTC ACC TTT ATT GAG AAC CAA 432

ATT AGA AAT AAC TTT CAA CAG AGA ATT CGC CCG GCG AAT AAT ACA ATC AGC TTT 450

CAG AAT AAA TGG GGT AAA CTC TCG TTC CAG ATC CGG ACA TCA GGT GCA AAT GGA 468

ATG TTT TCG GAG GCA GTT GAA TTG GAA CGT GCA AAT GGC AAA AAA TAC TAT GTC 486

ACC GCA GTT GAT CAA GTA AAA CCC AAA ATA GCA CTC TTG AAG TTC GTC GAT AAA 504
                                                               End  *  *
GAT CCT AAA TAA TGA                                                    507
```

FIG. 5

SEQUENCE LISTING

<160> NUMBER OF SEQ ID NOS: 11

<210> SEQ ID NO 1
<211> LENGTH: 316
<212> TYPE: PRT
<213> ORGANISM: Gelonium multiflorum

<400> SEQUENCE: 1

```
Met Lys Gly Asn Met Lys Val Tyr Trp Ile Lys Ile Ala Val Ala Thr
 1               5                  10                  15

Trp Phe Cys Cys Thr Thr Ile Val Leu Gly Ser Thr Ala Arg Ile Phe
            20                  25                  30

Ser Leu Pro Thr Asn Asp Glu Glu Thr Ser Lys Thr Leu Gly Leu
        35                  40                  45

Asp Thr Val Ser Phe Ser Thr Lys Gly Ala Thr Tyr Ile Thr Tyr Val
    50                  55                  60

Asn Phe Leu Asn Glu Leu Arg Val Lys Leu Lys Pro Glu Gly Asn Ser
65                  70                  75                  80

His Gly Ile Pro Leu Leu Arg Lys Lys Cys Asp Asp Pro Gly Lys Cys
                85                  90                  95

Phe Val Leu Val Ala Leu Ser Asn Asp Asn Gly Gln Leu Ala Glu Ile
            100                 105                 110

Ala Ile Asp Val Thr Ser Val Tyr Val Val Gly Tyr Gln Val Arg Asn
        115                 120                 125

Arg Ser Tyr Phe Phe Lys Asp Ala Pro Asp Ala Ala Tyr Glu Gly Leu
    130                 135                 140

Phe Lys Asn Thr Ile Lys Thr Arg Leu His Phe Gly Gly Ser Tyr Pro
145                 150                 155                 160

Ser Leu Glu Gly Glu Lys Ala Tyr Arg Glu Thr Thr Asp Leu Gly Ile
                165                 170                 175

Glu Pro Leu Arg Ile Gly Ile Lys Lys Leu Asp Glu Asn Ala Ile Asp
            180                 185                 190

Asn Tyr Lys Pro Thr Glu Ile Ala Ser Ser Leu Leu Val Val Ile Gln
        195                 200                 205
```

```
Met Val Ser Glu Ala Ala Arg Phe Thr Phe Ile Glu Asn Gln Ile Arg
    210                 215                 220

Asn Asn Phe Gln Gln Arg Ile Arg Pro Ala Asn Asn Thr Ile Ser Leu
225                 230                 235                 240

Glu Asn Lys Trp Gly Lys Leu Ser Phe Gln Ile Arg Thr Ser Gly Ala
                245                 250                 255

Asn Gly Met Phe Ser Glu Ala Val Glu Leu Gly Arg Ala Asn Gly Lys
            260                 265                 270

Lys Tyr Tyr Val Thr Ala Val Asp Gln Val Lys Pro Lys Ile Ala Leu
        275                 280                 285

Leu Lys Phe Val Asp Lys Asp Pro Lys Thr Ser Leu Ala Ala Glu Leu
    290                 295                 300

Ile Ile Gln Asn Tyr Glu Ser Leu Val Gly Phe Asp
305                 310                 315
```

```
<210> SEQ ID NO 2
<211> LENGTH: 1176
<212> TYPE: DNA
<213> ORGANISM: Gelonium multiflorum

<400> SEQUENCE: 2
cagcttctca cttgtttggg ataatgaaag ggaacatgaa ggtgtactgg attaagattg      60
ctgtggcgac atggttttgc tgcactacta ttgtacttgg atcaacggcg aggattttct    120
ctcttcccac aaatgatgaa gaagaaacca gtaagacgct tggcctggac accgtgagct    180
ttagcactaa aggtgccact tatattacct acgtgaattt cttgaatgag ctacgagtta    240
aattgaaacc cgaaggtaac agccatggaa tcccattgct gcgcaaaaaa tgtgatgatc    300
ctggaaagtg tttcgttttg gtagcgcttt caaatgacaa tggacagttg gcggaaatag    360
ctatagatgt tacaagtgtt tatgtggtgg gctatcaagt aagaaacaga tcttacttct    420
ttaaagatgc tccagatgct gcttacgaag gcctcttcaa aaacacaatt aaaacaagac    480
ttcattttgg cggcagctat ccctcgctgg aaggtgagaa ggcatataga gagacaacag    540
acttgggcat tgaaccatta aggattggca tcaagaaact tgatgaaaat gcgatagaca    600
attataaacc aacggagata gctagttctc tattggttgt tattcaaatg gtgtctgaag    660
cagctcgatt caccttttatt gagaaccaaa ttagaaataa ctttcaacag agaattcgcc    720
cggcgaataa tacaatcagc cttgagaata atggggtaa actctcgttc cagatccgga    780
catcaggtgc aaatggaatg ttttcggagg cagttgaatt ggaacgtgca aatggcaaaa    840
aatactatgt caccgcagtt gatcaagtaa aacccaaaat agcactcttg aagttcgtcg    900
ataaagatcc taaaacgagc cttgctgctg aattgataat ccagaactat gagtcattag    960
tgggctttga ttagtacaac ttattgtgct ttttatatat tatagatatg atgccgggcc   1020
atgtattggc cttcgtagct taaataaagg catcgaatat tagcctcggt ggtgtatcta   1080
tcatgctgtg ttgtaaaact gccaatgttt atgttatcaa acagaaattg gcatgaagtt   1140
tctgtacaag tgttcaataa actgggctat acatgc                             1176
```

```
<210> SEQ ID NO 3
<211> LENGTH: 33
<212> TYPE: DNA
<213> ORGANISM: Homo sapiens

<400> SEQUENCE: 3
gctgcccaac cagccatggc ggacattgtg atg                                   33
```

<210> SEQ ID NO 4
<211> LENGTH: 50
<212> TYPE: DNA
<213> ORGANISM: Homo sapiens

<400> SEQUENCE: 4
gccggagcct ggcttgcacg ctgccgctgg tggagccttt gatcatccag            50

<210> SEQ ID NO 5
<211> LENGTH: 45
<212> TYPE: DNA
<213> ORGANISM: Homo sapiens

<400> SEQUENCE: 5
aagccaggct ccggcgaagg cagcaccaaa ggcgaagtga aggtt                 45

<210> SEQ ID NO 6
<211> LENGTH: 30
<212> TYPE: DNA
<213> ORGANISM: Homo sapiens

<400> SEQUENCE: 6
gccaccgcca ccactagttg aggagactgt                                  30

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ggcggtggct ccgtcatgac ggacattgtg atgacccagt ctcaaaaatt c          51

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggtggcggtg gctccggtct agacaccgtg acg                              33

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
aaggctcgtg tcgacctcga gtcattaagc tttaggatct ttatc                 45

<210> SEQ ID NO 10
<211> LENGTH: 1527
<212> TYPE: DNA
<213> ORGANISM: Artificial Sequence
<220> FEATURE:
<223> OTHER INFORMATION: Description of Artificial Sequence:  Synthetic
<220> FEATURE:
<221> NAME/KEY: CDS

<222> LOCATION: (1)..(1521)

<400> SEQUENCE: 10

| | | | | | | | | | | | | | | | | |
|---|---|---|---|---|---|---|---|---|---|---|---|---|---|---|---|---|
| atg | acg | gac | att | gtg | atg | acc | cag | tct | caa | aaa | ttc | atg | tcc | aca | tca | 48 |
| Met | Thr | Asp | Ile | Val | Met | Thr | Gln | Ser | Gln | Lys | Phe | Met | Ser | Thr | Ser | |
| 1 | | | | 5 | | | | | 10 | | | | | 15 | | |
| gta | gga | gac | agg | gtc | agc | gtc | acc | tgc | aag | gcc | agt | cag | aat | gtg | gat | 96 |
| Val | Gly | Asp | Arg | Val | Ser | Val | Thr | Cys | Lys | Ala | Ser | Gln | Asn | Val | Asp | |
| | | | 20 | | | | | 25 | | | | | 30 | | | |
| act | aat | gta | gcc | tgg | tat | caa | caa | aaa | cca | ggg | caa | tct | cct | gaa | cca | 144 |
| Thr | Asn | Val | Ala | Trp | Tyr | Gln | Gln | Lys | Pro | Gly | Gln | Ser | Pro | Glu | Pro | |
| | | 35 | | | | | 40 | | | | | 45 | | | | |
| ctg | ctt | ttc | tcg | gca | tcc | tac | cgt | tac | act | gga | gtc | cct | gat | cgc | ttc | 192 |
| Leu | Leu | Phe | Ser | Ala | Ser | Tyr | Arg | Tyr | Thr | Gly | Val | Pro | Asp | Arg | Phe | |
| | 50 | | | | | 55 | | | | | 60 | | | | | |
| aca | ggc | agt | gga | tct | ggg | aca | gat | ttc | act | ctc | acc | atc | agc | aat | gtg | 240 |
| Thr | Gly | Ser | Gly | Ser | Gly | Thr | Asp | Phe | Thr | Leu | Thr | Ile | Ser | Asn | Val | |
| 65 | | | | | 70 | | | | | 75 | | | | | 80 | |
| cag | tct | gaa | gac | ttg | gca | gag | tat | ttc | tgt | cag | caa | tat | aac | agc | tat | 288 |
| Gln | Ser | Glu | Asp | Leu | Ala | Glu | Tyr | Phe | Cys | Gln | Gln | Tyr | Asn | Ser | Tyr | |
| | | | 85 | | | | | 90 | | | | | 95 | | | |
| cct | ctg | acg | ttc | ggt | gga | ggc | acc | aag | ctg | gag | atc | aaa | ggc | tcc | acc | 336 |
| Pro | Leu | Thr | Phe | Gly | Gly | Gly | Thr | Lys | Leu | Glu | Ile | Lys | Gly | Ser | Thr | |
| | | 100 | | | | | 105 | | | | | 110 | | | | |
| agc | ggc | agc | ggt | aag | cca | ggt | ccc | ggc | gaa | ggc | agc | acc | aaa | ggc | gaa | 384 |
| Ser | Gly | Ser | Gly | Lys | Pro | Gly | Ser | Gly | Glu | Gly | Ser | Thr | Lys | Gly | Glu | |
| | 115 | | | | | 120 | | | | | 125 | | | | | |
| gtg | aag | gtt | gag | gag | tct | gga | gga | ggc | ttg | gtg | caa | cct | gga | gga | tcc | 432 |
| Val | Lys | Val | Glu | Glu | Ser | Gly | Gly | Gly | Leu | Val | Gln | Pro | Gly | Gly | Ser | |
| 130 | | | | | 135 | | | | | 140 | | | | | | |
| atg | aaa | ctc | tcc | tgt | gtt | gtc | tct | gga | ttc | act | ttc | ggt | aat | tac | tgg | 480 |
| Met | Lys | Leu | Ser | Cys | Val | Val | Ser | Gly | Phe | Thr | Phe | Gly | Asn | Tyr | Trp | |
| 145 | | | | 150 | | | | | 155 | | | | | 160 | | |
| atg | aac | tgg | gtc | cgc | cag | tct | cca | gag | aag | ggg | ctt | gag | tgg | att | gca | 528 |
| Met | Asn | Trp | Val | Arg | Gln | Ser | Pro | Glu | Lys | Gly | Leu | Glu | Trp | Ile | Ala | |
| | | | 165 | | | | | 170 | | | | | 175 | | | |
| gaa | att | aga | ttg | aaa | tcc | aat | aat | ttt | gca | aga | tat | tat | gcg | gag | tct | 576 |
| Glu | Ile | Arg | Leu | Lys | Ser | Asn | Asn | Phe | Ala | Arg | Tyr | Tyr | Ala | Glu | Ser | |
| | | 180 | | | | | 185 | | | | | 190 | | | | |
| gtg | aaa | ggg | agg | ttc | acc | atc | tca | aga | gat | gat | tcc | aaa | agt | agt | gtc | 624 |
| Val | Lys | Gly | Arg | Phe | Thr | Ile | Ser | Arg | Asp | Asp | Ser | Lys | Ser | Ser | Val | |
| | 195 | | | | | 200 | | | | | 205 | | | | | |
| tac | ctg | caa | atg | atc | aac | cta | aga | gct | gaa | gat | act | ggc | att | tat | tac | 672 |
| Tyr | Leu | Gln | Met | Ile | Asn | Leu | Arg | Ala | Glu | Asp | Thr | Gly | Ile | Tyr | Tyr | |
| 210 | | | | | 215 | | | | | 220 | | | | | | |
| tgt | acc | agt | tat | ggt | aac | tac | gtt | ggg | cac | tat | ttt | gac | cac | tgg | ggc | 720 |
| Cys | Thr | Ser | Tyr | Gly | Asn | Tyr | Val | Gly | His | Tyr | Phe | Asp | His | Trp | Gly | |
| 225 | | | | 230 | | | | | 235 | | | | | 240 | | |
| caa | ggc | acc | act | ctc | acc | gtc | tcc | tca | gct | agc | ggt | ggc | ggt | ggc | tcc | 768 |
| Gln | Gly | Thr | Thr | Leu | Thr | Val | Ser | Ser | Ala | Ser | Gly | Gly | Gly | Gly | Ser | |
| | | | 245 | | | | | 250 | | | | | 255 | | | |
| ggt | cta | gac | acc | gtg | agc | ttt | agc | act | aaa | ggt | gcc | act | tat | att | acc | 816 |
| Gly | Leu | Asp | Thr | Val | Ser | Phe | Ser | Thr | Lys | Gly | Ala | Thr | Tyr | Ile | Thr | |
| | | 260 | | | | | 265 | | | | | 270 | | | | |
| tac | gtg | aat | ttc | ttg | aat | gag | cta | cga | gtt | aaa | ttg | aaa | ccc | gaa | ggt | 864 |
| Tyr | Val | Asn | Phe | Leu | Asn | Glu | Leu | Arg | Val | Lys | Leu | Lys | Pro | Glu | Gly | |
| | 275 | | | | | 280 | | | | | 285 | | | | | |
| aac | agc | cat | gga | atc | cca | ttg | ctg | cgc | aaa | aaa | tgt | gat | gat | cct | gga | 912 |
| Asn | Ser | His | Gly | Ile | Pro | Leu | Leu | Arg | Lys | Lys | Cys | Asp | Asp | Pro | Gly | |
| 290 | | | | | 295 | | | | | 300 | | | | | | |

-continued

```
aag tgt ttc gtt ttg gta gcg ctt tca aat gac aat gga cag ttg gcg      960
Lys Cys Phe Val Leu Val Ala Leu Ser Asn Asp Asn Gly Gln Leu Ala
305                 310                 315                 320 gaa ata gct ata gat gtt aca agt gtt tat gtg gtg ggc tat caa gta     1008
Glu Ile Ala Ile Asp Val Thr Ser Val Tyr Val Val Gly Tyr Gln Val
            325                 330                 335 aga aac aga tct tac ttc ttt aaa gat gct cca gat gct gct tac gaa     1056
Arg Asn Arg Ser Tyr Phe Phe Lys Asp Ala Pro Asp Ala Ala Tyr Glu
        340                 345                 350 ggc ctc ttc aaa aac aca att aaa aca aga ctt cat ttt ggc ggc agc     1104
Gly Leu Phe Lys Asn Thr Ile Lys Thr Arg Leu His Phe Gly Gly Ser
    355                 360                 365 tat ccc tcg ctg gaa ggt gag aag gca tat aga gag aca aca gac ttg     1152
Tyr Pro Ser Leu Glu Gly Glu Lys Ala Tyr Arg Glu Thr Thr Asp Leu
370                 375                 380 ggc att gaa cca tta agg att ggc atc aag aaa ctt gat gaa aat gcg     1200
Gly Ile Glu Pro Leu Arg Ile Gly Ile Lys Lys Leu Asp Glu Asn Ala
385                 390                 395                 400 ata gac aat tat aaa cca acg gag ata gct agt tct cta ttg gtt gtt     1248
Ile Asp Asn Tyr Lys Pro Thr Glu Ile Ala Ser Ser Leu Leu Val Val
            405                 410                 415 att caa atg gtg tct gaa gca gct cga ttc acc ttt att gag aac caa     1296
Ile Gln Met Val Ser Glu Ala Ala Arg Phe Thr Phe Ile Glu Asn Gln
        420                 425                 430 att aga aat aac ttt caa cag aga att cgc ccg gcg aat aat aca atc     1344
Ile Arg Asn Asn Phe Gln Gln Arg Ile Arg Pro Ala Asn Asn Thr Ile
    435                 440                 445 agc ctt gag aat aaa tgg ggt aaa ctc tcg ttc cag atc cgg aca tca     1392
Ser Leu Glu Asn Lys Trp Gly Lys Leu Ser Phe Gln Ile Arg Thr Ser
450                 455                 460 ggt gca aat gga atg ttt tcg gag gca gtt gaa ttg gaa cgt gca aat     1440
Gly Ala Asn Gly Met Phe Ser Glu Ala Val Glu Leu Glu Arg Ala Asn
465                 470                 475                 480 ggc aaa aaa tac tat gtc acc gca gtt gat caa gta aaa ccc aaa ata     1488
Gly Lys Lys Tyr Tyr Val Thr Ala Val Asp Gln Val Lys Pro Lys Ile
            485                 490                 495 gca ctc ttg aag ttc gtc gat aaa gat cct aaa taatga                  1527
Ala Leu Leu Lys Phe Val Asp Lys Asp Pro Lys
        500                 505
```

<210> SEQ ID NO 11
<211> LENGTH: 507
<212> TYPE: PRT
<213> ORGANISM: Artificial Sequence
<223> OTHER INFORMATION: Description of Artificial Sequence: Synthetic

<400> SEQUENCE: 11

```
Met Thr Asp Ile Val Met Thr Gln Ser Gln Lys Phe Met Ser Thr Ser
1               5                   10                  15

Val Gly Asp Arg Val Ser Val Thr Cys Lys Ala Ser Gln Asn Val Asp
            20                  25                  30

Thr Asn Val Ala Trp Tyr Gln Gln Lys Pro Gly Gln Ser Pro Glu Pro
        35                  40                  45

Leu Leu Phe Ser Ala Ser Tyr Arg Tyr Thr Gly Val Pro Asp Arg Phe
    50                  55                  60

Thr Gly Ser Gly Ser Gly Thr Asp Phe Thr Leu Thr Ile Ser Asn Val
65                  70                  75                  80

Gln Ser Glu Asp Leu Ala Glu Tyr Phe Cys Gln Gln Tyr Asn Ser Tyr
                85                  90                  95
```

```
Pro Leu Thr Phe Gly Gly Gly Thr Lys Leu Glu Ile Lys Gly Ser Thr
            100                 105                 110

Ser Gly Ser Gly Lys Pro Gly Ser Gly Glu Gly Ser Thr Lys Gly Glu
            115                 120                 125

Val Lys Val Glu Glu Ser Gly Gly Gly Leu Val Gln Pro Gly Gly Ser
            130                 135                 140

Met Lys Leu Ser Cys Val Val Ser Gly Phe Thr Phe Gly Asn Tyr Trp
145                 150                 155                 160

Met Asn Trp Val Arg Gln Ser Pro Glu Lys Gly Leu Glu Trp Ile Ala
                165                 170                 175

Glu Ile Arg Leu Lys Ser Asn Asn Phe Ala Arg Tyr Tyr Ala Glu Ser
            180                 185                 190

Val Lys Gly Arg Phe Thr Ile Ser Arg Asp Asp Ser Lys Ser Ser Val
            195                 200                 205

Tyr Leu Gln Met Ile Asn Leu Arg Ala Glu Asp Thr Gly Ile Tyr Tyr
            210                 215                 220

Cys Thr Ser Tyr Gly Asn Tyr Val Gly His Tyr Phe Asp His Trp Gly
225                 230                 235                 240

Gln Gly Thr Thr Leu Thr Val Ser Ser Ala Ser Gly Gly Gly Gly Ser
                245                 250                 255

Gly Leu Asp Thr Val Ser Phe Ser Thr Lys Gly Ala Thr Tyr Ile Thr
            260                 265                 270

Tyr Val Asn Phe Leu Asn Glu Leu Arg Val Lys Leu Lys Pro Glu Gly
            275                 280                 285

Asn Ser His Gly Ile Pro Leu Leu Arg Lys Lys Cys Asp Asp Pro Gly
290                 295                 300

Lys Cys Phe Val Leu Val Ala Leu Ser Asn Asp Asn Gly Gln Leu Ala
305                 310                 315                 320

Glu Ile Ala Ile Asp Val Thr Ser Val Tyr Val Val Gly Tyr Gln Val
                325                 330                 335

Arg Asn Arg Ser Tyr Phe Phe Lys Asp Ala Pro Asp Ala Ala Tyr Glu
            340                 345                 350

Gly Leu Phe Lys Asn Thr Ile Lys Thr Arg Leu His Phe Gly Gly Ser
            355                 360                 365

Tyr Pro Ser Leu Glu Gly Glu Lys Ala Tyr Arg Glu Thr Thr Asp Leu
            370                 375                 380

Gly Ile Glu Pro Leu Arg Ile Gly Ile Lys Lys Leu Asp Glu Asn Ala
385                 390                 395                 400

Ile Asp Asn Tyr Lys Pro Thr Glu Ile Ala Ser Ser Leu Leu Val Val
                405                 410                 415

Ile Gln Met Val Ser Glu Ala Ala Arg Phe Thr Phe Ile Glu Asn Gln
            420                 425                 430

Ile Arg Asn Asn Phe Gln Gln Arg Ile Arg Pro Ala Asn Asn Thr Ile
            435                 440                 445

Ser Leu Glu Asn Lys Trp Gly Lys Leu Ser Phe Gln Ile Arg Thr Ser
450                 455                 460

Gly Ala Asn Gly Met Phe Ser Glu Ala Val Glu Leu Glu Arg Ala Asn
465                 470                 475                 480

Gly Lys Lys Tyr Tyr Val Thr Ala Val Asp Gln Val Lys Pro Lys Ile
                485                 490                 495

Ala Leu Leu Lys Phe Val Asp Lys Asp Pro Lys
            500                 505
```

MODIFIED PROTEINS, DESIGNER TOXINS, AND METHODS OF MAKING THEREOF

The present application is a divisional application of U.S. Ser. No. 11/410,514, filed Apr. 25, 2006, now U.S. Pat. No. 7,285,635 which was a divisional of U.S. Ser. No. 10/074,596 filed Feb. 12, 2002, now U.S. Pat. No. 7,083,957, which claims the benefit of priority to U.S. Provisional Patent Application No. 60/268,402, filed on Feb. 12, 2001, which are incorporated by reference in their entirety herein.

BACKGROUND OF THE INVENTION

1. Field of the Invention

The present invention relates generally to the fields of molecular biology and toxicology. More particularly, it concerns methods of generating modified proteins that are shorter and/or less antigenic polypeptides, as well as compositions comprising such polypeptides. Shorter and less antigenic versions of the plant toxin gelonin are described herein. Such modified proteins have therapeutic and diagnostic uses, for example, as immunotoxins.

2. Description of Related Art

Peptides, polypeptides, and proteins have numerous preventative, diagnostic, and therapeutic benefits. One disadvantage, however, is that such proteinaceous compounds may elicit an immune response to the compounds in the subject who hopes to receive their benefit. An immune response to the compounds can reduce, or altogether eliminate, the benefits that can be achieved through their use. Thus, it is a general desire to decrease the antigenicity or immunogenicity of a compound whose efficacy may be reduced by its eliciting an immune response in the host.

One specific type of protein, monoclonal antibodies, have been the focus of much research and development for preventative, diagnostic, and therapeutic benefits. Highly specific immunotoxins recognizing a variety of cell-surface antigens have been developed and tested over the last two decades. The attractive feature of immunotoxins is that these potent agents require very few molecules to be successfully delivered to the correct intracellular compartment in order to elicit a cytotoxic effect. Immunotoxins have been constructed containing various toxins such as saponin, abrin, ricin A chain (RTA), pseudomonas exotoxin (PE), diptheria toxin (DT), and gelonin.

Problems associated with the in vivo use of immunotoxins generally include: vascular damage leading to a capillary leak syndrome, mistargeting due to recognition of the toxin portion by the reticuloendothelial system, heterogeneity of target antigen expression, and development of anti-toxin antibodies leading to a narrowed therapy window of approximately 14 days. The development of anti-toxin and anti-conjugate antibodies may also prevent retreatment of patients despite evidence of antitumor effect. Prolonged use of immunotoxins in patients has provoked problems as well. Immunoconjugates containing RTA and PE have been found to be highly immunogenic in patients. In addition, the size of these proteins in immunotoxin constructs (approximately 30 kDa) is suspected to prevent effective penetration of immunoconjugates into solid tumors, The structural modification of Type I proteins such as RTA has, for the most part, been unsuccessful (Munishkin et al., 1995). Numerous RTA mutants modifying several amino acids have been generated. In 1995, Wool et al described 45 single amino acids deletions of RTA. Of those, only 8 single amino acid deletions were shown to have biological activity although the relative the relative biological activities of these deletion mutants compared to native RTA have not been examined. While interesting, the studies examining RTA are of limited value since, for example, RTA has only 30% sequence homology with other toxins such as gelonin.

Specific applications of monoclonal antibody (MAb)-based procedures have traditionally been found in the diagnosis and therapy of human cancers. However, clinical use of these agents has met with limited success due to drawbacks associated with this approach, e.g. heterogeneity of antigen expression, poor tumor penetration into solid tumors due in part to antibody size, and antigenicity of the antibodies (Roselli et al., 1993; Berkower, 1996; Pullybland et al., 1997; Panchagnula et al., 1997; Panchal, 1998). To circumvent these problems, a number of molecular approaches have been applied to reconfigure the conventional antibody structure into mouse:human chimeras, completely human antibodies or reshaped antibody fragments containing the antigen-binding portions of the original structure in a smaller and simpler (single-chain) format (Bird et al., 1988; Kipriyanov et al., 1994; Owens et al., 1994; McCartney et al., 1995; Worn et al, 1998). Single-chain antibodies (scfv, sfv), retaining the binding characteristics of the parent immunoglobulin (IgG), consist of the antibody $V_L$ and $V_H$ domains linked by a designed flexible peptide linker (Wels et al., 1992; Kurucz et al., 1993). Furthermore, scFvs may be preferred in clinical and diagnostic applications currently involving conventional MAbs or Fab fragments thereof, since their smaller size may allow better penetration of tumor tissue, improved pharmacokinetics, and a reduction in the immunogenicity observed with intravenously administered murine antibodies.

Among the few target antigens that are expressed at high levels in melanoma cells compared to normal tissue is the surface domain of a high molecular weight glycoprotein (gp240) found on a majority of melanoma cell lines and fresh tumor samples (Kantor et al., 1982). Two murine antibodies (designated 9.2.27 and ZME-018) recognizing different epitopes on this antigen have been previously isolated and described (Morgan et al., 1981; Wilson et al., 1981). The murine monoclonal antibody ZME-018 possesses high specificity for melanoma and is minimally reactive with a variety of normal tissues, making it a promising candidate for further study. Clinical trials examining the ability of this antibody to localize within melanoma lesions have demonstrated selective concentration in metastatic tumors (Macey et al., 1988; Koizumi et al., 1988).

Successful development of tumor-targeted therapeutic agents is dependent, in part, on the site-specific delivery of therapeutic agents and also on the biological activity of the delivered agent. Monoclonal antibodies have been employed to impart selectivity to otherwise indiscriminately cytotoxic agents such as toxins, radionuclides, and growth factors (Williams et al., 1990; Rowlinson-Busza et al., 1992; Wahl, 1994). One such molecule is gelonin, a 29-kDa ribosome-inactivating plant toxin with a potency and mechanism of action similar to ricin A-chain (RTA) but with improved stability and reduced toxicity (Stirpe et al., 1992; Rosenblum et al., 1995). Previous studies in our lab have identified and examined the biological properties of numerous chemical conjugates of the plant toxin gelonin and various antibodies (Boyle et al., 1995; Xu et al., 1996; Rosenblum et al., 1999). In previous studies, antibody ZME-018 was chemically coupled to purified gelonin, and this immunoconjugate demonstrated specific cytotoxicity against antigen-positive melanoma cells both in tissue culture and in human tumor xenograft models (Rosenblum et al., 1991; Mujoo et al., 1995). However, this construct, like immunotoxins generally, has inherent problems of antigenicity in human patients.

Given the side effects of immunotoxins and the limited progress made in reducing these problems, there is a continued need for the development of less antigenic proteins, polypeptides, and peptides for use in the treatment, prevention, and diagnosis of diseases and conditions. Replacement of antigenic sequences in the toxin molecule is a concept with respect to non-antibody polypeptides, such as toxins. While this concept has been used successfully with replacement of murine immunoglobulin framework domains with those of human immunoglobin framework domains creating a human/ mouse chimeric molecule, the same concept has never been successfully applied to other molecules particularly toxins or enzymes from plant sources, or by using the methods described herein.

SUMMARY OF THE INVENTION

The present invention concerns methods of creating and preparing proteinaceous compounds that are modified to form a modified protein that possesses an advantage over a non-modified or native protein. The present invention also includes compositions that are generated from these methods.

In some embodiments of the invention, a recombinant gelonin toxin is provided that is altered with respect to the native gelonin sequence. The recombinant gelonin toxin may have amino acids replaced or removed as compared to the native gelonin protein sequence (shown in SEQ ID NO:1), which is disclosed in U.S. Pat. No. 5,631,348, which is herein incorporated by reference and which is provided by GenBank accession number L12243. The recombinant gelonin toxin or the present invention does not have all of the amino acids of SEQ ID NO:1, but in some embodiments, comprises a core toxin region defined as amino acid residues 110-210 of SEQ ID NO:1. Other compounds of the present invention include a recombinant gelonin toxin that contains the core toxin region in addition to having at least 10, 20, 30, 40, 50, 60, 70, 80, 90, 100 or more contiguous amino acid residues of SEQ ID NO: 1 in addition to the core toxin region. It is contemplated that compounds of the present invention also include multiple regions that include contiguous amino acid residues of SEQ ID NO:1. For example, a compound may include the core toxin region in addition to 10 contiguous amino acid residues of SEQ ID NO:1 before the core toxin region and 20 contiguous amino acid residues of SEQ ID NO:1 after the core toxin region.

A recombinant gelonin toxin of the invention also includes a gelonin toxin that is truncated with respect to the native sequence, such that the toxin is lacking at least 5, 10, 20, 30, 40, 50, or more amino acids of SEQ ID NO:1. In some embodiments of the invention, the toxin contains the core toxin region, but is missing amino acids anywhere outside the core toxin region. In addition to deletions, the recombinant gelonin toxin of the invention may have an amino acid in place of a removed amino acid. For example, the glycine residue at position 7 in the gelonin protein sequence may be replaced with a non-glycine amino acid residue or a modified amino acid. If the glycine residue at position 7 is merely removed, the alanine at position 8 in SEQ ID NO:1 becomes position 7, but is not considered a replacement because the positions of the amino acids are simply shifted by 1 position. It is contemplated that at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more amino acids may be replaced.

In further embodiments of the present invention, a recombinant gelonin toxin may be attached to a second polypeptide. In some instances, the second polypeptide serves to target the gelonin toxin to a particular cell type (including cells having a particular genotype or phenotype, such as a cancer cell or a cell infected with a pathogen), part of the body, or other specific location. Proteinaceous compounds of the invention, therefore, include a compound that contains both a recombinant gelonin toxin, such as a modified gelonin toxin and a second polypeptide. In some embodiments, the two polypeptides are conjugated to one another, while in other embodiments the polypeptides are engineered recombinantly to produce a fusion protein. Conjugated compounds may be attached to one another by a linker. It is contemplated that modified proteins of the present invention may include additional polypeptide compositions, all or some of which may be covalently linked to one another.

The present invention concerns multipolypeptide compositions in which more than one polypeptide entity is presented as a single compound. Thus, a modified protein may be attached to a second, third, fourth, fifth, sixth or more polypeptides. Alternatively, two or more modified proteins may be presented as a singly proteinaceous compound. In some embodiments of the invention, the second polypeptide is an antibody, such as an antibody with an antigen binding region. It is contemplated that an antibody may be directed against a tumor antigen, an oncogene product, a cellular receptor, or any other compound that localizes the multipolypeptide composition. As disclosed herein, the second polypeptide may be an enzyme, a cytokine, a cytotoxic molecule, a growth factor, a ligand or receptor, or any molecule that is capable of modifying cell growth characteristics.

Other compositions of the invention include a modified enzyme produced by a process that includes: a) identifying one or more antigenic regions in the enzyme using an antibody; b) removing one or more antigenic regions from the enzyme to form a modified enzyme; and c) determining that the modified enzyme has enzymatic activity. An enzyme is a biological entity that catalyzes a specific chemical reaction in a cell; it may be a protein or a nucleic acid molecule. However, it is contemplated that any methods discussed with respect to enzymes may be applied to polypeptides generally. An antigenic region is a region of a polypeptide that is specifically recognized by an antibody or T-cell receptor of a particular organism. It is understood that a region may be antigenic in one species but not in another species, and therefore, antigenicity of a compound is a characteristic that is relative to a particular organism. In addition to removing amino acids that are part of an antigenic region, it is contemplated that amino acids from more than one antigenic region may be removed from an enzyme of the present invention. Amino acids from all or part of 1, 2, 3, 4, 5, 6, 7, 8, 9, 10, 11, 12, 13, 14, 15, 16, 17, 18, 19, 20, or more antigenic regions may be removed from the polypeptide. In some cases, the removed region is replaced with a region that is less antigenic than the removed region. Of course, it is understood that amino acids flanking an antigenic region may also be removed, for example, for purposes of convenience. Thus, 1, 2, 3, 4, 5, 6, 7, 8, 9, 10, 11, 12, 13, 14, 15, 16, 17, 18, 19, 20, or more amino acids flanking one or both sides of an antigenic region may be removed or replaced.

A less antigenic region or regions may be identified by searching a protein database search for regions that are homologous to or have some residues in common with an antigenic region. An antigenic region may be identified, and this sequence is used to identify known protein sequences of the organism in which less antigenicity with respect to a modified protein is desirable. Thus, a human protein database may be employed to find human protein sequences that have multiple residues that are identical or comparable to residues of an antigenic region of protein desired to be less antigenic in humans. A residue is comparable to another residue if they are not identical but they share similar chemical properties. Such relationships are well known to those of skill in the art.

In some embodiments, an antibody is employed to identify an antigenic region. It is contemplated that an antibody may be polyclonal. The organism source of the antibody is the same species of organism in which the modified protein is desired to be less antigenic. Therefore, if an enzyme or protein is desired to be less antigenic in a human, it is desirable in some embodiments that human antibodies be used either to identify an antigenic region or to determine whether a modified protein is less antigenic than a non-modified protein (native or recombinant full-length). In preferred embodiments, a modified enzyme or protein is evaluated for reduced or lower antigenicity by comparing the antigenicity of a modified enzyme or protein with an unmodified enzyme or protein; this can be accomplished by i) obtaining a sample from a subject prior to exposure to or administration of a modified protein and using the sample to compare the antigenicity of the modified protein and the unmodified version of the same protein, or ii) obtaining a sample from a subject after exposure to or administration of a modified protein and using the sample to compare the antigenicity of the modified protein and the unmodified version of the same protein. A sample may be any composition that contains antibodies or immune cells, including bodily fluids such as blood (serum). The sample may then be used to implement an immunodetection method, such as an ELISA. It is contemplated that the subject may be naive with respect to the unmodified protein, though it is preferable that a subject providing the sample have been previously exposed to the unmodified protein. In some embodiments it may be appropriate that a sample is culture media from a monoclonal antibody hybridoma.

While in other aspects of the invention, determining whether modified protein or enzyme possesses activity may be accomplished by assaying the modified compound for activity, such as enzymatic activity.

Any enzyme may be modified according to methods of the present invention. The enzyme may be a hydrolase (e.g., deaminase, esterase, glycosidase, lipase, nuclease, peptidase, phosphatase, phosphodiesterase, and proteinase); isomerase (e.g., epimerase, mutase, and racemase); ligase or synthetase (e.g., acyl-CoA synthetase, amino-acyl-tRNA synthetase, and carboxylase); lyase (e.g., aldolase, decarboxylase, dehydratase, and nucleotide cyclase); oxidoreductase (e.g., dehydrogenase, dioxygenase, hydrogenase, monooxygenase, nitrogenase, oxidase, and reductase); and transferase (e.g., acyltransferase, aminotransferase, glycosyltransferase, kinase, methyltransferase, nucleotidyltransferase, phosphorylase, and sulphotransferase). In specific embodiments, the enzyme is classified as a toxin, which means it is toxic to a cell, tissue, or organism. Specifically contemplated as part of the invention are toxins produced by plants, such as gelonin. As previously discussed a modified enzyme, like modified gelonin polypeptides of the invention, may be attached to additional polypeptides. It is understood that any of the embodiments with respect to modified gelonin may be applied to modified enzymes, and vice versa.

The present invention also concerns methods of generating modified proteins that have reduced antigenicity, and in some cases, particularly with respect to a subject. In some embodiments, the method includes: a) selecting a protein one desires to administer to a first subject; b) identifying a region of the protein that is antigenic in the first subject using antiserum from either the first subject or a second subject of the same species as the first subject; c) generating a modified protein in which the identified region is absent; and d) confirming the modified protein has reduced antigenicity. As previously discussed, this last step may be accomplished using a sample, such as serum, from an individual who has been previously exposed to the unmodified version of the modified protein or from the individual in which a reduced immune response against the modified protein is desired.

It is further contemplated that methods of generating a modified protein include steps of screening a human protein database to identify a less antigenic region that has homology to the antigenic region of the protein and replacing the antigenic region with all or part of the identified region that is less antigenic to form a modified protein. Screening of a large human protein database is not required but is desirable. Thus, if the sequence of a particular human protein that has homology or identical residues with an antigenic region is known independently from screening a human protein database, this method would be included in the scope of the present invention. For example, one may know the sequence of the human homolog of a mouse enzyme whose reduced antigenicity is desired; replacing regions in the mouse protein with residues from the human sequence concerns the present invention. Methods and compositions of the invention involve replacing, deleting, and/or modifying amino acid residues of a polypeptide. A residue that is replaced renders both the order and number of the remaining amino acids the same as the polypeptide before the residue was replaced. A residue may be replaced with a conservative or non-conservative residue. A residue that is deleted does not disturb the order of the remaining amino acids, but reduces the number of residues of the polypeptide by one. A residue that is modified is one that is chemically altered; this change does not alter the order or number of remaining amino acids in the polypeptide.

In some embodiments, methods involve using recombinant nucleic acid technology to achieve a modified protein or enzyme. Thus, a cDNA sequence for enzyme desired to be modified may be manipulated such that a nucleic acid sequence that encodes an antigenic region is replaced with a nucleic acid sequence that encodes a less antigenic region. Alternatively, a modified protein may be generated by removing the identified region. A region that is removed is considered absent. An absent region may contain at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more amino acid residues. Moreover, a modified protein may have more than one antigenic region removed or replaced, and amino acids flanking the region may also be removed or replaced. It is contemplated that the absent antigenic region may be replaced with the same number of amino acid residues that are removed.

In the methods of the present invention, an antigenic region may be identified or a modified protein may be evaluated using an ELISA assay. A subject may be a mammal, such as a human.

Other compositions of the invention include a humanized recombinant gelonin toxin having at least 3 amino acids from one or more of antigenic domains 1, 2, 3, or 4 replaced with amino acids less antigenic in a human than a recombinant gelonin toxin with the replaced amino acids. Antigenic domains of a gelonin toxin are described elsewhere. It is contemplated that at least 1, 2, 3, 4, 5, 6, 7, 8, 9, 10, 11, 12, 13, 14, 15, 16, 17, 18, 19, 20, 25, 30, 35, 40, 45, 50, 75, 100, or more amino acids from antigenic domains 1, 2, 3, and/or 4 are replaced, deleted, or modified. Amino acids from at least 2, 3, or 4 antigenic domains may be manipulated.

Additional embodiments of the invention provide a recombinant gelonin toxin produced by a process involving: a)

identifying at least one region in a gelonin toxin that is antigenic in a mammal; and b) replacing at least a portion of the antigenic region with a region less antigenic in the mammal. It is contemplated that gelonin toxin may be recombinant, that is, derived from a nucleic acid sequence that has been manipulated in vitro. The process may also include comparing the identified antigenic region with mammalian amino acid sequences, whereby a region less antigenic in the mammal is identified or identifying a region that is less antigenic in the mammal. In some embodiments, the mammal is a human. As previously mentioned, any of the methods and compositions disclosed herein may be applied to any other methods and compositions described herein.

The present invention also concerns methods of treatment using the compositions of the invention. They may used in the treatment of any disease in which treatment takes the form of killing or eliminating certain cells or organisms, which is effected by toxins of the invention. It is contemplated that embodiments discussed with respect to one composition or method may be applied to any other composition or method of the invention.

In some embodiments, there is a method of killing cancer or tumor cells by providing to the cells an effective amount of an immunotoxin that includes all or part of a gelonin toxin, such as its core toxin region, and all or part of an antibody, which is employed to direct the immunotoxin to a particular cell. An "effective amount" refers to an amount that achieves the intended goal. In the case of a method for killing a cancer or tumor cell, it is the amount to achieve the killing of a cancer or tumor cell. Other methods of the invention include methods for treating cancer in a patient by administering to the patient an effective amount of a composition comprising an immunotoxin comprising a core toxin region of gelonin and single chain antibody that specifically targets a cancer cell. An "effective amount" with respect to treatment refers to conferring a therapeutic benefit on the subject. The term "therapeutic benefit" used throughout this application refers to anything that promotes or enhances the well-being of the subject with respect to the medical treatment of his condition. In the context of cancer (though it may apply to other conditions as well), therapeutic benefit, which includes treatment of pre-cancer, cancer, and hyperproliferative diseases, includes the following nonexhaustive examples: extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition.

In some embodiments of the invention the toxin is gelonin. In still further embodiments, the immunotoxin includes all or part of the amino acid sequence of SEQ ID NO:1. It is contemplated that the immunotoxin may include fewer amino acids than the full-length gelonin protein sequence, though it includes the full-length sequence in some embodiments. It is further contemplated that the toxin may be humanized and it may be any of the toxins or constructs disclosed or described herein.

In further embodiments the antibody of the immunotoxin is humanized and/or is a single chain antibody. In methods of the invention, an antibody targets the immunotoxin to the targeted cancer cell, though it may not be full-length, so long as it allows for specific targeting. In some embodiments, the antibody (which includes antibody fragments) specifically targets (i.e., binds) an antigen on the surface of the targeted cell. In more specific embodiments, the antibody targets a tumor antigen. The antibody can be any mammalian antibody, though it is specifically contemplated that the antibody is a mouse, rabbit, rat, goat, or monkey antibody. The antibody, though from a different species, may be humanized according to the invention or other methods known to those of ordinary skill in the art. In cases in which the antibody is a single chain antibody, it may include 9.2.27 or ZME-018, which are antibodies directed to melanoma cells. In specific examples, the immunotoxin is scfvMEL-2018 (SEQ ID NO: 11) or scfvMEL-2025, described herein.

The cancer cell that is targeted may be a cell from prostate, lung, brain, skin, liver, breast, lymphoid, stomach, testicular, ovarian, pancreas, bone, bone marrow, head and neck, cervical, esophagus, eye, gall bladder, kidney, adrenal glands, heart, colon, or blood. Alternatively, the cancer patient may have a cancer in or from the organs/tissue identified above. In some embodiments of the invention, the cancer cell is a melanoma cell. It is contemplated that the cancer or tumor cell may be in a patient. In some embodiments, the patient will be administered an effective amount of a therapeutic composition, which refers to the amount needed to achieve a particular desired result, such as treatment. In the context of cancer, for example, the desired result may be killing of a cancer or tumor cell.

The immunotoxin may be included in a pharmaceutically or pharmacologically acceptable composition. As part of a treatment regimen, a patient may also receive other anti-cancer therapy, such as chemotherapy, radiotherapy, gene therapy, surgery, or other immunotherapy.

In even further embodiments, it is contemplated that the immunotoxin may be provided to a cell or a patient by providing an expression construct that contains a nucleic acid sequence encoding the immunotoxin and is capable of expressing the immunotoxin. In some embodiments, the expression construct is a viral vector, including, but not limited to, an adenovirus vector, an adeno-associated virus vector, a hepatitis virus, a herpesvirus, a lentivirus, a retrovirus, or a vaccinia virus.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A-3B. Gelonin Deletion Constructs. The structures of gelonin deletion constructs are shown.

FIG. 4. Schematic of PCR-based construction of the sfvMEL/rGel fusion toxin and ligation into pET-32a derived vectors.

FIG. 5 Complete DNA sequence analysis of the sfvMEL/rGel fusion construct (SEQ ID NO:10).

DESCRIPTION OF ILLUSTRATIVE EMBODIMENTS

Figure 1:
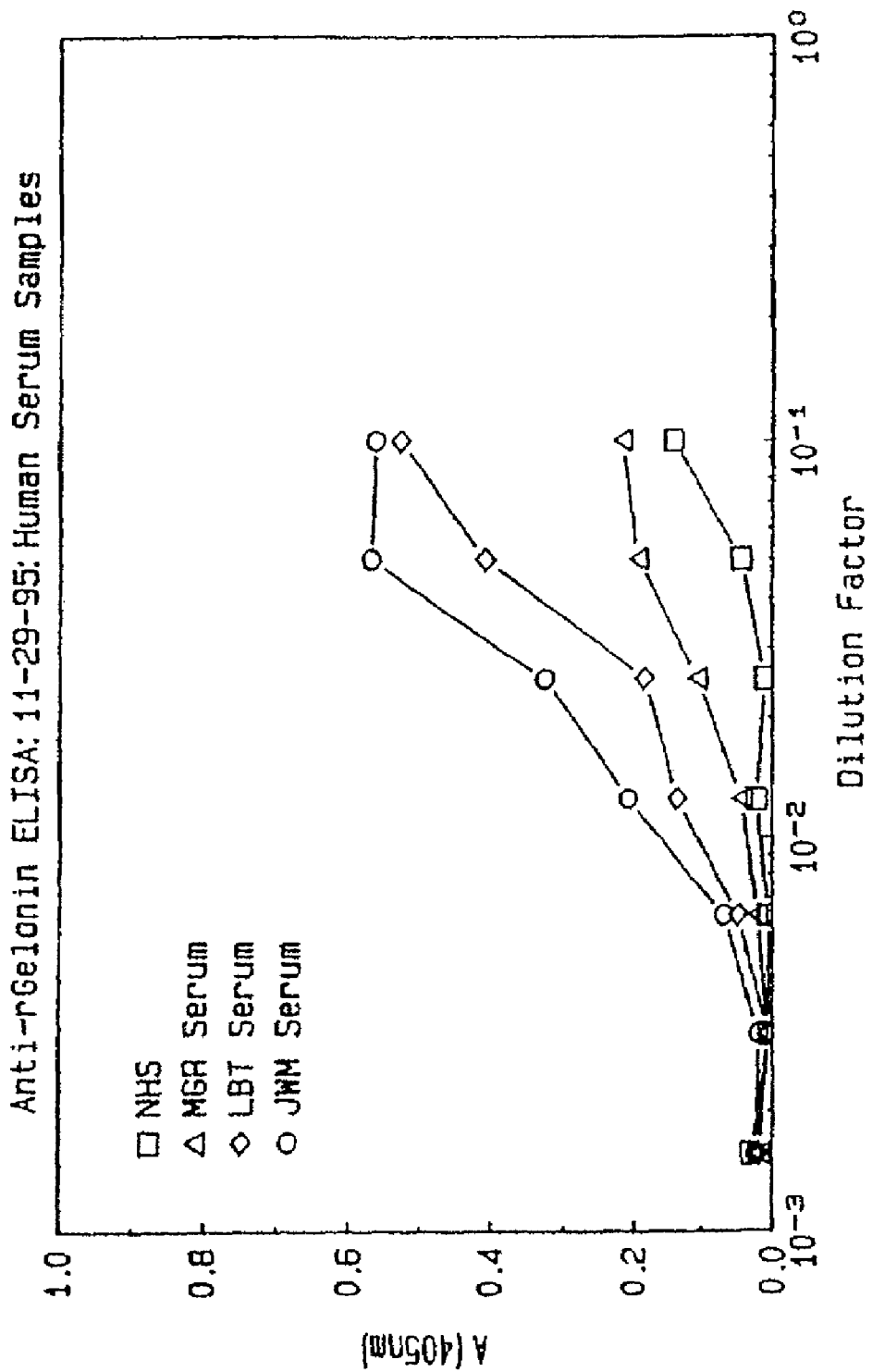
FIG. 1. ELISA done with anti-rGelonin antibody against human serum samples.

Proteins and polypeptides with reduced antigenicity can provide tremendous benefits as compositions administered to an organism with an immune system. Methods of designing and producing such proteins and polypeptides are described herein, as are the resultant molecules. Enzymes are particularly interesting candidates for these methods because it may be desirable to preserve the enzymatic activity of a particular enzyme, but also reduce its antigenicity in a subject that may benefit from the protein's enzymatic activity. Ribosome-inactivating proteins (RIPs) are an example of such a protein. Thus, in some embodiments of this invention, nucleic acid and polypeptide compositions are provided that involve plant toxins, such as gelonin. Proteins may be designed to provide the toxic function of one polypeptide in a combination with another polypeptide, such as a targeting molecule. These designer toxins have a wide variety of applications.

I. PROTEINACEOUS COMPOUNDS

In certain embodiments, the present invention concerns novel compositions comprising a proteinaceous molecule that has been modified relative to a native or wild-type protein. In some embodiments that proteinaceous compound has been deleted of amino acid residues; in other embodiments, amino acid residues of the proteinaceous compound have been replaced, while in still further embodiments both deletions and replacements of amino acid residues in the proteinaceous compound have been made. Furthermore, a proteinaceous compound may include an amino acid molecule comprising more than one polypeptide entity. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. Furthermore, these terms may be applied to fusion proteins or protein conjugates as well.

In certain embodiments the size of the at least one proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000, 1100, 1200, 1300, 1400, 1500, 1750, 2000, 2250, 2500 or greater amino molecule residues, and any range derivable therein. Compounds of the invention may include the above-mentioned number of contiguous amino acids from SEQ ID NO:1 and/or SEQ ID NO:11. It is contemplated that embodiments with respect to SEQ ID NO:1 may be employed with respect to any other amino acid sequences described herein, including SEQ ID NO:11, and vice versa, if appropriate.

Accordingly, the term "proteinaceous composition" encompasses amino molecule sequences comprising at least one of the 20 common amino acids in naturally synthesized proteins, or at least one modified or unusual amino acid, including but not limited to those shown on Table 1A below.

TABLE 1A

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

1. Functional Aspects

The present invention concerns modified proteins, particularly those that confer a therapeutic benefit to a subject because the modified protein exhibits a functional activity that is comparable to the unmodified protein, yet the modified protein possesses an additional advantage in the subject over the unmodified protein, such as having less antigenicity and/or eliciting fewer side effects, and/or having better or longer efficacy. Thus, when the present application refers to the function or activity of "modified protein" one of ordinary skill in the art would understand that this includes, for example, a protein that 1) performs the same activity or has the same specificity as the unmodified protein, but that may have a different level of activity; and 2) possesses an additional advantage over the unmodified protein. Determination of activity may be achieved using assays familiar to those of skill in the art, particularly with respect to the protein's activity, and may include for comparison purposes, for example, the use of native and/or recombinant versions of either the modified or unmodified protein.

2. Modified Proteins

Modified proteins of the present invention may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region—that is, a region of the protein determined to be antigenic in a particular organism, such as the type of organism that may be administered the modified protein.

Substitutional or replacement variants typically contain the exchange of one amino acid for another at one or more sites within the protein and may be designed to modulate one or more properties of the polypeptide, particularly to reduce its immunogenicity/antigenicity, reduce any side effects in a subject, or increase its efficacy. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. An antigenic region of a polypeptide may be substituted for a less antigenic region; the less antigenic region may contain residues that are identical to the corresponding residues in the native protein, yet also contain some conservative substitutions and/or nonconservative substitutions.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, binding sites to substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the nonidentical residues, at least 30% of them are conservative differences, as described herein, with respect to the second proteinaceous molecule; or 3) at least 30% of the proteinaceous molecule has sequence identity with the second proteinaceous molecule, but with possible gaps of nonidentical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may homology of at least 30%, 35%, 40%, 45%, 50%, 55%, 60%, 65%, 70%, 75%, 80%, 85%, 90%, 95%, or more between two proteinaceous molecules or portions of proteinaceous molecules.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Table 2 provides a list of proteins and polypeptides that may be modified according to the methods of the present invention described herein. Non-human polypeptides are specifically contemplated as targets of the methods of the invention to reduce their antigenicity in a human. It is contemplated that non-human proteins with therapeutic value are within the scope of the invention. Any other proteins or polypeptides discussed in the specification may be modified according to methods of the present invention.

TABLE 2

| Protein Genus | Protein Subgenus | Protein Species | Protein Subspecies |
|---|---|---|---|
| 1) Toxins | Ribosome Inhibitory Proteins | | |
| | | Gelonin | |
| | | Ricin A Chain | |
| | | Pseudomonas Exotoxin | |
| | | Diptheria Toxin | |
| | | Mitogillin | |
| | | Saporin | |
| 2) Cytokines/Growth Factors | Interleukins | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 | |
| | TNF | | |
| | LT | | |
| | Interferons | IFNα, IFNβ, IFNγ | |
| | Colony Stimulating Factors | GM-CSF, G-CSF, M-CSF, CSF | |
| | LIF | | |
| | Fibroblast Growth Factors | bFGF, FGF, FGF-1, FGF-2, FGF-3, FGF-4, FGF-8, FGF-9, FGF-10, FGF-18, FGF-20, FGF, 23 | |
| | VEGF | | |
| 3) Enzymes | Oxidoreductases | | |
| | Transferases | Transferring one-carbon groups | Methyltransferases |
| | | | Carboxyl and carbamoyltransferases |
| | | | Amidinotransferases |
| | | Transferring aldehyde or ketone residues | |
| | | Acyltransferases | Acyltransferases |
| | | | Aminoacyltransferases |

TABLE 2-continued

| Protein Genus | Protein Subgenus | Protein Species | Protein Subspecies |
|---|---|---|---|
| | | Glycosyltransferases | Hexosyltransferases |
| | | Transferring alkyl or aryl groups, other than methyl groups | |
| | | Transferring nitrogenous groups | Transaminases |
| | | | Oximinotransferases |
| | | Transferring phosphorous-containing groups | Phosphotransferases |
| | | | Diphosphotransferases |
| | | | Nucleotidyltransferases |
| | | Transferring sulfur-containing groups | Sulfur-transferases |
| | | | Sulfotransferases |
| | | | CoA-transferases |
| | | Transferring selenium-containing groups | |
| | Hydrolases | Acting on ester bonds | |
| | | Glycosylases | |
| | | Acting on ether bonds | |
| | | Acting on peptide bonds (peptide hydrolases) | |
| | | Acting on carbon-nitrogen bonds, other than peptide bonds | |
| | | Acting on acid anhydrides | |
| | | Acting on carbon-carbon bonds. | |
| | | Acting on halide bonds | |
| | | Acting on phosphorus-nitrogen bonds. | |
| | | Acting on sulfur-nitrogen bonds | |
| | | Acting on carbon-phosphorus bonds | |
| | | Acting on sulfur-sulfur bonds | |
| | Lyases | Carbon-carbon lyases. | |
| | | Carbon-oxygen lyases | |
| | | Carbon-nitrogen lyases | |
| | | Carbon-sulfur lyases | |
| | | Carbon-halide lyases | |
| | | Phosphorus-oxygen lyases | |
| | Isomerases | Racemases and epimerases | |
| | | Cis-trans-isomerases | |
| | | Intramolecular oxidoreductases | |
| | | Intromolecular transferases (mutases) | |
| | | Phosphotransferases (phosphomutases) | |
| | Ligases | Forming carbon-oxygen bonds | |
| | | Forming carbon-sulfur bonds | |
| | | Forming carbon-nitrogen bonds. | |
| | | Forming carbon-carbon bonds | |
| | | Forming phosphoric ester bonds | |

Another embodiment for the preparation of modified polypeptides according to the invention is the use of peptide mimetics. Mimetics are peptide-containing molecules that mimic elements of protein secondary structure. See, e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation modified protein molecules having many of the natural properties of a native protein, but with altered and, in some cases, even improved characteristics.

3. Multipolypeptide Proteinaceous Compounds

The present invention concerns a proteinaceous compound that may include amino acid sequences from more than one polypeptide. A proteinaceous compound or molecule, for example, could include a modified toxin with an antigen binding region of an antibody. The multipolypeptide proteinaceous molecule may be two or more proteins chemically conjugated to one another or it may be a fusion protein of two or more polypeptides encoded by the same nucleic acid molecule. A fusion or conjugated protein comprising a toxin and a second polypeptide with activity may be referred to as a "dual toxin." Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Designer toxins themselves in general, have no capability to bind to the cell surface or internalize within specific cells. Therefore, these agents require either chemical conjugation to or fusion with agents/proteins which are capable of binding to specific target cells and internalizing into the cell efficiently once bound. Table 3 provides a list of proteins and polypeptides that may be conjugated or fused to toxins of the present invention, particularly in embodiments involving targeting the engineered proteinaceous compounds to a particular placed, such as specific cell types or parts of the body. The invention further includes adjoining all or part of a toxin molecule to all or part of any of the proteins listed in Table 2. It is contemplated that the invention includes, but is not limited to, the examples provided in these Tables 2 and 3.

TABLE 3

| Genus | Subgenus | Species | Subspecies |
|---|---|---|---|
| 1) Antibodies | Polyclonal | | |
| | Monoclonal | non-recombinant | |
| | | recombinant | |
| | | | chimeric |
| | | | single chain |
| | | | diabody |
| | | | multimeric |
| 2) Cytokines/ Lymphokines/ Growth Factors | Interleukins | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 | |
| | EGF | | |
| | Colony Stimulating Factors (CSF) | GM-CSF, G-CSF, M-CSF | |

TABLE 3-continued

| Genus | Subgenus | Species | Subspecies |
|---|---|---|---|
| 3) Small Chemical That Bind Cell Surface and Are Internalized | Nicotine | | |
| | ATP | | |
| | Amino Acids | | |
| | Dopamine | | | a. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope or other tag, to facilitate targeting or purification of the fusion protein. The use of 6×His and GST (glutathione S transferase) as tags is well known. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

Immunotoxins are specifically contemplated as an embodiment of the present invention. An immunotoxin is a cytotoxic compound comprising at least a portion of an antibody and a portion of a toxin molecule. The antibody and the toxin may be fused or conjugated to each other. More detail about immunotoxins is provided infra.

b. Conjugated Proteins

The present invention further provides conjugated polypeptides, such as translated proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al, 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins."

Antibody conjugates may be employed for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$ iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody is conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

i. Linkers/Coupling Agents

Multiple peptides or polypeptides, such as with a conjugated immunotoxin, may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase, or stromelysin. Alternatively, peptides or polypeptides may be joined to an adjuvant.

Amino acids such as selectively-cleavable linkers, synthetic linkers, or other amino acid sequences may be used to separate proteinaceous moieties. Additionally, while numerous types of disulfide-bond containing linkers are known that can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action. Furthermore, certain advantages in accordance with the invention will be realized through the use of any of a number of toxin moieties, including gelonin and a deglycosylated A chain of ricin.

It can be considered as a general guideline that any biochemical cross-linker that is appropriate for use in an immunotoxin will also be of use in the present context, and additional linkers may also be considered.

Cross-linking reagents are used to form molecular bridges that tie together functional groups of two different molecules, e.g., a stabilizing and coagulating agent. To link two different proteins in a step-wise manner, hetero-bifunctional cross-linkers can be used that eliminate unwanted homopolymer formation.

It is contemplated that cross-linkers may be implemented with the modified protein molecules of the invention. Bifunctional cross-linking reagents have been extensively used for a variety of purposes including preparation of affinity matrices, modification and stabilization of diverse structures, identification of binding sites, and structural studies. In the context of the invention, such cross-linker may be used to stabilize the polypeptide or to render it more useful as a therapeutic, for example, by improving the modified protein's targeting capability or overall efficacy. Cross-linkers may also be cleavable, such as disulfides, acid-sensitive linkers, and others. Homobifunctional reagents that carry two identical functional groups proved to be highly efficient in inducing cross-linking between identical and different macromolecules or subunits of a macromolecule, and linking of polypeptides to specific binding sites on binding partners. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 3 details certain hetero-bifunctional cross-linkers considered useful in the present invention.

TABLE 4

HETERO-BIFUNCTIONAL CROSS-LINKERS

| Linker | Reactive Toward | Advantages and Applications | Spacer Arm Length\after cross-linking |
| --- | --- | --- | --- |
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |

TABLE 4-continued

HETERO-BIFUNCTIONAL CROSS-LINKERS

| Linker | Reactive Toward | Advantages and Applications | Spacer Arm Length\after cross-linking |
|---|---|---|---|
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide, such as gelonin, does not contain a residue amenable for a given cross-linking reagent in its native sequence, conservative genetic or synthetic amino acid changes in the primary sequence can be utilized.

4. Protein Purification

While some of the embodiments of the invention involve recombinant proteins, the invention concerns also methods and processes for purifying proteins, including modified proteins and recombinant proteins. Generally, these techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC. In addition, the conditions under which such techniques are executed may be affect characteristics, such as functional activity, of the purified molecules.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur. A "substantially purified" protein or peptide Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, about 96%, about 97%, about 98%, about 99%, about 99.2%, about 99.4%, about 99.6%, about 99.8%, about 99.9% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

The use of a peptide tag in combination with the methods and compositions of the invention is also contemplated. A tag takes advantage of an interaction between two polypeptides. A portion of one of the polypeptides that is involved in the interaction may used as a tag. For instance, the binding region of glutathione S transferase (GST) may be used as a tag such that glutathione beads can be used to enrich for a compound containing the GST tag. An epitope tag, which an amino acid region recognized by an antibody or T cell receptor, may be used. The tag may be encoded by a nucleic acid segment that is operatively linked to a nucleic acid segment encoding a modified protein such that a fusion protein is encoded by the nucleic acid molecule. Other suitable fusion proteins are those with β-galactosidase, ubiquitin, hexabistidine (6×His), or the like.

5. Antibodies

In certain embodiments, the present invention involves antibodies. For example, all or part of a monoclonal, single chain, or humanized antibody may be chemically conjugated or recombinantly fused to another proteinaceous compound such as a modified gelonin toxin. Alternatively, other aspects of the invention involve recognizing an immune response, that is, an antibody response, to a particular antigen or antigenic region in order to design and/or prepare a proteinaceous compound with less immunogenicity than a native form of the proteinaceous compound. As detailed above, in addition to antibodies generated against full length proteins, antibodies also may be generated in response to smaller constructs comprising epitopic core regions, including wild-type and mutant epitopes. An epitope is an antigenic determinant. An antigen is any substance that is specifically recognized by an antibody or T-cell receptor. An immunogen is an antigen that induces a specific immune response.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art.

Means for preparing and characterizing antibodies are also well known in the art (See, e.g., Harlow and Lane, "Antibodies: A Laboratory Manual," Cold Spring Harbor Laboratory, 1988; incorporated herein by reference).

The methods for generating monoclonal antibodies (mAbs) generally begin along the same lines as those for preparing polyclonal antibodies. Briefly, a polyclonal antibody may be prepared by immunizing an animal with an immunogenic polypeptide composition in accordance with the present invention and collecting antisera from that immunized animal. Alternatively, in some embodiments of the present invention, serum is collected from persons who may have been exposed to a particular antigen. Exposure to a particular antigen may occur a work environment, such that those persons have been occupationally exposed to a particular antigen and have developed polyclonal antibodies to a peptide, polypeptide, or protein. In some embodiments of the invention polyclonal serum from occupationally exposed persons is used to identify antigenic regions in the gelonin toxin through the use of immunodetection methods.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 $mg/m^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection also may be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

mAbs may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate mAbs. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. Such antibodies are generally useful for in vivo therapeutic applications. This strategy reduces the host response to the foreign antibody and allows selection of the human effector functions.

"Humanized" antibodies are also contemplated, as are chimeric antibodies from mouse, rat, or other species, bearing human constant and/or variable region domains, bispecific antibodies, recombinant and engineered antibodies and fragments thereof. The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope. Examples of other teachings in this area include U.S. Pat. Nos. 6,054,297; 5,861,155; and 6,020,192, all specifically incorporated by reference. Methods for the development of antibodies that are "custom-tailored" to the patient's disease are likewise known and such custom-tailored antibodies are also contemplated.

6. Immunodetection Methods

As discussed, in some embodiments, the present invention concerns immunodetection methods for binding, purifying, removing, quantifying and/or otherwise detecting biological components such as antigenic regions on polypeptides and peptides. The immunodetection methods of the present invention can be used to identify antigenic regions of a peptide, polypeptide, or protein that has therapeutic implications, particularly in reducing the immunogenicity or antigenicity of the peptide, polypeptide, or protein in a target subject.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle M H and Ben-Zeev O, 1999; Gulbis B et al., 1993; De Jager R et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with antibodies. After binding and/or washing to remove non-specifically bound immune complexes, the bound anti-antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to evaluate a particular immunotoxin of the present invention. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

II. NUCLEIC ACID MOLECULES

A. Polynucleotides Encoding Native Proteins or Modified Proteins

The present invention concerns polynucleotides, isolatable from cells, that are free from total genomic DNA and that are capable of expressing all or part of a protein or polypeptide. The polynucleotide may encode a native protein that may be manipulated to encode a modified protein. Alternatively, the polynucleotide may encode a modified protein, or it may encode a polynucleotide that will be used to make a fusion protein with a modified protein. For example, a polynucleotide may encode multiple moieties such as a modified gelonin polypeptide that is covalently attached to a targeting polypeptide, e.g., a tumor antigen. It is contemplated that a single polynucleotide molecule may encode, 1, 2, 3, 4, 5, 6, 7, 8, 9, 10, or more different polypeptides (all or part). Any of the polypeptides, proteins, or peptides disclosed in Table 2 may be produced recombinantly as part of the disclosed invention. Furthermore, any of the proteinaceous compounds in Table 2 may be encoded with one or more other polypeptides in Table 2 or disclosed herein on the same nucleic acid molecule such that a fusion protein is created. Recombinant proteins can be purified from expressing cells to yield active proteins. Thus, embodiments of the invention include the use of nucleic acids encoding all or part of SEQ ID NO:1. Such nucleic acids include all or part of SEQ ID NO:2, which corresponds to the cDNA sequence encoding a gelonin polypeptide (GenBank accession number L12243. Thus, it is contemplated that any of the methods and compositions discussed herein with respect to nucleic acids may be applied with respect to SEQ ID NO:2.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "polynucleotide" refers to a nucleic acid molecule that has been isolated free of total genomic nucleic acid. Therefore, a "polynucleotide encoding a native polypeptide" refers to a DNA segment that contains wild-type or polymorphic polypeptide-coding sequences isolated away from, or purified free from, total mammalian or human genomic DNA. Therefore, for example, when the present application refers to the function or activity of gelonin, "native gelonin polypeptide," or "modified gelonin polypeptide" that is encoded by a gelonin polynucleotide, it is meant that the polynucleotide encodes a molecule that has enzymatic activity as a RIP.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 1 above).

Similarly, a polynucleotide comprising an isolated or purified wild-type, polymorphic, or mutant polypeptide gene refers to a DNA segment including wild-type, polymorphic, or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: about, at least, or at most 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. Such lengths of contiguous residues may apply to any nucleic acid sequence described or discussed herein, including SEQ ID NOs:2-10.

In particular embodiments, the invention concerns isolated DNA segments and recombinant vectors incorporating DNA sequences that encode a wild-type, polymorphic, or modified polypeptide or peptide that includes within its amino acid sequence a contiguous amino acid sequence in accordance with, or essentially corresponding to a native polypeptide. Thus, an isolated DNA segment or vector containing a DNA segment may encode, for example, a modified gelonin polypeptide that has the ribosome-inactivating activity and specificity of a native gelonin polypeptide, yet have differing amino acids. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated gelonin polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to the a particular gene, such as the toxin gelonin. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides, for example, a modified gelonin toxin. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

1. Vectors

Native and modified polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Tables 5 lists several elements/promoters that may be employed, in the context of the present invention, to regulate the expression of a gene. This list is not intended to be exhaustive of all the possible elements involved in the promotion of expression but, merely, to be exemplary thereof. Table 6 provides examples of inducible elements, which are regions of a nucleic acid sequence that can be activated in response to a specific stimulus.

TABLE 5

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |

TABLE 5-continued

Promoter and/or Enhancer

| Promoter/Enhancer | References |
| --- | --- |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987; Treisman, 1986; Deschamps et al., 1985 |
| c-HA-ras | Trimble and Hozumi, 1987 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 6

Inducible Elements

| Element | Inducer | References |
| --- | --- | --- |
| MT II | Phorbol Ester (TPA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

4. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

B. Nucleic Acid Detection

In addition to their use in directing the expression of designer toxin and modified proteins, polypeptides and/or peptides, the nucleic acid sequences disclosed herein have a variety of other uses. For example, they have utility as probes or primers for embodiments involving nucleic acid hybridization. Detection of nucleic acids encoding modified proteins or designer toxins are encompassed by the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:1 or any other SEQ ID NO are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

C. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

III. RIBOSOME-INACTIVATING PROTEINS

Ribosome-inhibitory toxins (RITs) are potent inhibitors of protein synthesis in eukaryotes. The enzymatic domain of these proteins acts as a cytotoxic n-glycosidase that is able to inactivate catalytically ribosomes once they gain entry to the intracellular compartment. This is accomplished by cleaving the n-glycosidic bond of the adenine at position 4324 in the 28srRNA, which irreversibly inactivates the ribosome apparently by disrupting the binding site for elongation factors. RITs, which have been isolated from bacteria, are prevalent in higher plants. In plants, there are two types: Type I toxins possess a single polypeptide chain that has ribosome inhibiting activity, and Type II toxins have an A chain, comparable to the Type I protein, that is linked by a disulfide bond to a B chain possessing cell-binding properties. Examples of Type I RITs are gelonin, dodecandrin, tricosanthin, tricokirin, bryodin, mirabilis antiviral protein, barley ribosome-inactivating protein (BRIP), pokeweed antiviral proteins (PAPs), saporins, luffins, and momordins. Type II toxins include ricin and abrin. Toxins may be conjugated or expressed as a fusion protein with any of the polypeptides discussed herein. Alternatively, the modified toxins of the present invention may be conjugated to a small molecule, such as a chemotherapeutic or a targeting agent.

A. Immunotoxins

The toxins of the invention are particularly suited for use as components of cytotoxic therapeutic agents. These cytotoxic agents may be used in vivo to selectively eliminate a particular cell type to which the toxin component is targeted by the specific binding capacity of a second component. To form cytotoxic agents, modified toxins of the present invention may be conjugated to monoclonal antibodies, including chimeric and CDR-grafted antibodies, and antibody domains/fragments (e.g., Fab, Fab', F(ab').sub.2, single chain antibodies, and Fv or single variable domains). Immunoconjugates including toxins may be described as immunotoxins. An immunotoxin may also consist of a fusion protein rather than an immunoconjugate.

Modified toxins conjugated to monoclonal antibodies genetically engineered to include free cysteine residues are also within the scope of the present invention. Examples of Fab' and F(ab').sub.2 fragments useful in the present invention are described in WO 89/00999, which is incorporated by reference herein.

Alternatively, the modified toxins may be conjugated or fused to humanized or human engineered antibodies. Such humanized antibodies may be constructed from mouse antibody variable domains.

1. Antibody Regions

Regions from the various members of the immunoglobulin family are encompassed by the present invention. Both variable regions from specific antibodies are covered within the present invention, including complementarity determining regions (CDRs), as are antibody neutralizing regions, including those that bind effector molecules such as Fc regions. Antigen specific-encoding regions from antibodies, such as variable regions from IgGs, IgMs, or IgAs, can be employed with another molecule such as a toxin in combination with an antibody neutralization region or with one of the therapeutic compounds described above.

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody. Immunotoxins employing single-chain antibodies are described in U.S. Pat. No. 6,099,842, specifically incorporated by reference.

Antibodies to a wide variety of molecules are contemplated, such as oncogenes, tumor-associated antigens, cytokines, growth factors, hormones, enzymes, transcription factors or receptors. Also contemplated are secreted antibodies targeted against serum, angiogenic factors (VEGF/VPF; βFGF; αFGF; and others), coagulation factors, and endothelial antigens necessary for angiogenesis (i.e., V3 integrin). Specifically contemplated are growth factors such as transforming growth factor, fibroblast growth factor, and platelet derived growth factor (PDGF) and PDGF family members.

The present invention further embodies composition targeting specific pathogens through the use of antigen-specific sequences or targeting specific cell types, such as those expressing cell surface markers to identify the cell. Examples of such cell surface markers would include tumor-associated antigens or cell-type specific markers such as CD4 or CD8.

The antibodies employed in the present invention as part of an immunotoxin may be targeted to any antigen. The antigen may be specific to an organism, to a cell type, to a disease or condition, or to a pathogen. Exemplary antigens include cell surface cellular proteins, for example tumor-associated antigens, viral proteins, microbial proteins, post-translational modifications or carbohydrates, and receptors. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Other antigens that may be targeted include the receptors for EGF and VEGF, TIE-1 and -2, CD-33, CD38, CD-20, CD-52, GP-240, Lym-1, MMO-2, and MMP-9.

B. Other Targeting Moieties

The use of a region of a protein that mediates protein-protein interactions, including ligand-receptor interactions, also is contemplated by the present invention. This region could be used as an inhibitor or competitor of a protein-protein interaction or as a specific targeting motif. Consequently, the invention covers using the targeting moiety to recruit the toxin or other therapeutic or diagnostic polypeptide to a particular body part, organ, tissue, or cell. Once the compositions of the present invention reach the particular area through the targeting motif the toxin or other polypeptide can function.

Targeting moieties may take advantage of protein-protein interactions. These include interactions between and among proteins such as receptors and ligands; receptors and receptors; polymeric complexes; transcription factors; kinases and downstream targets; enzymes and substrates; etc. For example, a ligand binding domain mediates the protein:protein interaction between a ligand and its cognate receptor. Consequently, this domain could be used either to inhibit or compete with endogenous ligand binding or to target more specifically cell types that express a receptor that recognizes the ligand binding domain operatively attached to a therapeutic polypeptide, such as the gelonin toxin.

Examples of ligand binding domains include ligands such as VEGF/VPF; βFGF; αFGF; coagulation factors, and endothelial antigens necessary for angiogenesis (i.e., V3 integrin); growth factors such as transforming growth factor, fibroblast growth factor, colony stimulating factor, Kit ligand (KL), flk-2/flt-3, and platelet derived growth factor (PDGF) and PDGF family members; ligands that bind to cell surface receptors such as MHC molecules, among other.

The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, Nicolau et al. (1987) employed lactosyl-ceramide, a galactose-terminal asialganglioside, incorporated into liposomes and observed an increase in the uptake of the insulin gene by hepatocytes. Also, the human prostate-specific antigen (Watt et al., 1986) may be used as the receptor for mediated delivery to prostate tissue.

In still further embodiments, a lectin molecule may be used to target a compound to a cell expressing a particular carbohydrate on its surface.

1. Cytokines

Another class of compounds that is contemplated to be operatively linked to a therapeutic polypeptide, such as a toxin, includes interleukins and cytokines, such as interleukin 1 (IL-1), IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, Flk2/Flt3 ligand, GM-CSF, G-CSF, M-CSF, and tumor necrosis factor (TNF).

2. Growth Factors

In other embodiments of the present invention, growth factors or ligands can be complexed with the therapeutic agent. Examples include VEGF/VPF, FGF, TGFβ, ligands that bind to a TIE, tumor-associated fibronectin isoforms, scatter factor, hepatocyte growth factor, fibroblast growth factor, platelet factor (PF4), PDGF, KIT ligand (KL), colony stimulating factors (CSFs), LIF, and TIMP.

3. Inducers of Cellular Proliferation

Another group of proteins that may be used in conjunction with modified proteins of the present invention, such as modified gelonin toxin, comprises proteins that induce cellular proliferation. In some embodiments, the toxin is operatively linked to a ribozyme that can inactivate an inducer of cellular proliferation, while in others, the toxin is linked to the inducer itself. Alternatively, a toxin may be attached to an antibody that recognizes an inducer of cell proliferation.

The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

4. Inhibitors of Cellular Proliferation

The tumor suppressors function to inhibit excessive cellular proliferation. The inactivation of these genes destroys their inhibitory activity, resulting in unregulated proliferation. It is contemplated that toxins may be attached to antibodies that recognize mutant tumor suppressors or wild-type tumor suppressors. Alternatively, a toxin may be linked to all or part of the tumor suppressor. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, mda-7, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

5. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al. 1999).

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{XL}$, Bcl$_W$, Bcl$_S$, Mcl-1, A1, Bfl-1) or counteract Bcl-2 function and promote cell death (e.g., Bax, Bak, Bik, Bim, Bid, Bad, Harakiri). It is contemplated that any of these polypeptides, including TRAIL, or any other polypeptides that induce or promote of apoptosis, may be operatively linked to a toxin, or that an antibody recognizing any of these polypeptides may also be attached to a toxin.

IV. METHODS OF MAKING MODIFIED PROTEINS AND DESIGNER TOXINS

The present invention encompasses methods of identifying antigenic regions on a protein, methods of identifying regions that are less antigenic, methods of creating a less antigenic protein that possesses activity that is comparable to a native protein, and methods of assaying and determining antigenicity and activity.

A. Antigenic Regions

A general discussion of antibodies and antibody detection methods can be found in previous sections. The term "antigenic region" refers to a portion of a protein that is specifically recognized by an antibody or T-cell receptor. The term "less antigenic" means that a protein or region of a protein elicits a lower antibody response or is recognized by fewer antibodies (polyclonal) or the binding association with an antibody is reduced.

Antigenicity is relative to a particular organism. In many of the embodiments of the present invention, the organism is a human, but antigenicity may be discussed with respect to other organisms as well, such as other mammals-monkeys, gorillas, cows, rabbits, mice, sheep, cats, dogs, pigs, goats, etc.—as well as avian organisms and any other organism that can elicit an immune response.

In some embodiments of the present invention, polyclonal sera is employed with immunodetection methods previously discussed to identify antigenic regions in a particular protein. Polyclonal sera may be collected from a variety of sources including workers suspected to have been occupationally exposed to a particular protein; patients suspected of or diagnosed as having a condition or disease that is accompanied or caused by the presence of antibodies to a particular protein or organism; patients who no longer have been treated for a condition or disease that is accompanied by the presence of antibodies to a particular protein or organism; and random subjects.

B. Databases

In some methods of the present invention, protein databases are employed after putative antigenic regions in a particular protein are identified. A region is then compared with a database containing protein sequences from the organism in which a lower immune response against the region is desired. A number of such databases exist both commercially and publicly, including GenBank, GenPept, SwissProt, PIR, PRF, PDB, all of which are available from the National Center for Biotechnology Information website (http://www.ncbi.nlm.nih.gov/).

C. Removing and/or Replacing Antigenic Regions

Once an antigenic region is identified, it may be removed, creating a truncated protein. Alternatively, the region may be replaced with a region believed to be less antigenic.

To remove the region, the polypeptide may be cleaved with proteinases, or a polynucleotide encoding the polypeptide may be manipulated to remove the antigenic region. The region may be removed from the polynucleotide using conventional recombinant DNA technology, such as restriction enzyme or DNAses.

The region may also be replaced with substitute amino acids. "Replaced" means that an amino acid at a particular position has been substituted with a different amino acid residue or with a modified amino acid. This may be accomplished by a number of ways. The region may be first removed and then the replacement region incorporated into a polynucleotide or the polypeptide. Recombinant DNA technology may be used to incorporate a particular coding region into a polynucleotide. Alternatively, an antigenic region may be mutagenized using site-specific mutagenesis techniques that are well known to those of ordinary skill in the art.

It is contemplated that amino acids flanking either side of an antigenic region may also be removed or replaced, either to facilitate the creation of a modified protein or to improve the protein in any way, such as decrease its antigenicity, increase the protein's stability, increase the activity of the protein, decrease the activity of the protein, etc. Furthermore, multiple amino acids may be replaced or removed from either antigenic region, flanking region, or both; thus, exactly or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 620, 640, 660, 680, 700, 720, 740, 760, 780, 800, 820, 840, 860, 880, 900, 920, 940, 960, 980, 1000, or more amino acids may be removed or replaced.

Assays to determine antigenicity or activity of a modified protein are described herein, for example, in a section describing immunodetection methods, or they are well known to those of skill in the art. Appropriate assays for a particular protein will vary depending on the protein. Enzymatic assays may be appropriate to evaluate the activity of an enzyme, for example. One of skill in the art would be able to evaluate the activity of a modified protein relative to the native protein. As discussed above, a modified protein may be attached (conjugated or fused) to another polypeptide, peptide, or protein. One of skill in the art would also be able to evaluate any modified conjugated or fusion protein of the invention depending upon the activity or activities of the polypeptide components.

V. COMBINATION THERAPIES

In order to increase the efficacy of any of the therapeutic compositions of the present invention, it may be desirable to combine these compositions with other agents effective in the treatment of a particular disease or condition. It is contemplated that a wide variety of conditions or diseases may be treated, such as microbial pathogenesis, AIDS, autoimmune diseases, hyperproliferative disorders including cancers, leukemias, arthritis, inflammatory diseases, cardiovascular diseases and conditions, pathogenic diseases and conditions, and diabetes. The treatment of AIDS, cancer, and other hyperproliferative disorders is specifically contemplated. Various combinations of therapies may be employed as such, in which a composition comprising a modified protein is "A" and the secondary agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

A. Treatment of Hyperproliferative Diseases

Hyperproliferative diseases include cancer, for which there is a wide variety of treatment regimens such as anti-cancer agents or surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that therapy with modified proteins could be used similarly in conjunction with chemotherapeutic, radiotherapeutic, immunotherapeutic or other biological intervention, in addition to other pro-apoptotic or cell cycle regulating agents.

Alternatively, the gene therapy or protein administration of modified proteins may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

In some embodiments of the present invention, it is contemplated that a chemotherapeutic is operatively attached to a modified protein, such as a toxin molecule.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. As discussed above with respect to claimed compositions, the antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and immune activation may provide therapeutic benefit in the treatment of cancer, and thus, it is contemplated that immunotherapeutics may be used in conjunction with any therapeutic composition of the invention. For example, two different immunotoxins may be administered to a subject or an immunotoxin may be administered in combination with another immunotherapeutic compound in the treatment of a disease, such as cancer.

In one aspect of immunotherapy, the tumor cell must bear some marker that is amenable to targeting, i.e., is not present on the majority of other cells. Many tumor markers exist and any of these may be suitable for targeting in the context of the present invention, as discussed above. An alternative aspect of immunotherapy is to combine a pro-apoptotic effect with immune stimulatory effects. However, alternate immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with an immunotoxin directed again a tumor may enhance anti-tumor effects.

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hianibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999).

i. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

ii. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991;

Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be antiganglioside or anticarbohydrate antibodies.

iii. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al, 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

d. Genes

In yet another embodiment, the secondary treatment is gene therapy in which a therapeutic polynucleotide is administered before, after, or at the same time as a modified polypeptide or a polynucleotide encoding a modified polypeptide. Alternatively, a single vector encoding two different therapeutic polypeptide molecules may be used. A variety of proteins are encompassed within the invention, some of which are described earlier. For example, gene therapy may be employed with respect to providing a wild-type tumor suppressor gene to a cancer cell.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the anti-cancer abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Studies from a number of investigators have demonstrated that tumor cells that are resistant to TRAIL can be sensitized by subtoxic concentrations of drugs/cytokines and the sensitized tumor cells are significantly killed by TRAIL. (Bonavida et al., 1999; Bonavida et al., 2000; Gliniak et al., 1999; Keane et al., 1999). Furthermore, the combination of chemotherapeutics, such as CPT-11 or doxorubicin, with TRAIL also lead to enhanced anti-tumor activity and an increase in apoptosis. Some of these effects may be mediated via up-regulation of TRAIL or cognate receptors, whereas others may not.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

B. Viral Pathogenesis

Of course it is understood that compositions and methods of the present invention have relevance to the treatment or diagnosis of viral pathogenesis. For example, it is contemplated that the invention may be used for the treatment of AIDS, which is caused by HIV infection. Therefore, the present invention may be used in combination with the administration of traditional therapies. Some such therapies are described below.

1. AZT

A well-known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

2. HAART

New combination drug therapy has shown promising results in the treatment of HIV-infected patients. Treatment with potent anti-HIV drug combinations is referred to as "highly active antiretroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

V. PHARMACEUTICAL COMPOSITIONS AND ROUTES OF ADMINISTRATION

The present invention contemplates nucleic acid molecules encoding modified proteins (including fusion proteins), as well as modified proteins that may be conjugated to another proteinaceous compound or to a small molecule. In some embodiments, pharmaceutical compositions are administered to a subject. Different aspects of the present invention involve administering an effective amount of an aqueous composition. In another embodiment of the present invention, modified gelonin as an immunotoxin is specifically contemplated. Such compositions will generally be dissolved or dispersed in a pharmaceutically acceptable carrier or aqueous medium. Additionally, such compounds can be administered in combination with another treatment depending upon the disease or condition being treated. Treatment of AIDS could include administration of HAART or of AZT, or both, while treatment of cancer could include surgery or the administration of chemotherapy, radiotherapy, immunotherapy, or hormones.

A. Routes of Administration

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious viral particles to the patient. Similar figures may be extrapolated for liposomal or other non-viral formulations by comparing relative uptake efficiencies. Formulation as a pharmaceutically acceptable composition is discussed below.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, intrathoracic, subcutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. In cases where the present invention is used as a viral vector, a primary consideration will be the desired location for the heterologous sequences carried by the vector. Routes of administration include oral, nasal, buccal, rectal, vaginal or topical. For example, topical administration would be particularly advantageous for treatment of melanoma or AIDS-related skin conditions, or where a heterologous gene useful in treating a skin condition is carried by a viral vector. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery to the lung is contemplated. Volume of the aerosol is between about 0.01 ml and 0.5 ml. Similarly, a preferred method for treatment of colon-associated disease would be via enema. Volume of the enema is between about 1 ml and 100 ml. Direct intratumoral injection is the preferred mode, with continuous intratumoral perfusion a more specific embodiment.

In certain embodiments, it may be desirable to provide a continuous supply of therapeutic compositions to the patient. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion, for example with a viral vector carrying a heterologous nucleic acid segment, of the region of interest may be preferred. This could be accomplished by catheterization, post-operatively in some cases, followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, an expression construct encoding a modified protein may be transduced into a host cell. The transduced cells can then be used for in vitro analysis, or alternatively for in vivo administration.

U.S. Pat. Nos. 4,690,915 and 5,199,942, both incorporated herein by reference, disclose methods for ex vivo manipulation of blood mononuclear cells and bone marrow cells for use in therapeutic applications.

In vivo administration of the compositions of the present invention are also contemplated. Examples include, but are not limited to, transduction of bladder epithelium by administration of the transducing compositions of the present invention through intravesicle catheterization into the bladder (Bass, 1995), and transduction of liver cells by infusion of appropriate transducing compositions through the portal vein via a catheter (Bao, 1996). Additional examples include direct injection of tumors with the instant transducing compositions, and either intranasal or intratracheal (Dong, 1996) instillation of transducing compositions to effect transduction of lung cells.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage.

B. Lipid Compositions

In certain embodiments, the present invention concerns a novel composition comprising one or more lipids associated with a polynucleotide or polypeptide of the claimed invention. A lipid is a substance that is characteristically insoluble in water and extractable with an organic solvent. Compounds than those specifically described herein are understood by one of skill in the art as lipids, and are encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

1. Lipid Types

A neutral fat may comprise a glycerol and a fatty acid. A typical glycerol is a three carbon alcohol. A fatty acid generally is a molecule comprising a carbon chain with an acidic moiety (e.g., carboxylic acid) at an end of the chain. The carbon chain of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

2. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

3. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about $-20°$ C. Preferably, chloroform is used as the only solvent since it is more readily evaporated than methanol.

4. Lipid Composition Structures

A compound associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL) or Superfect (Qiagen) complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

a. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

b. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

5. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a lipid and/or modified protein or polynucleotide encoding a modified protein may be, for example, encapsulated in the aqueous interior of a liposome, interspersed within the lipid bilayer of a liposome, attached to a liposome via a linking molecule that is associated with both the liposome and the composition, entrapped in a liposome, complexed with a liposome, etc.

a. Making Liposomes

A liposome used according to the present invention can be made by different methods, as would be known to one of ordinary skill in the art.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the polynucleotide or polypeptide, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the compound is about 0.7 to about 1.0 μm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/therapeutic compound or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. Liposomal encapsulation has resulted in a lower toxicity and a longer serum half-life for such compounds (Gabizon et al., 1990).

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparab. Liposome Targeting Association of the compositions of the invention with a liposome may improve its biodistribution and other properties. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of any disclosed compound of the invention It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

Exemplary methods for cross-linking ligands (some discussed above) to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

i. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., (1986)) For example, disialoganglioside GD2 is a tumor antigen that has been identified neuroectodermal origin tumors, such as neuroblastoma, melanoma, small-cell lung carcenoma, glioma and certain sarcomas (Cheresh et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagnan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107, 090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a compound may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific delivery of compounds of the invention and/or targeting vehicle may comprise a specific binding ligand in combination with a liposome. The compounds to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a binding agent. Others comprise a cell receptor-specific ligand to which modified protein or a polynucleotide encoding a modified protein to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

c. Liposome/Nucleic Acid Combinations

It is contemplated that when the liposome composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

An exemplary method for targeting viral particles to cells that lack a single cell-specific marker has been described (U.S. Pat. No. 5,849,718). In this method, for example, antibody A may have specificity for tumor, but also for normal heart and lung tissue, while antibody B has specificity for tumor but also normal liver cells. The use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

d. Lipid Administration

The actual dosage amount of a lipid composition (e.g., a liposome-modified protein or polynucleotide encoding a modified protein) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

V. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention.

Example 1

Sequential Deletion Studies

The nucleotide sequence encoding recombinant gelonin (SEQ ID NO:2) was utilized as the template to create these toxins. Sequence analysis and structural modeling of rGel showed a significant folding of the molecule into pleated sheets, beta coils, and hairpin loops as shown. According to these studies, amino acids 200-277 (C-terminal) appear to fold into a binding pocket similar to that of the docking port of RTA for its B chain. Since rGel has no B chain, this "docking port" was theorized to be a vestigial portion of the toxin and may be unnecessary to the biological activity of this protein.

Sequential deletion mutants of the cDNA molecule encoding rGel from the C-terminal and from the N-terminal were created as shown in FIGS. 3A and 3B and Table 7 and designated CFR1901-CFR1905. In preliminary studies, constructs CFR 1904, 1905, 2001, 2007, and 2024 demonstrated detectable activity in Rabbit Reticulocyte Lysate Assays (RRLA). These constructs were $10^5$-$10^3$ less active than CFR 1888, which is considered within a range of "active" toxin molecules (Munishkin et al., 1995).

CFR 1901

To create CFR 1901, which has amino acids 1-46 deleted, 1 μg of purified cDNA of CFR 1888 contained in the pX2 vector (originally based on pET-22b, Novagen, Inc.) was digested with 50 units of restriction endonucleases Nco I and Sma I (Boeringer-Mannheim). The overhang fragment on the 5' Nco I site was then blunted by addition of 1 unit of Mung Bean nuclease (New England Biolabs) and incubated at 30° C. for 0.5 hr. Qiagen PCR purification kit was used to remove the Mung Bean nuclease. The resulting DNA was circularized by ligation with the 3' blunted SmaI site.

CFR 1902

CFR 1888 was digested with Nco I and Cla I restriction endonucleases. The ends were filled in to maintain the correct reading frame, using Klenow enzyme (New England Biolabs) on the 3' overhang in order to make it blunted before religation.

For protein expression, 50 ng of plasmid DNA was transformed into 50 μl of $BL21(DE3)_p$LysS competent *E. Coli* host cells (Novagen, Inc.). Individual colonies were picked and grow at 37° C. with shaking in 100 ml of Luria Broth containing 200 μg/ml of Ampicillin (Sigma Chemical Co.) up to an $OD_{600}$ between 0.6-0.8. IPTG (Boeringer-Mannheim) was then added to the culture to induce the recombinant protein at 0.1 mM final concentration. The culture was allowed to incubate for additional 2 hr at 37° C. before harvesting by centrifugation.

TABLE 7

| Name | Designation | Description and/or Amino Acid Deletion | Amino Acid Replacement/Addition | Other Functional Addition |
|---|---|---|---|---|
| 1888 | CFR 1888 | none | C-terminus KDPE change to KDEL | none |
| KS | CFR 1901 | CFR 1888 minus AA 1-46 | none | none |
| KC | CFR 1902 | CFR 1888 minus AA 1-67 | none | none |
| KB | CFR 1903 | CFR 1888 minus AA 198-251 | Additional LAAA before AA 251 | none |
| SB | CFR 1904 | CFR 1888 minus AA 1-46 and 198-251 | Additional LAAA before AA 252 | none |
| CB | CFR 1905 | CFR 1888 minus AA 1-67 and 198-251 | Additional LAAA before AA 253 | none |
| 3825 | CFR 2018 | CFR 1888 minus AA 104-111 | AA 43 = K, C; Additional L after AA 164 | none |
| | CFR 2018 | CFR 1888 replaced AA 252-257 | VDKDPKA | none |
| N10 | CFR 2001 | CFR 2018 minus AA 1-9 | none | none |
| N43 | CFR 2007 | CFR 2018 minus AA 43-70 | none | none |
| N87 | CFR 2015 | CFR 2018 minus AA 87-107 | none | none |
| N4389 | CFR 2024 | CFR 2018 minus AA 43-70 and 89-109 | none | none |
| N100130 | CFR 2005 | CFR 2018 minus AA 100-109 and 130-155 | none | none |
| C211 | CFR 2004 | CFR 2018 minus AA 194-223 and 235-252 | none | none |
| 3825-Y1 | CFR 2019 | CFR 2018 minus AA 202-252 | FQMVTIDQLKPKIALLKFVK | none |
| 3825-Y2 | CFR 2020 | CFR 2018 replaced AA 28-43 | NQWDGTQHGVELRQQ | none |
| 3825-Y3 | CFR 2021 | CFR 2018 replaced AA 73-89 | IYIMGTQERNEKLFYR | none |
| 3825-Y4 | CFR 2022 | CFR 2018 replaced AA 187-196 | EENETTCYMG | none |
| 4389-Y1 | CFR 2025 | CFR 2024 replaced AA 153-203 | FQMVTIDQLKPKIALLKFVK | none |
| 4389-Y2 | CFR 2026 | CFR 2024 replaced AA 28-42 | NQWDGTQHGVELRQQ | none |
| 4389-Y3 | CFR 2027 | CFR 2024 replaced AA 45-60 | IYIMGTQERNEKLFYR | none |
| 4389-Y4 | CFR 2028 | CFR 2024 replaced AA 138-147 | EENETTCYMG | none |
| 3825-Y1.2 | CFR 2029 | CFR 2019 replaced AA 28-43 | NQWDGTQHGVELRQQ | none |

TABLE 7-continued

| Name | Designation | Description and/or Amino Acid Deletion | Amino Acid Replacement/Addition | Other Functional Addition |
|---|---|---|---|---|
| 3825-Y1.3 | CFR 2030 | CFR 2019 replaced AA 73-89 | IYIMGTQERNEKLFYR | none |
| 3825-Y1.4 | CFR 2031 | CFR 2019 replaced AA 187-196 | EENETTCYMG | none |
| 3825-Y2.3 | CFR 2032 | CFR 2020 replaced AA 73-89 | IYIMGTQERNEKLFYR | none |
| 3825-Y2.4 | CFR 2033 | CFR 2020 replaced AA 187-196 | EENETTCYMG | none |
| 3825-Y2.3.4 | CFR 2034 | CFR 2032 replaced AA 187-196 | EENETTCYMG | none |
| 3825-Y1.2.3.4 | CFR 2035 | CFR 2034 replaced AA 202-251 | FQMVTIDQLKPKIALLKFVK | none |
| 4389-Y1.2 | CFR 2036 | CFR 2025 replaced AA 28-42 | NQWDGTQHGVELRQQ | none |
| 4389-Y1.3 | CFR 2037 | CFR 2025 replaced AA 45-60 | IYIMGTQERNEKLFYR | none |
| 4389-Y1.4 | CFR 2038 | CFR 2025 replaced AA 138-147 | EENETTCYMG | none |
| 4389-Y2.3 | CFR 2039 | CFR 2026 replaced AA 45-60 | IYIMGTQERNEKLFYR | none |
| 4389-Y2.4 | CFR 2040 | CFR 2026 replaced AA 138-147 | EENETTCYMG | none |
| 4389-Y2.3.4 | CFR 2041 | CFR 2039 replaced AA 138-147 | EENETTCYMG | none |
| 4389-Y1.2.3.4 | CFR 2042 | CFR 2041 replaced AA 153-203 | FQMVTIDQLKPKIALLKFVK | none |
| CB-Y1K | CFR 2143 | CFR 1905 replaced AA 131-137 | ISLENKWGKLFQMVTIDQLKPKIALLKFVK | none |
| SB-Y1K | CFR 2144 | CFR 1904 replaced AA 152-158 | ISLENKWGKLFQMVTIDQLKPKIALLKFVK | none |
| 3825-Y1K | CFR 2145 | CFR 2019 plus AA at c-terminus | DEL | none |
| 4389-Y1K | CFR 2146 | CFR 2025 plus AA at c-terminus | DEL | none |
| GrB-CB-Y1K | CFR 2247 | CFR 2143 plus Granzyme B | G4S linker | Human Granzyme B |
| GrB-SB-Y1K | CFR 2248 | CFR 2144 plus Granzyme B | G4S linker | Human Granzyme B |
| GrB-3825-Y1K | CFR 2249 | CFR 2145 plus Granzyme B | G4S linker | Human Granzyme B |
| GrB-4389-Y1K | CFR 2250 | CFR 2146 plus Granzyme B | G4S linker | Human Granzyme B |
| Bax-CB-Y1K | CFR 2351 | CFR 2143 plus Bax Alpha | G4S linker | Human Bax (Full Length) |
| Bax-SB-Y1K | CFR 2352 | CFR 2144 plus Bax Alpha | G4S linker | Human Bax (Full Length) |
| Bax-3825-Y1K | CFR 2353 | CFR 2145 plus Bax Alpha | G4S linker | Human Bax (Full Length) |
| Bax-4389-Y1K | CFR 2354 | CFR 2146 plus Bax Alpha | G4S linker | Human Bax (Full Length) |
| Bax(3..6)-CB-Y1K | CFR 2455 | CFR 2143 plus Bax (Truncated) | G4S linker | Human Bax (Domain 3, 4, 5, 6) |
| Bax(3..6)-SB-Y1K | CFR 2456 | CFR 2144 plus Bax (Truncated) | G4S linker | Human Bax (Domain 3, 4, 5, 6) |
| Bax(3..6)-3825-Y1K | CFR 2457 | CFR 2145 plus Bax (Truncated) | G4S linker | Human Bax (Domain 3, 4, 5, 6) |
| Bax(3..6)-4389-Y1K | CFR 2458 | CFR 2146 plus Bax (Truncated) | G4S linker | Human Bax (Domain 3, 4, 5, 6) |

Example 2

Map Antigenic Linear Peptide Domains

Antigenic domains on the rGel molecule have not been previously described in the literature. The antigenic domains of the rGel molecule can depend on either the carbohydrate or the peptide sequences of the molecule. Recombinant rGel produced in bacteria has no protein glycosylation, and therefore, antibodies directed against rGel should recognize peptide domains on the molecule.

In order to identify antigenic domains on the rGel molecule, human polyclonal antibodies were first isolated from the serum of laboratory workers occupationally exposed to recombinant gelonin. Serum obtained from three laboratory workers was added to 96-well ELISA plates coated with rGel. The plates were then developed using anti-human antibodies to identify the presence of human anti-gelonin antibodies. Serum from two of the three workers showed significant antibody titers compared to that of the control human serum (FIG. 1). Twenty ml of serum from these two workers were then obtained and polyclonal human anti-gelonin antibodies were obtained by affinity chromatography using Affi-gel affinity resin containing rGel.

Figure 2:
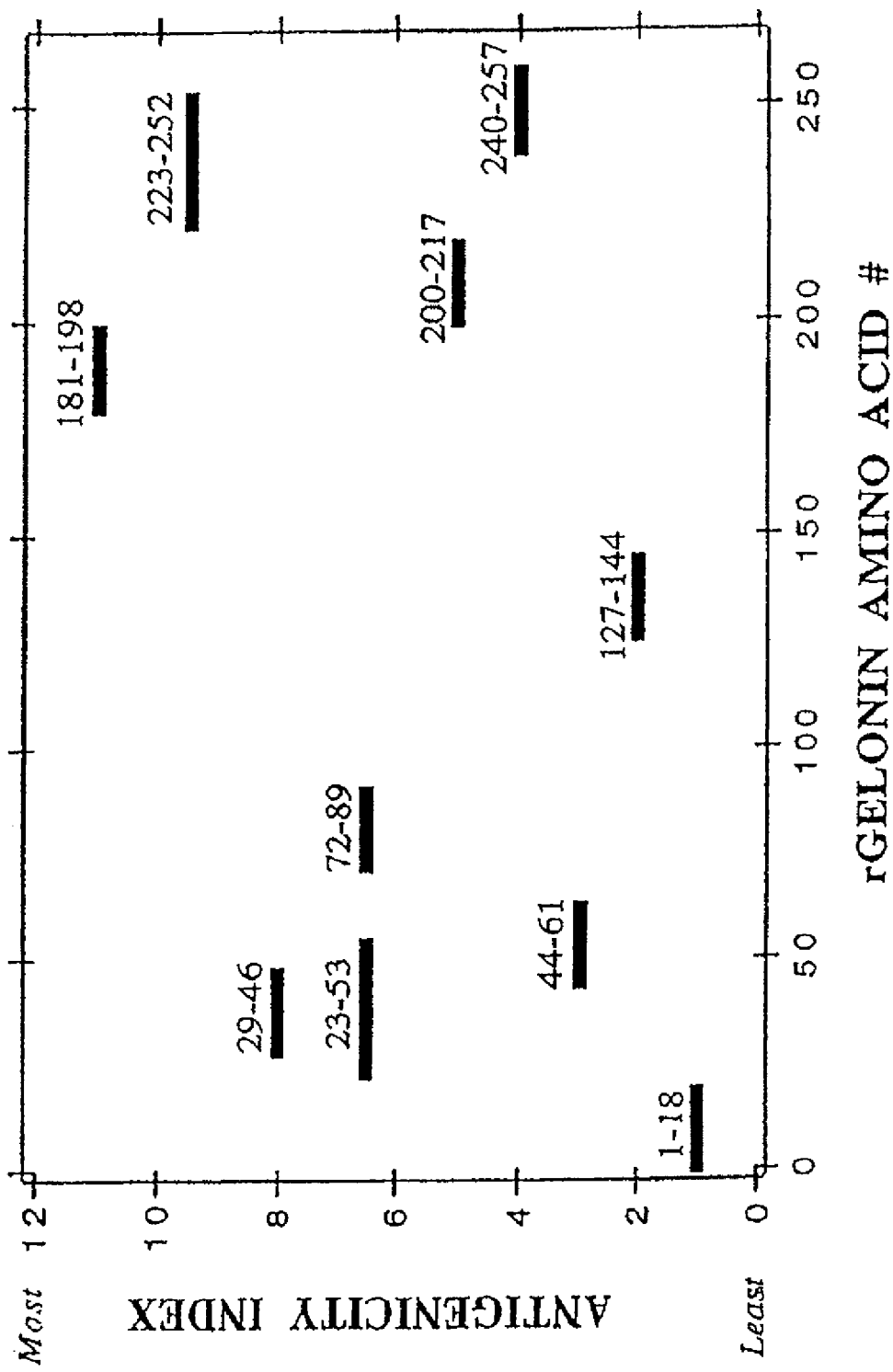
FIG. 2. Epitopes of rGelonin recognized by human anti-gelonin antibodies.

Ten peptides spanning the entire length of the rGel molecule were synthesized and then used to coat 96 well plates. A solution of the human anti-gelonin antibodies was added to the plates, allowed to react, and the presence of bound human antibodies adhering to the peptide-coated wells was assessed using ELISA. As shown in FIG. 2, significant reactivity of the polyclonal antibodies was obtained with peptides spanning 23-53 (Domain 1), 72-89 (Domain 2), 181-198 (Domain 3), and 223-252 (Domain 4). Designer toxins CFR-2001-2024 were designed to delete these antigenic domains specifically-recognized by human polyclonal antibodies to gelonin.

Example 3

Replacement of Antigenic Sequences with Human Sequences

Human/plant chimeric molecule were designed utilizing the information regarding antigenic domains obtained using human anti-gelonin antibodies above to identify four specific antigenic domains in the gelonin molecule (amino acids 205-257, 23-42, 71-88 and 189-204). These sequences were further analyzed using the GenQuest/BLAST database to search for homologies to known human proteins. An additional consideration in this study was to not only identify a "human" homologous sequence, but also to align such a sequence in the designed toxin molecule so that the enzymatic (n-glycosidic) functionality of the resulting hybrid molecule can be preserved.

Four candidate sequences for insertion into the designer toxin were identified from the database and which were used as the basis for amino acid changes (Table 8). Human homologous sequences for Domain 1 showed a high homology (40%) to human KELL protein, which is a blood group protein with a zinc binding domain. Interestingly, early studies of natural gelonin suggest that the molecule can bind zinc (Sperti et al., 1986), but these studies have not been confirmed. Analysis of Domain 4 (amino acids 189-204) demonstrated identity (40%) to human CFAH protein, which appears to play a role as a co-factor in human liver function. Domain 2 (amino acids 23-42) homology search showed 44% homology to human UTRO protein, which appears to play a role in cytoskeletal anchoring of cellular plasma membranes.

TABLE 8

HUMAN HOMOLOGUE REPLACEMENT

Y1 (205-257)
(Original)    GKLSFQIRTSGANGMFSEAVELERANGKKYYVTAVDQVKPKIALLKFLEKDPE
(Humanized)   GKL-FQMVT------------------------IDQLKPKIALLKFVK----

Y2 (23-42)
(Original)    ELRVKLKPEGNSHGIPLLRKK
(Humanized)   ELRVKNQWDGTQHGVEL-RQQ Y3 (71-88)
(Original)    SVYVVGYQVRNRSYFFKD
(Humanized)   SIYIMGIQERNEKLFYR- Y4 (189-204)
(Original)    QRIRPANNTISLENKW
(Humanized)   QRIREENETTCYMGKW Designer toxins containing antigenic site modifications and deletions were further modified in Domain 3 to conform to 100% identity with Human KELL protein. Amino acids in the designer molecule flanking the KELL sequence were also adjusted for to closely mimic the alignment of sequences in the full-length KELL protein. The final sequences designed for replacement of Domain 3 are demonstrated in Table 8. Table 9 shows the result of Gen Bank sequence homology searches for the full length proteins containing human homologous proteins.

The results of our studies clearly demonstrate that utilizing recombinant gelonin as an initial template, unique deletions can be designed, constructed and tested.

TABLE 9

Analysis of Potential Replacement Peptides for Identified
Gelonin Antigenic Sequences Designated Y-1, Y-2 Y-3 and Y-4

| Protein # | Description | | Identities(%) | Sequences |
|---|---|---|---|---|
| Y1 Replacement Query = VELERANGKKYYVTAVDQVKPK | | | | |
| P33186 | RPIG_GELMU | Gelonium Multiflorum | 100 | VELERANGKKYYVTAVDQVKPK |
| P23339 | RIPS_PHYAM | Phytolacca Americana | 47 | LELKNADGTKWIVLRVDEIKP |
| Q03464 | RIPA_PHYAM | Phytolacca Americana | 47 | LELKNANGSKWIVLRVDDIEP |
| P10297 | RIPC_PHYAM | Phytolacca Americana | 47 | LELVDASGAKWIVLRVDEIKP |
| P10978 | POLX_TOBAC | Nicotiana Tabacum | 40 | MEIESMGGNKYFVTFIDDASRK |
| Q05234 | VG27_BPML5 | Mycobacteriophage L5 | 50 | VELEGVNGERFNLTTGDQ |
| P23276 | KELL_HUMAN | Homo Sapiens | 40 | LEQRRAQGKLFQMVTIDQLK |
| P21278 | GB11_MOUSE | Mus Musculus | 38 | EFQLSDSAKYYLTDVDRI |
| Y2 Replacement Query = LRVKLKPEGNSHGIPLLRKK | | | | |
| P33186 | RIPG_GELMU | Gelonium Multiflorum | 100 | LRVKLKPEGNSHGIPLLRKK |
| P24475 | RIP3_GELMU | Gelonium Multiflorum | 89 | LRVKTKPEGNSHGIPSLRK |
| P09053 | AVTA_ECOLI | Escherichia Coli | 60 | LKLDALGNQHGIPLV |

TABLE 9-continued

Analysis of Potential Replacement Peptides for Identified
Gelonin Antigenic Sequences Designated Y-1, Y-2 Y-3 and Y-4

| Protein # | Description | | Identities(%) | Sequences |
|---|---|---|---|---|
| Q06194 | FA8_MOUSE | Mus Musculus | 47 | LSLRPHGNSHSIGANEK |
| P39138 | ARGI_BACSU | Bacillus Subtilis | 50 | LETSPSGNIHGMPL |
| P10305 | ENPP_BPT3 | Bacteriophage T3 | 61 | LRVRVKPTGTSEG |
| P43254 | COP1_ARATH | Arabidopsis Thaliana | 50 | KVEGKAQGSSHGLP |
| P46939 | UTRO_HUMAN | Homo Sapiens | 44 | RVKNQWDGTQHGVELRQQ |

Y3 Replacement
Query = SVYVVGYQVRNRSYFFKD

| P33186 | RIPG_GELMU | Gelonium Multiflorum | 100 | SVYVVGYQVRNRSYFFKD |
|---|---|---|---|---|
| P29339 | RTP2_MOMBA | Momordica Balsamina | 61 | NVYVVAYRTRDVSYFFKE |
| Q00465 | RIPA_LUFCY | Luffa Cylindrica | 50 | NVYIMGYLVNSTSYFFNE |
| P24478 | RIPS_TRIKI | Trichosanthes Kirilowii | 50 | NVYVMGYRAGDTSYFFNE |
| P02879 | RICI_RICCO | Ricinus Communis | 56 | NAYVVGYRAGNSAYFF |
| P28590 | ABRC_ABRPR | Abrus Precatorius | 44 | NAYVVAYRAGSQSYFLRD |
| P23368 | MAOM_HUMAN | Homo Sapiens | 37 | IYIMGIQERNEKLFYR |
| P36758 | VL2_HPV34 | Human Papillomavirus | 44 | SLYVIPRKLRKLRLSYFFAD |
| Q05143 | COX1_PROWI | Prototheca Wickerhamii | 50 | MYVVGLDIDTRAYF |

Y4 Replacement
Query = FQQRIRPANNTISLENKW

| P33186 | RIPG_GELMU | Gelonium Multiflorum | 100 | FQQRIRPANNTISLENKW |
|---|---|---|---|---|
| P37874 | YGXB_BACSU | Bacillus Subtilis | 41 | GQEKIPPAHSSVCLLDKW |
| P34652 | CALX_CAEEL | Caenorhabditis Elegans | 31 | KGKWIRPKISNPAFKGKW |
| P34110 | VP35_YEAST | Saccharomyces Cerevisiae | 39 | LQQFIPLVESVIVLSLKW |
| Q07009 | CAN2_RAT | Rattus Norvegicus | 33 | KLIRIRNPWGQVEWTGKW |
| P37329 | MODA_ECOLI | Eseherichia Coli | 50 | QIEAGAPADLFISADQKW |
| P14336 | POLG_TBEVM | Tick-borne Encephalitis Virus | 83 | VREDVVCYGGAWSLEEKW |
| P08603 | CFAH_HUMAN | Homo Sapiens | 40 | GGFRISEENETTCYMGKW |
| P17632 | MBHL_RHOGE | Rhodocyclus Gelatinosus | 29 | LVANIRAGDTATANVEKW |

Example 4

Designer Gelonin Toxins

The following section describes gelonin toxins that have been constructed using the methods described in the previous examples.

Deletion Toxins
CFR 1888

Starting from our original recombinant gelonin template, the C-terminus from the original KDPE was modified to KDEL to facilitate the intracellular tracking of the protein to the intracellular ribosomal compartment.

CFR 1901-1905 (See Table 7 and FIG. 3A)

Using CFR 1888 as a template, a series of sequential deletion mutants from the N and/or the C-terminus was generated to determine the sections of the molecule which could be deleted without affecting biological activity. As shown in FIG. 3A, individual deletions 1901, 1902 and 1903 were shown to be inactive. However, when single deletions were combined, (CFR1904 and CFR 1905), biological activity was re-established (FIG. 3A).

CFR 2018

Using CFR 1888 as a template, the protein was further modified as shown in Table 7 to make a slightly smaller molecule and to add an alanine residue at the C-terminus to provide improved in vivo stability during production in a bacterial host.

Toxins Based on Antigenicity Studies

Antigenic domains on the molecule were mapped using linear peptides spanning the gelonin molecule. As shown in FIG. 1, human polyclonal anti-gelonin antisera revealed four distinct antigenic domains on the molecule. Domain 1 spans amino acids 205-257, Domain 2 is composed of amino acids 23-42, Domain 3 contains amino acids 71-88, and Domain 4 consists of amino acids 89-204.

CFR2001-2024

As shown in FIG. 3B, six deletion mutants were created based on the antigenic domains observed. Three proteins showed biological activity while three proteins were inactive.

CFR2019-2042

Replacement studies creating human/plant chimeric molecules. The four antigenic domains were submitted to GenBank for sequence analysis. A Swissport protein sequence search was conducted looking for human homologous sequences based on the four antigenic domains described above.

Human Homologous Sequences

Domain 1 (amino acids 205-257) was found to map to a sequence in the human blood group protein KELL (P23276). A 40% identity and a 65% positivity was found to a sequence on this protein.

Domain 2 (amino acids 23-42) was found to have 44% identity match with the human UTRO protein (P46939).

For Domain 3 (amino acids 71-88), this sequence showed a 37% identity and a 68% positivity to the human protein MAOM (P23368). This protein is described in the Table 8.

For Domain Sequence 4, (189-204) a 40% identity was found in the human protein CFAH (P08603).

Human chimeric sequences corresponding to the four antigenic domains were generated from this data (Table 8). These sequences represent human non-antigenic replacements for the antigenic domains in the plant protein.

CFR2019-2024

Starting with CFR2019 and 2024 as templates, numerous new designer proteins were generated designated CFR2019-2042 (Table 7). These proteins represent replacement with 1, 2, 3 or 4 domains on the molecule with human chimeric homologs. Several of these Designer Toxins (CFR 2018, 2019, 2024 and 2025) were expressed in bacteria containing a 50 kDa tag and purified to homogeneity. Western analysis was performed using polyclonal antisera to the tag.

The 2019, 2024 and 2025 molecules were reduced in size compared to the starting template 2018 protein. Western analysis also demonstrates approximately equivalent reactivity to the anti-tag antibodies showing uniform loading of each toxin molecule on the SDS-PAGE. The Western blot was re-probed using antibodies to the native CFR 1888 molecule. There was good reactivity to the 2018 protein, as shown by Western blot, however, there was virtually no reactivity of this polyclonal antisera to the 2019 and 2025 designer toxins and only slight reactivity to the 2024 designer toxin. This indicates that by specific deletion (CFR2024) or replacement of antigenic domains (CFR2019), or a combination of deletion and replacement of antigenic domains (CFR2025), new toxin molecules can be created that are rendered virtually unrecognizable by antibodies to the parent molecule and thus should have a reduced antigenic profile.

CFR 2143-2146

This series of hybrid molecules was designed to incorporate optimal functional qualities of the proteins CFR1888 and CFR 2018.

CFR2247-2458

A series of molecules will be developed combining both the n-glycosidic functions of the Type I toxins with those of selected pro-apoptotic human molecules such as BAX and Granzyme B. These molecules will be assayed for the functional activity of the gelonin component and for the activities of BAX and Granzyme B. They will also be evaluated for inhibition of cell-free protein synthesis.

An evaluation may first be made on this series of molecules about the expression of BAX in cells. This can be done using BAX antibodies, such as the anti-universal Bax 6A7, in immunoassays, such as immunoprecipitations or Western blotting. After Bax expression is confirmed, cells will be measured for cell viability. This can be done by a number of ways, including using a firefly luciferase construct. To do this a mammalian expression vector pGL3 (Promega) carrying the firefly luciferase (Luc) structural gene can be transfected into a mammalian cell line along with plasmids encoding BAX and BAX fusion proteins. Luciferase activity can be measured by liquid scintillation counting using 20 ml of the cellular extract. Cell viability will be measured as the relative luciferase activity of the tested construct compared with the specified control plasmid.

Hybrids that include all or part of a granzyme B polypeptide will be evaluated for their enzymatic activity using a fluorimetric measurement of 2-naphthylamine after hydrolysis of L-glutamyl-2-naphthylamide (Bachem, Philadelphia, Pa.). Amidase activity will be measured at 21° C. with 1.00 mM L-glutamyl-2-naphthylamide in buffer A (0.3M NaCl 0.1M HEPES, adjusted to pH 7.0 with 1M NaOH, 1 mM $Na_2$ EDTA 0.05M (v/v) Triton x-100) on a Perkin-Elmer 650-10M spectrofluorimeter with fluorescence excitation at 340 nm and fluorescence emission observed at 415 nm (both with 5 nm bandpass). Small aliquots of enzyme solutions will be added to the substrate solution, and the fluorescence emission increase will be monitored for 10-40 min. Alternatively, granzyme B activity will be determined in a continuous colorimetric assay, with BAADT (N-a-t-butoxycarbonyl-L-alanyl-L-alanyl-L-aspartyl-thiobenzyl ester) as substrate. For analysis of column fractions, 1-50 µl will be added to buffer A with 1 M (v/v) 10mM BAADT in $(CH_3)$ 250 and 1 M (v/v) 11 nM dithiobis (2-nitrobenzoic acid) (Sigma) in $CH_3)_2$50 at 21° C., and the rate of absorbance increase will be measured at 405 nm on a Thermomax plate reader (Molecular Devices Inc., Palo Alto, Calif.). Absorbance increases will be converted to enzymatic rates.

Example 4

Materials and Methods for Example 5

Materials

The cDNA encoding antibody ZME-018 was amplified from hybridoma RNA obtained from hybridoma cells expressing the murine antibody using kits from Novagen (Madison, Wis.) and Invitrogen Corp. (Carlsbad, Calif.). The PCR reagents were obtained from Fisher Scientific (Pittsburgh, Pa.), and the molecular biology enzymes were purchased from either Boehringer Mannheim (Indianapolis, Ind.) or New England Biolabs (Beverly, Mass.). Bacterial strains and pEt bacterial expression plasmids were obtained from Novagen (Madison, Wis.) and growth media was purchased from Difco Laboratories (Detroit, Mich.). All other chemicals and reagents were either from Fisher Scientific or Sigma Chemical Co. (St. Louis, Mo.). Metal affinity resin (Talon) was obtained from Clontech Laboratories (Palo Alto, Calif.). Other chromatography resins and materials were from Pharmacia Biotech (Piscataway, N.J.). Tissue culture reagents were from GIBCO BRL (Gaithersburg, Md.).

Cloning of the VH and VL Domains of Antibody ZME-018

Messenger RNA from murine hybridoma FMT 112 P2 expressing antibody ZME-018 (IgG2A) was isolated using the Invitrogen Fast Track kit and transcribed to cDNA with the Invitrogen Copy Kit using the specified conditions. Amplification of antibody light and heavy chain variable regions was carried out using the Novagen Ig-Prime kit with the mouse Ig-primer set. The PCR profile for light-chain amplification was as follows: 30 cycles of 94° C.×1 min, 60° C.×1 min, and 72° C.×1 min terminated by a 5 min incubation at 72° C. For heavy-chain reactions, the identical conditions were used except that the annealing temperature was 50° C. instead of 60° C. DNA amplified using this procedure was then cloned into the Invitrogen T/A cloning vector pCR II without further purification, transformed into E. coli XL1-Blue, and identified using blue-white screening procedures. Positive clones (five each from the heavy- and light-chain libraries) were sequenced using the T7 and SP6 promoter primers and antibody domains identified by homology with other immunoglobulin sequences.

Figure 4:
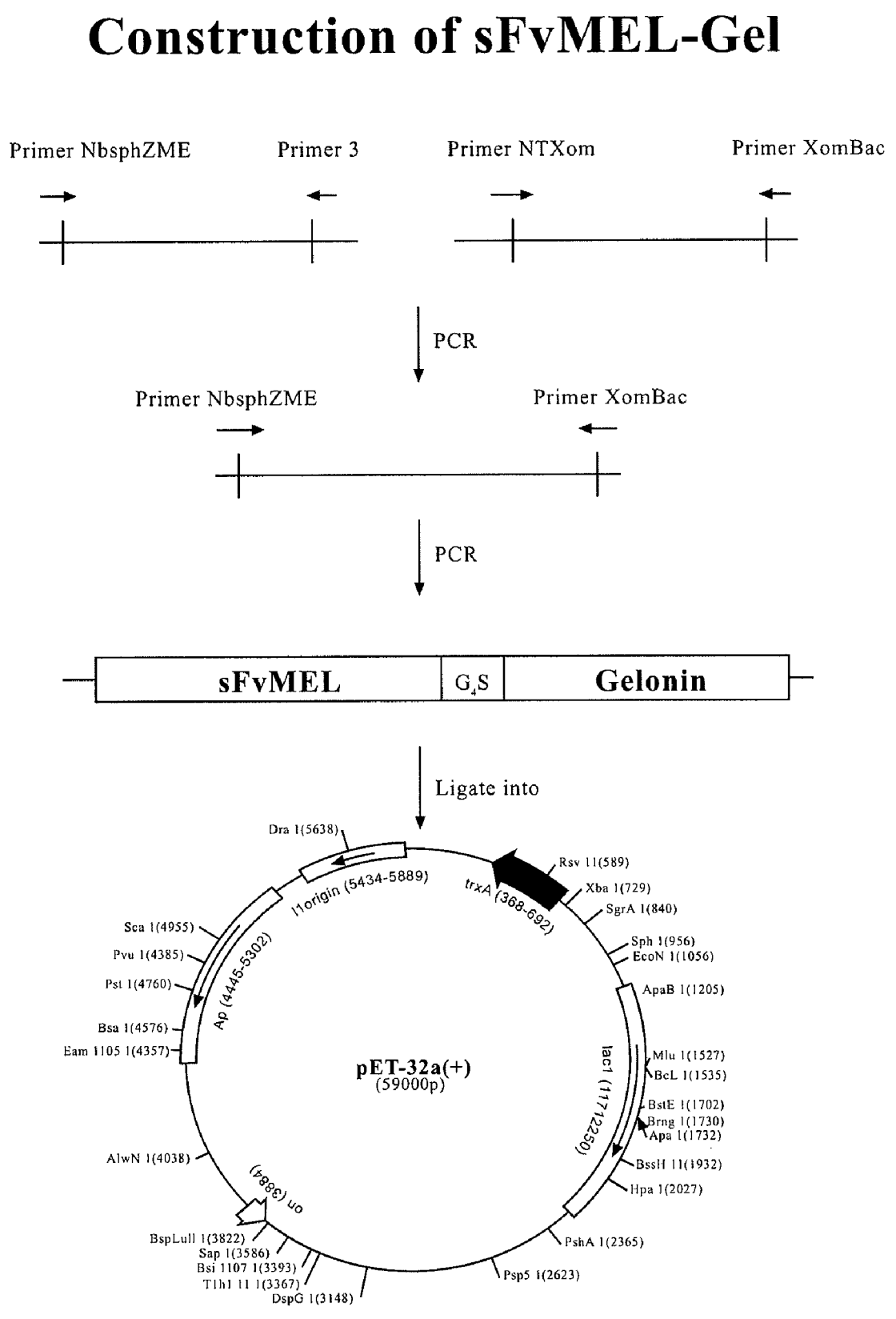

Construction of Genes Encoding the Single-Chain Antibody scfvMEL and the Immunotoxin scfvMEL/rGel A two-step splice-overlap extension PCR method (Sambrook et al., 1989) was used to construct the single-chain antibody ZME-018 using light- and heavy-chain DNA clones as templates. Light-chain sequences were amplified using the primers A (5'-GCTGCCCAACCAGCC ATGGCGGACAT-TGTGATG-3') and C (5'-GCCGGAGCCTGGCTTGC(A/C) GCTGCCGCTGGTGGAGCCTTTGATC(A/T)CCAG-3'), whereas heavy-chain DNA was amplified with the primers B (5'-AAGCCAGGCTCCGGCGAAGGCAGCACCAAAGG CGAAGTGAAGGTT-3') and D (5'-GCCACCGCCACCAC-TAGTTGAGGAGACTGT-3'). The PCR profiles for each set of reactions were as follows: 30 cycles of 1-min denaturation at 94° C., 1 min annealing at 50° C., and a 1 min extension at 72° C., followed by a final 5-min incubation at 72° C. One-tenth volume of each of these reactions were combined and used directly in a second PCR with only primers A and D following the same reaction profile as before. The final product was purified using Geneclean II (Bio 101, Vista, Calif.), digested with the restriction enzymes Nco I and Spe I, and cloned into the T7-based plasmid vector pET-22b. The genes encoding scfvMEL and recombinant gelonin were fused together using the splice-overlap extension PCR method with antibody and gelonin DNA as templates and primers NbsphZME (5'-GGCGGTGGCTCCGTCATGACGGACAT-TGTGATGACC CAGTCTCAAAAATTC-3'), primer NTXOM (5'-GGTGGCGGTGGCTCCGGTCTAG ACAC-CGTGACG-3'), and primer XOMBAC (5'-AAGGCTCGT-GTCGACCTCG AGTCATTAAGC TTTAGGATCTTTATC-3') (FIG. 4). Purified PCR products were then purified and digested as before and cloned into the vector pET-32a. Sequenced DNA clones were subsequently transformed into *E. coli* strain AD494(DE3) pLys S obtained from Novogen for expression of the fusion toxin.

Protein Expression in *E. coli*

To express the immunotoxin, bacterial cultures were incubated at 37° C. in 2×YT growth medium with strong antibiotic selection (200 µg/ml ampicillin, 70 µg/ml chloramphenicol, and 15 µg/ml of kanamycin) and grown until early log phase ($A_{600}$=0.4-0.8). The cultures were then diluted 1:1 with fresh 2×YT medium containing the same concentrations of antibiotics, and target protein expression was induced at 23° C. by the addition of 0.1 mM IPTG for 16-23 h. Induced bacterial cultures were then centrifuged and stored frozen at −80° C. for later purification.

Immunotoxin/Protein Purification

Frozen bacterial pellets from induced cultures expressing immunotoxin scFvZME-Gel were thawed at room temperature and lysed by the addition of 1 mg/ml lysozyme in 10 mM Tris-HCl, pH 8.0 for 30 min at 4° C. The bacterial lysates were then sonicated three times for 10 sec each with a cell disruptor and centrifuged at 14,000 rpm for 30 min at 4° C. The supernatant was transferred and saved on ice, and the sonication procedure was repeated with the cell pellet. Supernatants from the two lysates were then combined and ultracentrifuged at 40,000 rpm in a SS-34 rotor for 45 min at 4° C. The samples containing only soluble protein were then filtered (0.22 µm pores), adjusted to 40 mM Tris-HCl with 1M Tris-HCl (pH 8.0), and then loaded at room temperature onto a Talon metal-affinity column pre-equilibrated with the same buffer. After loading, the column was washed with 3 column volumes of loading buffer, followed by a 5-column volume wash with 40 mM Tris-HCl pH 8.0, 500 nM NaCl, and 5 mM imidazole. Bound protein was then eluted with 5 column volumes of buffer containing 40 mM Tris-HCl (pH 8.0), 500 mM NaCl and 100-200 mM imidazole. Fractions containing immunotoxin were combined, quantitated, and dialyzed into 20 mM Tris-HCl (pH 7.2), 50 mM NaCl prior to digestion with enterokinase to remove the 6×His tag using the procedure established by Novagen (Madison, Wis.).

ELISA and Western Analyses

All ELISA incubation steps were at room temperature for 1 h, unless otherwise specified, and between incubations all wells were washed with ELISA wash buffer (10 mM Tris-HCl pH 8.0, 150 mM NaCl, 0.2% Tween-20). Wells of a 96-well microtiter plate were each coated with 50,000 gp240-antigen-positive A375M melanoma cells and dried. These were then rehydrated and blocked with 3% BSA in wash buffer. Plates were incubated, and the purified immunotoxin samples, rabbit anti-gelonin polyclonal antibody (at 100 ng/ml in dilution buffer [ELISA wash buffer containing BSA at a concentration of 1 mg/ml]), and peroxidase-conjugated goat anti-rabbit IgG (Sigma, used at a 1:5,000 dilution in dilution buffer) were added. Individual wells were thoroughly washed with wash buffer, and then developed for 30 min. with ABTS (2,2'-azino-bis[3-ethylbenzthiazoline-6-sulfonic acid]) in 0.1 M citrate buffer (pH 4.2) and the signal measured at 405 nm.

For Western blots, all incubations were performed at room temperature for 1 h, unless otherwise specified. Briefly, proteins were separated by SDS-PAGE and transferred onto nitrocellulose overnight at 4° C. in transfer buffer (25 mM Tris-HCl (pH 7.5), 190 mM glycine, 20% (v/v) HPLC-grade methanol) at 40v. The filters were blocked with 5% BSA in Western blocking buffer (50 mM Tris-HCl (pH 7.5), 150 mM NaCl) and then reacted successively with rabbit anti-gelonin polyclonal antibody (at a concentration of 100 ng/mL in Western wash buffer TBS, pH 7.6, 0.5% Tween-20) and peroxidase-conjugated goat anti-rabbit IgG (Sigma, at a dilution of 1:10,000 in wash buffer). The signal was developed using the Amersham ECL detection system.

Reticulocyte Lysate In Vitro Translation Assay

The gelonin-induced inhibition of radiolabeled ($^3$H) leucine incorporation into protein in a cell-free protein synthesizing system following the administration of various doses of immunotoxin was carried out as specified by the manufacturer (Promega) and as described previously (Press et al., 1986).

Immunofluorescence Staining

Antigen-positive (A375 melanoma) cells were added to polylysine-coated 16-well chamber slides (Nunc) at $10^4$ cells per chamber and incubated at 37° C. overnight under 5% $CO^2$ atmosphere. Cells were treated with a concentration of 50 µg/ml of the scfvMEL/rGel fusion construct at various times. Cells were then washed briefly with PBS, and then proteins bound to the cell surface were stripped by incubation of 10 min with glycine buffer (500 mM NaCl, 0.1 M glycine, pH 2.5), neutralized for 5 min with 0.5 M Tris, pH 7.4, washed briefly with PBS, and then fixed in 3.7% formaldehyde (Sigma) for 15 min at room temperature, followed by a brief rinse with PBS. Cells were then permeabilized for 10 min in PBS containing 0.2% Triton X-100m, washed three times with PBS, and then incubated with PBS containing 3% BSA for 1 h at room temperature. After a brief wash with PBS, cells were incubated with either rabbit anti-scFvMEL or rabbit anti-rGel polyclonal antibodies diluted 1:500 in PBS containing 0.1% Tween-20 and 0.2% BSA for 1 h at room temperature. Cells were washed three times in PBS containing 0.1% Tween-20 PBST) for 10 min, blocked for 1 h at room temperature with PBS containing 3% BSA, followed by 1:100 diluted fluorescein isothiocyanate (FITC)-coupled anti-rabbit IgG (Sigma). Control cells were only incubated with the secondary FITC-coupled anti-rabbit IgG (1:100). After three final washes with PBST, cells were washed once in PBS for 10 min and mounted in mounting medium. Slides were analyzed with a fluorescence microscope, and each photograph was representative of at least 10 fields for each experiment at 400× magnification.

In Vitro Cytotoxicity Assay

Samples were assayed using a standard 72-h cell proliferation assay with log-phase (5,000/well) antigen-positive A375M and antigen-negative Me-180 or SK-OV-3 cell monolayers and using crystal violet staining procedures as previously described (Nishikawa et al., 1992).

In Vivo Cytotoxicity Studies

Athymic (nude) mice 4-6 weeks old were divided into groups of 5 mice per cage. Log-phase A-375 human melanoma cells ($5 \times 10^6$ cells/mouse) were injected subcutaneously in the right flank and tumors were allowed to establish. Once tumors were measurable (~30-50 mm$^2$), animals were treated (i.v. tail vein) with either saline (control) or various concentrations of the scfvMel/rGel fusion toxin for 4 consecutive days. Animals were monitored and tumors measured for an additional 30 days.

Example 5

Single-Chain Recombinant Anti-Melanoma Antibody Fused to Gelonin Design of scFvMEL/rGel Fusion Protein The variable region genes for the ZME-018 antibody and the gelonin gene (Rosenblum et al., 1999) were the templates for the construction of the anti-melanoma immunotoxin gene. As a first step, we assembled the immunotoxin in one orientation and assessed its binding and cytotoxicity to antigen-positive A375M melanoma cells. The genes encoding the antibody and gelonin fragments were linked together using a PCR-based method to construct a fusion in the antibody-gelonin orientations. The immunotoxin gene was also C-terminal tagged with a hexahistidine sequence and expressed in E. coli AD494(DE3) pLysS using the Novagen T-7-based expression vector pET-32b.

FIG. 4 illustrates the orientation of the immunotoxin expressed and also shows the sequences of amino acid linkers at the junctions of the protein domains. The antibody was constructed to encode the light chain variable region ($V_L$) at the N-terminus of the protein with an 18 amino acid flexible peptide linker (Alfthan et al., 1995) with the $V_H$ C-terminus. Gelonin (CFR2018) (referred to as rGel in this Example) was positioned downstream of the $V_H$ following another linker. We chose this configuration for reasons involving the unhindered flexibility of the antibody-binding site. With the toxin at the N-terminus of the fusion protein, a longer peptide would have been required to provide for optimal spatial orientation of the two protein moieties, and construction of this variant is in progress. DNA-sequencing studies of the final fusion gene (FIG. 5) confirmed the sequence of the final product and that no errors had been introduced using this PCR method. In addition, sequencing also confirmed that the target gene was inserted into the correct reading frame in the pET-32b vector.

The protein synthesis inhibitory activity in cell-free systems of the recombinant fusion toxin compared to that of free recombinant gelonin suggests that there is not significant stearic crowding of the gelonin active-site cleft due to proximity of the antibody fragment in our designed molecule. Also, since there are no protein cleavage sites within this fusion construct, the data also suggest that gelonin does not necessarily require cleavage from the construct to maintain biological activity. This is in sharp contrast to studies with ricin A chain (RTA), which requires release from the protein carrier to recover biological activity (Kim et al., 1988; O'Hare et al., 1990). This is surprising since gelonin and RTA share identical mechanisms of action (Stirpe et al., 1992), and also share approximately 30% sequence homology (Rosenblum et al., 1999).

Expression and Purification of Fusion Proteins

The plasmid vector pET-32b containing the fusion gene was transformed into E. coli AD494(DE3) pLysS, and the target protein was induced by the addition of IPTG. As shown by a coomassie-stained gel, a protein of the expected molecular mass (68 kDa) was induced. This protein was purified using IMAC resin, and the eluate was exposed to recombinant enterokinase (EK) to yield the final native fusion construct migrating as one band at 56 kDa. The fusion construct was also examined by Western blot using both an anti-gelonin antibody and an anti-single-chain antibody. The sfvMEL/rGel fusion construct migrating at 56 kDa reacted with both antibodies, thus demonstrating the presence of immunoreactive antibody and toxin components in the fusion construct. Estimated yields of soluble sfvMEL/rGel immunotoxin from the induced bacterial cultures were approximately 700 µg/L; however, the yield of final, purified fusion toxin were approximately 200 µg/L. The primary reason for the reduced yield was found to be an inability of the IMAC to completely capture all of the available soluble target protein. Changes made to the binding buffers and conditions as well as changing brands of IMAC capture resin did not improve these results.

ELISA Binding of Immunotoxins

Figure 6:
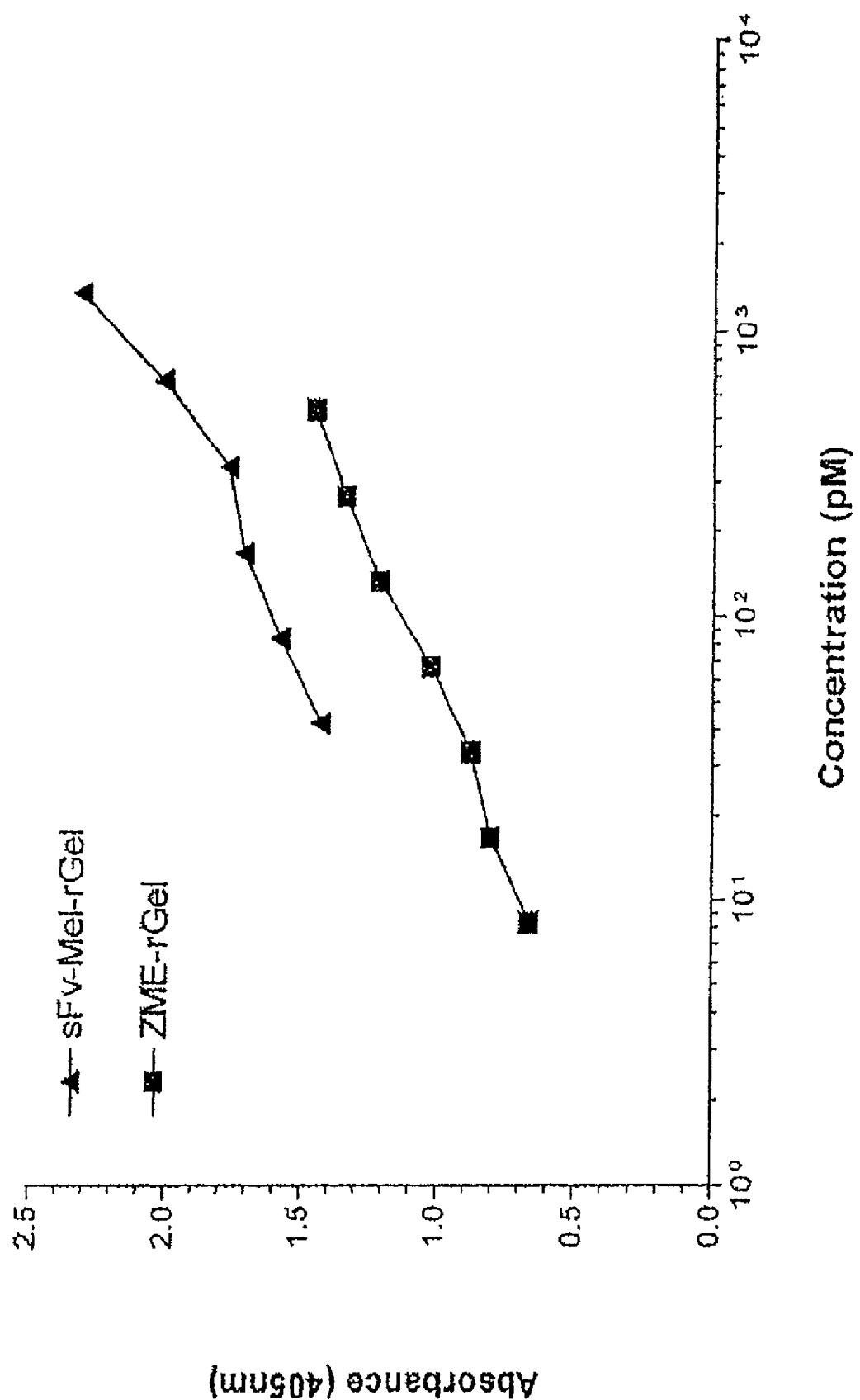
FIG. 6 Comparative binding of the parental ZME-rGel chemical conjugate and sfvMEL-rGel fusion construct (same as "sfvMEL/rGel). Binding to A-375 cells was assessed using ELISA and a polyclonal rabbit anti-gelonin polyclonal antibody. The binding of both constructs to target cells was similar although slightly higher binding was observed for the recombinant fusion construct.

To ensure that the purified fusion protein retained antigen-binding ability, the binding of this material was compared to the binding of intact IgG ZME-018-gelonin chemical conjugate and IgG ZME-018 in a competition ELISA-based binding assay (FIG. 6) using intact antigen-positive human melanoma cells as the antigen source. The scfvMEL/rGel fusion construct was found to retain binding affinities comparable with the chemical conjugate. The protein demonstrated specific and significant ELISA binding activity to target A375M melanoma cells with background levels of binding to SK-OV-3 or ME-180 cells.

Cell-Free Protein Synthesis Inhibitory Activity of the sfvMEL Fusion Toxin

The biological activity of toxins can be severely compromised when incorporated into fusion constructs. In order to examine the n-glycosidic activity of the rGel component of the fusion construct, this material was added to an in vitro protein translation assay using $^3$H-leucine incorporation by isolated rabbit reticulocytes. Inhibition curves for the fusion construct and native rGel were compared and the IC$_{50}$ values for the two molecules were found to be virtually identical (100 pM vs 104 pM, respectively).

Binding and Internalization of scfvMEL/rGel by Immunofluorescence

Immunofluorescent staining was done on A375-M cells treated with scFvMEL/rGel at different times after administration. The internalized construct was detected using either rabbit anti-rgel or rabbit anti-scFvMEL antibody followed by FITC-coupled anti-rabbit IgG. The rGel moiety of scFvMEL/rGel fusion protein was observed primarily in cytosol after treatment, and the amount of rGel in cytosol increased over time. Moreover, scFvMEL moiety of scFvMEL/rGel was also observed in cytosol. This demonstrates that the fusion construct was capable of efficient cell binding and internalization of the rGel toxin after exposure of log-phase cells.

In Vitro Cytotoxic Activity of Immunotoxins

Figure 7:
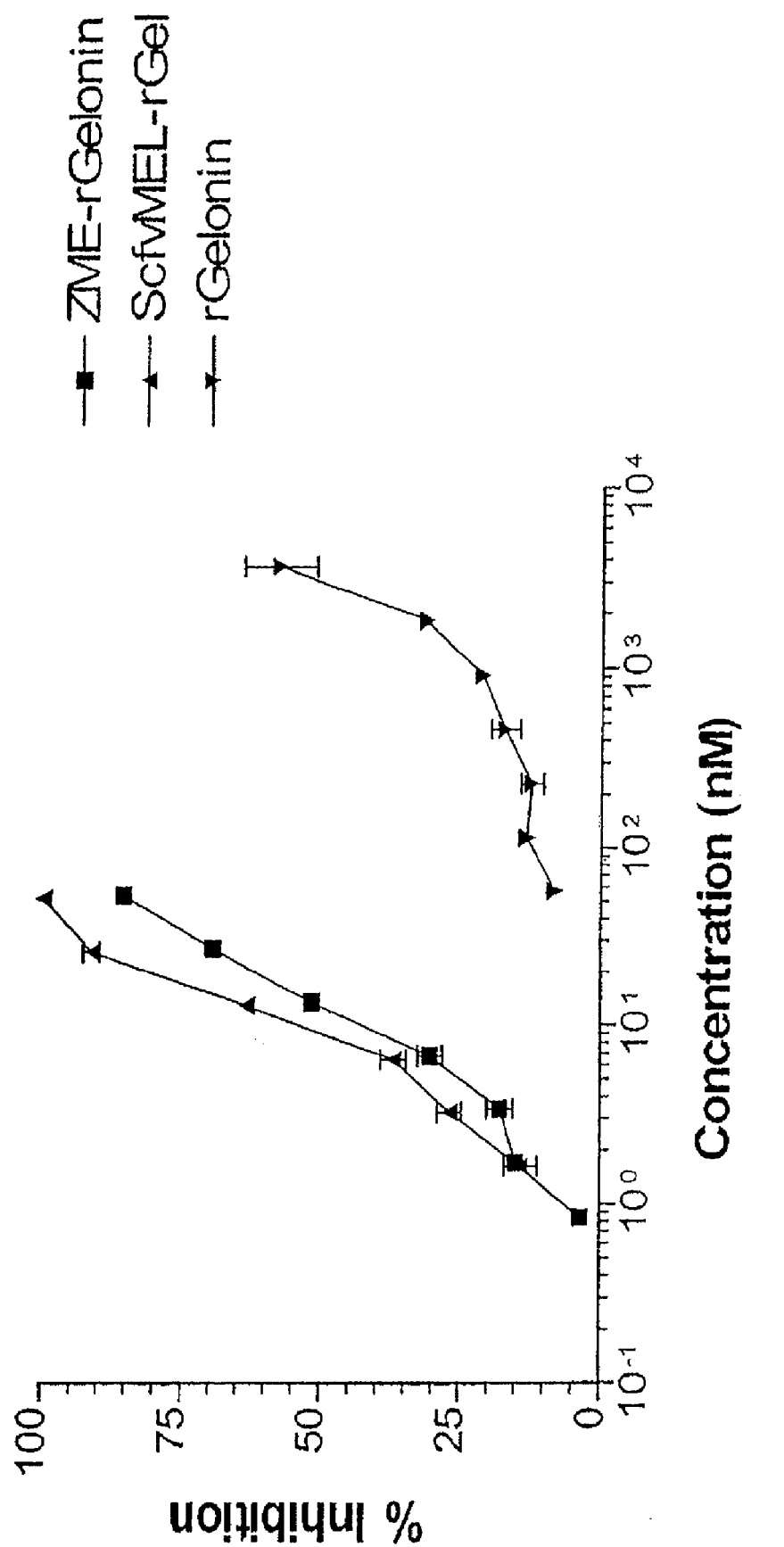
FIG. 7 Comparative in vitro cytotoxicity of the parental ZME-rGel chemical conjugate and sfvMEL-rGel fusion construct on antigen-positive A375 human melanoma cells. Cells were plated and then treated for 72 h with various doses of sfvMEL/rGel fusion construct, ZME-rGel chemical conjugate or free recombinant gelonin. $IC_{50}$ values for both immunoconjugates were approximately 8 nM, while the $IC_{50}$ for the recombinant gelonin was several orders of magnitude higher at approximately $2\times10^3$ nM.
Figure 8:
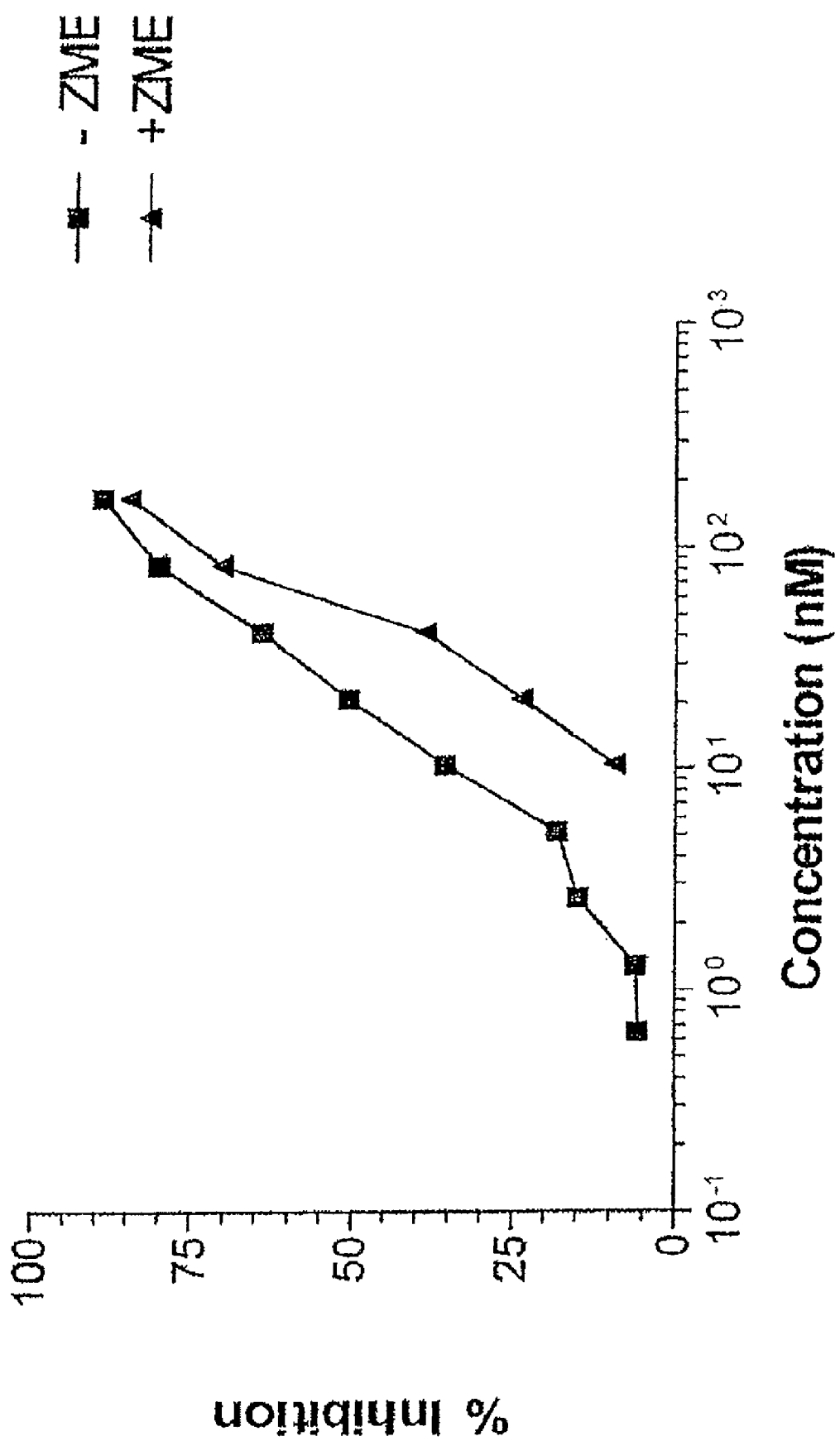
FIG. 8 Competitive inhibition of sfvMEL/rGel immunotoxin with ZME antibody. Various concentrations of the recombinant immunotoxin were added to A-375 human melanoma cells in log-phase culture in quadruplicate. To another set of wells, a fixed concentration of antibody ZME (50 μg/ml) was admixed with various doses of sfvMEL/rGel immunotoxin and incubated for 72 h. Addition of free ZME antibody resulted in approximately a 3-fold reduction in immunotoxin cytotoxicity.

The sfvMEL/rGel purified fusion protein and the original ZME/rGel chemical construct were tested for specific cytotoxicity against an antigen-positive (A375M) and an antigen-negative (SK-OV-3) cell line. As shown in FIG. 7, both the chemically-produced and the fusion construct both demonstrated IC$_{50}$ values of approximately 10 nM. In contrast, IC$_{50}$ values for the rgel toxin were approximately 200-fold higher (approximately 2,000 nM). The cytotoxic effects of the immunotoxins against antigen-negative SKOV-3 cells was similar to that of the gelonin alone. Co-administration of free ZME antibody with the sfvMEL/rGel immunotoxin (FIG. 8) as expected showed a modest shift in the dose-response curve, demonstrating a dependence of surface antigen recognition for the development of cellular toxicity of the fusion construct.

Antitumor Activity of sfvMEL/rGel in Xenograft Models

Figure 9:
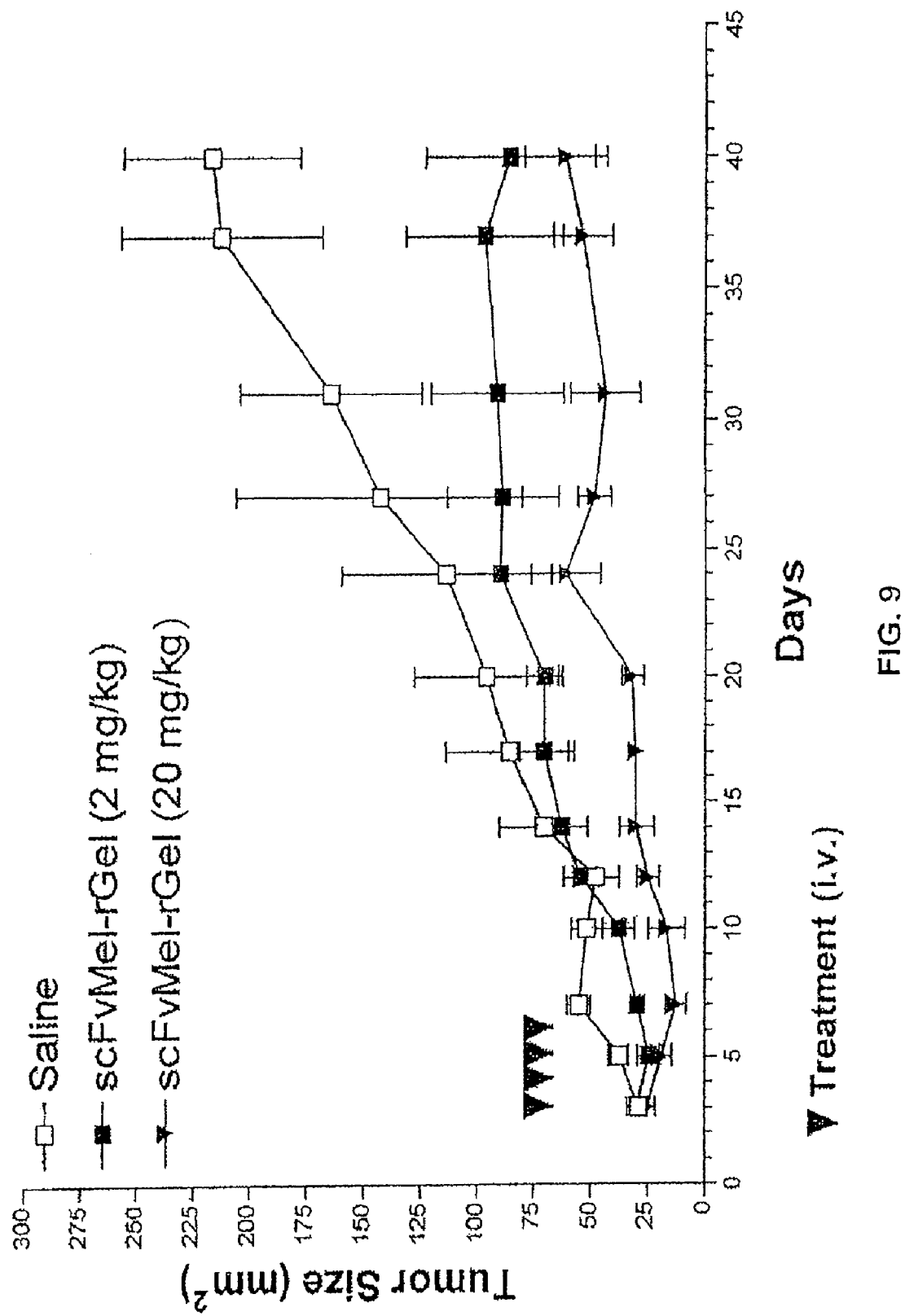
FIG. 9 Nude mice bearing well-developed melanoma tumors (A-375) growing in the right flank were treated (i.v.) with either saline (controls) or sfvMEL/rGel at 2 mg/kg or 20 mg/kg (total dose) for 4 consecutive days (arrows). Tumor areas were measured for 30 days. The saline-treated control tumors increased from 30 to 150 mm² over this period. Tumors treated with the lowest immunotoxin dose increased from 30 to 60 mm². Animals treated with the highest immunotoxin dose showed no overall increase in tumor size from the original 30 mm².

Mice bearing well-developed A-375 melanoma xenografts were treated with either saline (controls), or sfvMEL/rGel at either 2 or 20 mg/kg for 4 days. As shown in FIG. 9, tumor size in the control group increased from 30 to 150 mm$^2$ (500% increase) over the 28 day length of the experiment. In contrast, mice treated with the fusion toxin at 2 mg/kg showed a slight decrease in tumor size followed by an increase to approximately 60 mm$^2$ (100% increase). Mice treated with the 20 mg/kg dose of fusion toxin demonstrated a 50% decrease in tumor size during treatment followed by a slow recovery of tumor size back to the original tumor size over 28 days (no increase in overall growth). There were no obvious toxic effects of the immunotoxin on mice at these doses, suggesting that the maximal tolerated dose (MTD) at this schedule had not been reached.

Example 6

In Vitro Cytotoxicity Assay

Cell Culture Methods.

Human melanoma tumor cells A375M were maintained in culture using minimal essential medium (MEM) supplemented with 10% heat-inactivated fetal bovine serum plus 100 µM non-essential amino-acids, 2 mM L-glutamine, 1 mM sodium pyruvate, vitamins, and antibiotics. Cultured cells were screened routinely and found free of mycoplasma infection.

Cell Proliferation Assay

Cell lines were maintained in culture in complete medium at 37° C. in a 5% $CO_2$-humidified air incubator. For assays with recombinant toxins and immunotoxins, cultures were washed, cells were detached using versene, and resuspended in complete medium at a density of 25×10$^3$ cell/ml. Two hundred µl aliquots were dispensed into 96-well microtiter plates and the cells were then allowed to adhere. This results in a sparsely seeded population of cells. After 24 hours, the media was replaced with media containing different concentrations of either immunotoxins or gelonin. The cells were incubated for 72 hours and analyzed for relative cell proliferation by crystal violet staining.

Crystal Violet Staining

Cells were washed three times with PBS containing calcium and magnesium fixed and stained with 20% (v/v) methanol containing 0.5% (w/v) crystal violet. Bound dye was eluted with 150 µl of Sörensen's citrate buffer (0.1 M sodium citrate, pH 4.2-50% (v/v) ethanol) for 1 hour at room temperature. The absorbance was measured at 600 nm using a Bio-Tek microplate reader. Relative cell proliferation (RCP) was calculated as follows:

$$RCP = \frac{\text{Mean Absorbance (Drug Treated)}}{\text{Mean Absorbance (Non-drug Treated)}} \times 100\% \quad \text{[eq 1]}$$

Samples of purified scfvMEL-CFR2018, scfvMEL-CFR2025 and CFR2018 were assayed using a standard 72-h cell proliferation assay with log-phase (5,000/well) antigen-positive A375M cell monolayers and using crystal violet staining procedures as previously described.

Results

Figure 10:
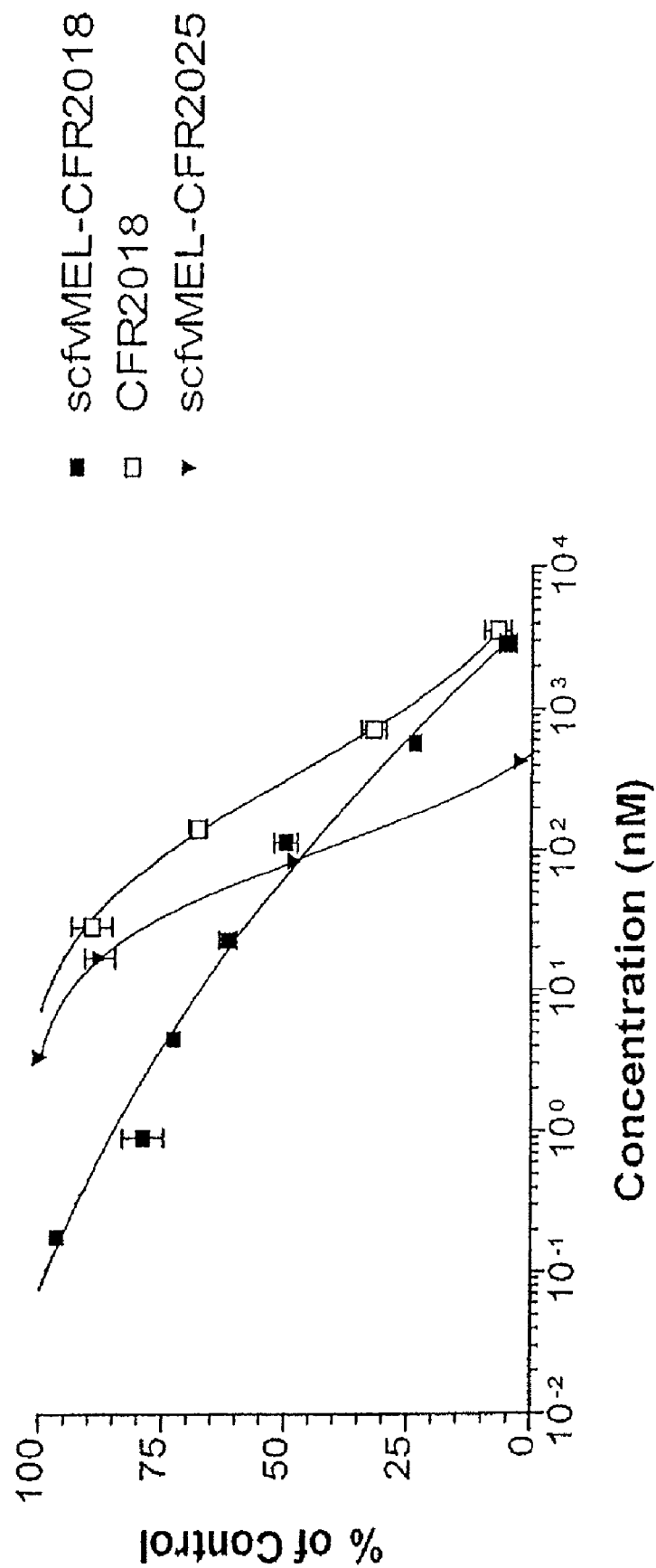
FIG. 10 The cytotoxicity of scfvMEL-CFR2018 (also known as "sfvMEL-CFR2018) was compared with the cytotoxicity of scfvMEL-CFR2025 on A375-M melanoma cells in an in vitro cytotoxicity assay.

FIG. 10 shows the cytotoxicity of each of the recombinant molecules tested on the 72 hr growth of the A-375 human melanoma cell line as described above. As shown, both scfvMEL-CFR2018 and scfvMEL-CFR2025 fusion constructs inhibited the growth of melanoma cells in culture. The concentration of each agent required to inhibit the growth of cells to 50% of control values (I.C.$_{50}$) was 100 nM. In contrast, cell growth inhibition by the free toxin (CFR2018) occurred at over 800 nM concentration or almost 8-fold higher compared to the antibody fusion constructs. Antibody targeting of the CFR2018 toxin to tumor cells by fusion to the scfvMEL antibody increases toxicity by 8-fold. In addition, in comparison to the CFR2018 toxin, the Designer Toxin designated CFR2025 has cytotoxic activity comparable to that of the CFR2018 toxin when they are both delivered to tumor cells with an antibody carrier.

All of the compositions and methods disclosed and claimed herein can be made and executed without undue experimentation in light of the present disclosure. While the compositions and methods of this invention have been described in terms of embodiments, it will be apparent to those of skill in the art that variations may be applied to the compositions and methods, and in the steps or in the sequence of steps of the methods, described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EPA No. 320 308
EPA No. 329 822
EPO 0273085
GB Application No. 2,202,328
GB Application No. 2193095
PCT/US85/01161
PCT/US87/00880
PCT/US 89/01025
PCT/US89/05040
U.S. Pat. No. 3,817,837
U.S. Pat. No. 3,850,752
U.S. Pat. No. 3,939,350
U.S. Pat. No. 3,996,345
U.S. Pat. No. 4,162,282
U.S. Pat. No. 4,196,265
U.S. Pat. No. 4,275,149
U.S. Pat. No. 4,277,437
U.S. Pat. No. 4,310,505
U.S. Pat. No. 4,366,241
U.S. Pat. No. 4,472,509
U.S. Pat. No. 4,472,509
U.S. Pat. No. 4,533,254
U.S. Pat. No. 4,554,101

U.S. Pat. No. 4,683,195
U.S. Pat. No. 4,683,202
U.S. Pat. No. 4,684,611
U.S. Pat. No. 4,690,915
U.S. Pat. No. 4,728,575
U.S. Pat. No. 4,728,578
U.S. Pat. No. 4,737,323
U.S. Pat. No. 4,800,159
U.S. Pat. No. 4,879,236
U.S. Pat. No. 4,883,750
U.S. Pat. No. 4,921,706
U.S. Pat. No. 4,938,948
U.S. Pat. No. 4,938,948
U.S. Pat. No. 4,946,773
U.S. Pat. No. 4,952,500
U.S. Pat. No. 5,021,236
U.S. Pat. No. 5,196,066
U.S. Pat. No. 5,199,942
U.S. Pat. No. 5,279,721
U.S. Pat. No. 5,302,523
U.S. Pat. No. 5,322,783
U.S. Pat. No. 5,359,046
U.S. Pat. No. 5,384,253
U.S. Pat. No. 5,401,511
U.S. Pat. No. 5,401,511
U.S. Pat. No. 5,432,260
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,603,872
U.S. Pat. No. 5,603,872
U.S. Pat. No. 5,610,042
U.S. Pat. No. 5,656,610
U.S. Pat. No. 5,693,762
U.S. Pat. No. 5,702,932
U.S. Pat. No. 5,736,524
U.S. Pat. No. 5,780,448
U.S. Pat. No. 5,786,214
U.S. Pat. No. 5,789,215
U.S. Pat. No. 5,801,005
U.S. Pat. No. 5,824,311
U.S. Pat. No. 5,830,880
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,849,718
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,155
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,871,727
U.S. Pat. No. 5,871,986
U.S. Pat. No. 5,879,703
U.S. Pat. No. 5,882,864
U.S. Pat. No. 5,889,155
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,277
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 6,020,192
U.S. Pat. No. 6,054,297
U.S. Pat. No. 6,099,842
U.S. Pat. No. 6,107,090
WO 88/10315
WO 89/00999
WO 89/06700
WO 90/07641
WO 94/09699
WO 95/06128
WO 98/0748
WO 99/18933
Abbondanzo et al., *Breast Cancer Res. Treat.*, 16:182(#151), 1990.
Adams et al., *Cancer Res* 1993; 53:4026-34, 1993.
Aksentijevich, et al., *Hum. Gene Ther.*, 7:1111-22, 1996.
Alfthan et al., *Protein Engineering* 1995; 8:725-31, 1995.

Allred et al., *Breast Cancer Res. Treat.*, 16:182(#149), 1990.
Almendro et al., *J Immunol*, 157:5411-5421, 1996.
Angel et al., *Cell*, 49:729, 1987b.
Angel et al., *Mol. Cell. Biol.*, 7:2256, 1987a.
Arap et al., *Cancer Res.*, 55:1351-1354, 1995.
Atchison and Perry, *Cell*, 46:253, 1986.
Atchison and Perry, *Cell*, 48:121, 1987.
Atherton et al., *Biol. of Reproduction*, 32:155-171, 1985.
Austin-Ward, Villaseca, *Rev. Med. Chil.*, 126(7):838-45, 1998.
Ausubel, ed., Current protocols in molecular biology, New York, John Wiley & Sons, 1996.
Baichwal and Sugden, In: *Gene Transfer*, Kucherlapati R, ed., New York, Plenum Press, pp. 117-148, 1986.
Bajorin et al, *Proc. Annu. Meet. Am. Soc. Clin. Oncol.*, 7:A967, 1988.
Baker, G. et al. (eds.), Modern Pharmaceutics, Marcel Dekker, Inc., New York, N.Y., 1990.
Bakhshi et al., *Cell*, 41(3):899-906, 1985.
Banerji et al., *Cell*, 27:299, 1981.
Banerji et al., *Cell*, 35:729, 1983.
Bangham, et al., *J. Mol. Biol.*, 13:238-252, 1965.
Bao et al., *Hum. Gene Ther.*, 7(3):355-65, 1996.
Barrio et al., *Hybridoma* 1998; 17:355-64, 1998.
Bass et al., *Cancer Gene Ther.*, 2(2):97-104, 1995.
Bedzyk et al., *J. Biol. Chem.*, 265:18615-20, 1990.
Bellus, *J. Macromol. Sci. Pure Appl. Chem.*, A31(1): 1355-1376, 1994.
Berberian et al., *Science*, 261:1588-1591, 1993.
Berkhout et al., *Cell*, 59:273, 1989.
Berkower I., *Current Opinion in Biotechnology* 1996; 7:622-28, 1996.
Bird et al., *Science* 1988; 242:423-26, 1988.
Blanar et al, *EMBO J*, 8:1139, 1989.
Bodine and Ley, *EMBO J*, 6:2997, 1987.
Bonavida et al., *Int J Oncol*, 15:793-802, 1999.
Bonavida et al., *Proc Nat'l Acad Sci USA.* 97:1754-9, 2000.
Boshart et al., *Cell*, 41:521, 1985.
Bosze et al., *EMBO J*, 5:1615, 1986.
Bourrie et al., *Eur. J. Biochem* 1986; 155:1-10, 1986.
Boyle et al., *Journal of Immunotherapy with Emphasis on Tumor Immunology* 1995; 18:221-30, 1995.
Braddock et al., *Cell*, 58:269, 1989.
Brown et al., *Breast Cancer Res. Treat.*, 16:192(#191), 1990.
Bukowski et al., *Clin. Cancer Res.*, 4(10):2337-47, 1998.
Bulla and Siddiqui, *J. Virol.*, 62:1437, 1986.
Burger et al., *Antimicrob. Agents Chemother.*, 37:1426-31, 1993.
Caldas et al., *Nat. Genet.*, 8:27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Canfield et al., *Methods in Enzymology*, 189, 418-422, 1990.
Capaldi et al., *Biochem. Biophys. Res. Comm.*, 76:425, 1977.
Carbonelli et al. *FEMS Microbiol Lett.* 177(1):75-82, 1999.
Celander and Haseltine, *J. Virology*, 61:269, 1987.
Celander et al., *J Virology*, 62:1314, 1988.
Chandler et al., *Cell*, 33:489, 1983.
Chandler et al., *Proc Natl Acad Sci USA.* 94(8):3596-3601, 1997.
Chang et al., *Mol. Cell. Biol.*, 9:2153, 1989.
Chatterjee et al, *Proc. Nat'l Acad. Sci. USA.*, 86:9114, 1989.
Chaudhary et al., *Proc. Natl. Acad. Sci. USA.*, 87:9491-4, 1990.
Chen and Okayama, *Mol. Cell. Biol.*, 7:2745-2752, 1987.
Cheng et al., *Cancer Res.*, 54:5547-5551, 1994.
Cheng, et al., *Investigative Radiology*, vol. 22, pp. 47-55, 1987.
Cheresh et al., *Cancer Res.*, 46:5112-8, 1986.
Choi et al., *Cell*, 53:519, 1988.
Christodoulides et al., *Microbiology*, 144(Pt 11):3027-37, 1998.
Cleary and Sklar, *Proc. Nat'l. Acad. Sci. USA*, 82(21):7439-43, 1985.
Cleary et al., *J. Exp. Med.*, 164(1):315-20, 1986.
Cleary et al., *Trends Microbiol.*, 4:131-136, 1994.
Cocea, *Biotechniques.* 23(5):814-816, 1997.
Cohen et al, *J. Cell. Physiol*, 5:75, 1987.
Costa et al, *Mol. Cell. Biol.*, 8:81, 1988.
Coupar et al., *Gene*, 68:1-10, 1988.
Cripe et al., *EMBO J*, 6:3745, 1987.
Culotta and Hamer, *Mol. Cell. Biol.*, 9:1376, 1989.
Culver et al., *Science*, 256:1550-1552, 1992.
Dandolo et al., *J. Virology*, 47:55, 1983.
Davidson et al., *J. Immunother.*, 21(5):389-98, 1998.
De Villiers et al., *Nature*, 312:242, 1984.
Deamer and P. Uster, Liposomes (M. Ostro, ed.), Marcel Dekker, Inc., New York, pp. 27-52, 1983.
Dejager et al., *J. Clin. Invest.*, 92:894-902, 1993.
Deschamps et al., *Science*, 230:1174, 1985.
Dholakia et al., *J. Biol. Chem.*, 264, 20638-20642, 1989.
Dillman *Cancer Biother. Radiopharm.*, 14:5-10, 1999.
Dong et al, *Hum. Gene Ther.*, 7(3):319-31, 1996.
Doolittle et al., *Methods Mol. Biol.*, 109:215-37, 1999.
Edbrooke et al., *Mol. Cell. Biol.*, 9:1908, 1989.
Edlund et al., *Science*, 230:912, 1985.
El-Gorab et al, *Biochem. Biophys. Acta*, 1973, 306, 58-66, 1973.
Fechheimer et al., *Proc. Nat'l Acad. Sci. USA*, 84:8463-8467, 1987.
Felgner et al, *Proc. Nat'l. Acad. Sci. USA*, 84:7413-7, 1987.
Fendler et al., Catalysis in Micellar and Macromolecular Systems, Academic Press, New York, 1975.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Foecking and Hofstetter, *Gene*, 45(1):101-5, 1986.
Fraley et al., *Proc. Nat'l Acad. Sci. USA*, 76:3348-3352, 1979.
Friedmann, *Science*, 244:1275-1281, 1989.
Frohman, In: *PCR Protocols: A Guide To Methods And Applications*, Academic Press, N.Y., 1990.
Fujita et al., *Cell*, 49:357, 1987.
Fulton et al., *Cancer Res* 1988; 48:2618-25, 1988.
Gabizon et al., *Cancer Res.*, 50(19):6371-8, 1990.
Geiser et al., *Cancer Res* 1999; 59:905-10, 1999.
Ghosh and Bachhawat, In: *Liver diseases, targeted diagnosis and therapy using specific receptors and ligands*, (Wu G, Wu C ed.), New York: Marcel Dekker, pp. 87-104, 1991.
Gilles et al., *Cell*, 33:717, 1983.
Gilliland et al., *Proc. Nat'l. Acad. Sci. USA*, 77:4539-43, 1980.
Gliniak et al., *Cancer Res.* 59:6153-8, 1999.
Gloss et al., *EMBO J*, 6:3735, 1987.
Godbout et al., *Mol. Cell. Biol.*, 8:1169, 1988.
Goodbourn and Maniatis, *Proc. Nat'l Acad. Sci. USA*, 85:1447, 1988.
Goodbourn et al., *Cell*, 45:601, 1986.
Gopal, *Mol Cell Biol.*, 5:1188-1190, 1985.
Graham and Van Der Eb, *Virology*, 52:456-467, 1973.
Greene et al., *Immunology Today*, 10:272, 1989.
Gregoriadis, ed., Drug Carriers In Biology And Medicine, pp. 287-341, 1979.

Gregoriadis, G., ed., Liposome Technology, vol. I, pp. 30-35, 51-65 and 79-107 (CRC Press Inc., Boca Raton, Fla., 1984.
Grosschedl and Baltimore, *Cell,* 41:885, 1985.
Gulbis et al., *Hum. Pathol.,* 24:1271-85, 1993.
Hanibuchi et al., *Int. J. Cancer,* 78(4):480-5, 1998.
Hara et al, *Biochim. Biophys. Acta,* 1278:51-8, 1996.
Harland and Weintraub, *J. Cell Biol.,* 101:1094-1099, 1985.
Harlow and Lane, "Antibodies: A Laboratory Manual," Cold Spring Harbor Laboratory, 1988.
Haslinger and Karin, *Proc. Nat'l Acad. Sci. USA.,* 82:8572, 1985.
Hauber and Cullen, *J. Virology,* 62:673, 1988.
Heath et al., *Chem. Phys. Lipids,* 40:347, 1986.
Hechushtan, et al., *EMBO Jour.,* 18: 2330-2341, 1999.
Hellstrand et al., *Acta. Oncol.,* 37(4):347-53, 1998.
Hen et al., *Nature,* 321:249, 1986.
Hensel et al., *Lymphokine Res.,* 8:347, 1989.
Hermonat and Muzyczka, *Proc. Nat'l. Acad. Sci. USA,* 81:6466-6470, 1984.
Herr and Clarke, *Cell,* 45:461, 1986.
Hirochika et al., *J. Virol.,* 61:2599, 1987.
Hirsch et al., *Mol. Cell. Biol.,* 10: 1959, 1990.
Holbrook et al., *Virology,* 157:211, 1987.
Hollstein et al., *Science* 253:49-53, 1991.
Hope et al., *Biochimica et Biophysica Acta,* 812: 55-65, 1985.
Horlick and Benfield, *Mol. Cell. Biol.,* 9:2396, 1989.
Horwich et al. *J. Virol.,* 64:642-650, 1990.
Huang et al., *Cell,* 27:245, 1981.
Hug et al., *Mol Cell Biol.,* 8:3065, 1988.
Hui and Hashimoto, *Infect. Immun.,* 66(11):5329-36, 1998.
Hussussian et al., *Nature Genetics,* 15-21, 1994.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc Natl Acad Sci USA.* 85(24):9436-9440, 1988.
Inouye et al., *Nucleic Acids Res.,* 13:3101-3109, 1985.
Irie & Morton, *Proc. Nat'l Acad. Sci. USA* 83:8694-8698, 1986
Irie et al., "Melanoma gangliosides and human monoclonal antibody," In: *Human Tumor Antigens and Specific Tumor Therapy,* Metzgar & Mitchell (eds.), Alan R. Liss, Inc., New York, pp. 115-126, 1989.
Jakobovits et al., *Mol. Cell. Biol.,* 8:2555, 1988.
Jameel and Siddiqui, *Mol. Cell. Biol.,* 6:710, 1986.
Jaynes et al, *Mol. Cell. Biol.,* 8:62, 1988.
Johnson et al., *J. Virol.,* 67:438-445, 1993.
Johnson et al., *Mol. Cell. Biol.,* 9:3393, 1989.
Kadesch and Berg, *Mol. Cell. Biol.,* 6:2593, 1986.
Kaeppler et al., *Plant Cell Reports* 9: 415-418, 1990.
Kamb et al., *Nature Genetics,* 8:22-26, 1994.
Kamb et al., *Science,* 2674:436-440, 1994.
Kaneda et al., *Science,* 243:375-378, 1989.
Kang et al., *Science,* 240:1034-1036, 1988.
Kantor et al., *Hybridoma* 1982; 1:473-82, 1982.
Karin et al., *Mol. Cell. Biol.,* 7:606, 1987.
Katinka et al., *Cell,* 20:393, 1980.
Katinka et al., *Nature,* 290:720, 1981.
Kato et al, *J. Biol. Chem.,* 266:3361-3364, 1991.
Kawamoto et al., *Mol. Cell. Biol.,* 8:267, 1988.
Keane et al., *Cancer Res.* 59:734-41, 1999.
Kerr et al., *Br. J. Cancer,* 26(4):239-57, 1972.
Khatoon et al., *Ann. of Neurology,* 26, 210-219, 1989.
Kiledjian et al., *Mol. Cell. Biol.,* 8:145, 1988.
Kim et al., *Gene* 1988; 68:315-21.
King et al., *J. Biol. Chem.,* 269, 10210-10218, 1989.
Kipriyanov et al., *Molecular Immunology* 1994; 31:1047-58, 1994.
Klamut et al., *Mol. Cell. Biol.,* 10:193, 1990.
Koch et al., *Mol. Cell. Biol.,* 9:303, 1989.
Kohler et al, *Clin. Immunol. Immunopathol.,* 52:104-16, 1989.
Koizumi et al., *Japanese J of Cancer Res* 1988; 79:973-81, 1988.
Kraus et al. *FEBS Lett.,* 428(3):165-170, 1998.
Kreier et al., "Infection, Resistance and Immunity," Harper and Row, New York, 1991.
Kriegler and Botchan, In: *Eukaryotic Viral Vectors,* Y. Gluzman, ed., Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984a.
Kriegler et al., *Cell,* 53:45, 1988.
Kriegler et al., In: *Cancer Cells 2/Oncogenes and Viral Genes,* Van de Woude et al. eds, Cold Spring Harbor, Cold Spring Harbor Laboratory, 1984b.
Kriegler et al., In: *Gene Expression,* D. Hamer and M. Rosenberg, eds., New York: Alan R. Liss, 1983.
Kuhl et al., *Cell,* 50:1057, 1987.
Kunz et al., *Nucl. Acids Res.,* 17:1121, 1989.
Kurucz et al., *Proc Natl Acad Sci USA* 1993; 90: 3830-34, 1993.
Kwoh et al., *Proc. Nat. Acad. Sci. USA,* 86: 1173, 1989.
Kyte and Doolitle, *J. Mol. Biol.,* 157(1):105-132, 1982.
Lareyre et al., *J Biol. Chem.,* 274(12):8282-8290, 1999.
Larsen et al., *Proc. Nat'l Acad. Sci. USA.,* 83:8283, 1986.
Laspia et al., *Cell,* 59:283, 1989.
Latimer et al., *Mol. Cell. Biol.,* 10:760, 1990.
Lee et al., *J Auton Nerv Syst.* 74(2-3):86-90, 1997.
Lee et al., *Nature,* 294:228, 1981.
Lee et al., *Nucleic Acids Res.,* 12:4191-206, 1984.
Lefranc et al., *Biochimie* 1990; 72:639-51, 1990.
Lenert et al., *Science,* 248:1639-1643, 1990.
Levenson et al., *Hum Gene Ther.* 20; 9(8):1233-1236, 1998.
Levinson et al., *Nature,* 295:79, 1982.
Lin et al., *Mol. Cell. Biol.,* 10:850, 1990.
Liu et al., *J. Biol. Chem.,* 270:24864-70, 1995.
Luria et al, *EMBO J.,* 6:3307, 1987.
Lusky and Botchan, *Proc. Nat'l Acad. Sci. USA.,* 83:3609, 1986.
Lusky et al., *Mol. Cell. Biol.,* 3:1108, 1983.
Macejak and Sarnow, *Nature,* 353:90-94, 1991.
Macey et al, *Am J of Physiologic Imaging* 1988; 3:1-6, 1988.
Majors and Varmus, *Proc. Nat'l Acad. Sci. USA.,* 80:5866, 1983.
Marsters et al., *Recent Prog Horm Res* 54:225-34, 1999.
Martin et al, *Nature,* 345(6277):739-743, 1990.
Mayer et al., *Biochimica et Biophysica Acta, vol.* 858, pp. 161-168, 1986.
Mayhew et al., *Biochimica et Biophysica Acta,* vol. 775, pp. 169-174, 1984.
Mayhew et al., *Methods in Enzymology,* vol. 149, pp. 64-77, 1987.
McCartney et al., *Protein Engineering* 1995; 8:301-14, 1995.
McNeall et al., *Gene,* 76:81, 1989.
Miksicek et al., *Cell,* 46:203, 1986.
Mitchell et al., *Ann. N.Y. Acad. Sci.,* 690:153-166, 1993.
Mitchell et al., *J. Clin. Oncol.* 8(5):856-859, 1990.
Mittelman et al., *Clin Cancer Res* 1995; 1:705-13, 1995.
Montaldo, et al., *Int. J. Cancer,* 81:262-7, 1999.
Mordacq and Linzer, *Genes and Dev.,* 3:760, 1989.
Moreau et al., *Nucl. Acids Res.,* 9:6047, 1981.

Morgan et al., *Hybridoma* 1981; 1:27-36, 1981.
Mori et al., *Cancer Res.*, 54:3396-3397, 1994.
Morton and Ravindranath, M. H. Current concepts concerning melanoma vaccines. In *Tumor Immunology*, Dalgleish A G (ed.), London: Cambridge University Press, 1-55, 1996.
Morton et al., *Ann. Surg.* 216: 463-482, 1992.
Muesing et al., *Cell*, 48:691, 1987.
Mujoo et al., *Cancer Immunology, Immunotherapy* 1995; 40:339-45, 1995.
Munishkin et al., *J. Biol. Chem.*, 270:30581-30587, 1995.
Nakamura et al., In: *Enzyme Immunoassays: Heterogeneous and Homogeneous Systems*, Chapter 27, 1987.
Ng et al, *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, pp. 493-513, 1988.
Nicolau and Sene, *Biochim. Biophys. Acta*, 721:185-190, 1982.
Nicolau et al., *Methods Enzymol.*, 149:157-176, 1987.
Nishikawa et al., *Cancer Res* 1992; 52:4758-65, 1992.
Nobri et al., *Nature*, 368:753-756, 1995.
Nomoto et al., *Gene*, 236(2):259-271, 1999.
Ohara et al., *Proc. Nat'l Acad. Sci. USA*, 86: 5673-5677, 1989.
O'Hare et al., *FEBS Lett* 1990; 273:200-04, 1990.
Okamoto et al., *Proc. Nat'l Acad. Sci. USA*, 91:11045-11049, 1994.
Omirulleh et al., *Plant Mol. Biol.*, 21:415-28, 1993.
Ondek et al., *EMBO J.*, 6:1017, 1987.
Orlow et al., *Cancer Res.*, 54:2848-2851, 1994.
Ornitz et al., *Mol. Cell. Biol.*, 7:3466, 1987.
O'Shannessy et al., *J. Immun. Meth.*, 99, 153-161, 1987.
Owens and Haley, *J. Biol. Chem.*, 259:14843-14848, 1987.
Owens et al., *Journal of Immunological Methods* 1994; 168: 149-165, 1994.
Pagnan et al., *Int. J. Cancer*, 81:268-74, 1999.
Palmiter et al., *Nature*, 300:611, 1982.
Panchagnula et al., *Journal of Clinical Pharmacy & Therapeutics* 1997; 22:7-19, 1997.
Panchal R G., *Biochemical Pharmacology* 1998; 55:247-252, 1998.
Pech et al., *Mol. Cell. Biol.*, 9:396, 1989.
Pelletier and Sonenberg, *Nature*, 334:320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Philip et al., *J. Biol. Chem.*, 268:16087-90, 1993.
Picard and Schaffner, *Nature*, 307:83, 1984.
Pietras et al., *Oncogene*, 17(17):2235-49, 1998.
Pinkert et al., *Genes and Dev.*, 1:268, 1987.
Pirker et al., *J Immunol* 1993; 150:3054-61, 1993.
Poe, et al., *J. Biol. Chem.*, 266: 98-103, 1991.
Ponta et al., *Proc. Nat'l Acad. Sci. USA.*, 82:1020, 1985.
Porton et al., *Mol. Cell. Biol.*, 10:1076, 1990.
Potrykus et al., *Mol. Gen. Genet.*, 199:183-188, 1985.
Potter and Haley, *Meth. in Enzymol.*, 91, 613-633, 1983.
Press et al., *Cellular Immunology* 1986; 102:10-20, 1986.
Pullyblank et al., *British Journal of Surgery* 1997; 84:1511-17, 1997.
Qin et al., *Proc. Nat'l Acad. Sci. USA*, 95(24):1411-6, 1998.
Queen and Baltimore, *Cell*, 35:741, 1983.
Quinn et al., *Mol. Cell. Biol.*, 9:4713, 1989.
Ravindranath and Morton, *Intern. Rev. Immunol.* 7: 303-329, 1991.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Resendez Jr. et al., *Mol. Cell. Biol.*, 8:4579, 1988.
Ridgeway, In: *Vectors: A survey of molecular cloning vectors and their uses*, Rodriguez R L, Denhardt D T, ed., Stoneham:Butterworth, pp. 467-492, 1988.
Ripe et al., *Mol. Cell. Biol.*, 9:2224, 1989.
Rippe et al., *Mol. Cell. Biol.*, 10:689-695, 1990.
Rittling et al., *Nucl. Acids Res.*, 17:1619, 1989.
Roselli et al., *In Vivo* 1993; 7:615-21, 1993.
Rosen et al., *Cell*, 41:813, 1988.
Rosenberg et al., *Ann. Surg.*, 210:474, 1989.
Rosenberg et al., *N. Engl. J. Med.*, 319:1676, 1988.
Rosenblum et al., *Cancer Chemotherapy and Pharmacology* 1999; 44:343-48, 1999.
Rosenblum et al., *Clin Cancer Res* 1999; 5:865-74, 1999.
Rosenblum et al., *Journal of Interferon & Cytokine Research* 1995; 15: 547-55, 1995.
Rosenblum et al, *Molecular Biotherapy* 1991; 3:6-13, 1991.
Rowlinson-Busza et al., *Current Opinion in Oncology* 1992; 4:1142-48, 1992.
Sakai et al., *Genes and Dev.*, 2:1144, 1988.
Sambrook et al., In: *Molecular Cloning: A Laboratory Manual*, 2nd Ed., Cold Spring Harbor Press, Cold Spring Harbor, N.Y., 1989.
Sambrook J, Fritsch E F, Maniatis T. Molecular Cloning A Laboratory Manual, 2$^{nd}$ Edition, Cold Spring Harbor Laboratory Press 1989.
Sandhu et al., *Crit. Rev Biotechnol* 1992; 12:437-62, 1992.
Sasso et al, *J. Immunol.*, 142:2778-2783, 1989.
Satake et al., *J. Virology*, 62:970, 1988.
Schaffner et al., *J. Mol. Biol.*, 201:81, 1988.
Schulz et al, *Cancer Res.* 44:5914-5920, 1984.
Searle et al, *Mol. Cell. Biol.*, 5:1480, 1985.
Serrano et al, *Nature*, 366:704-707, 1993.
Serrano et al., *Science*, 267:249-252, 1995.
Sharp and Marciniak, *Cell*, 59:229, 1989.
Shaul and Ben-Levy, *EMBO J*, 6:1913, 1987.
Sherman et al., *Mol. Cell. Biol.*, 9:50, 1989.
Shinoda, K. et al., Colloidal Surfactant, Academic Press, especially "The Formation of Micelles", Ch. 1, 1-96, 1963.
Shorki et al., *J. Immunol.*, 146:936-940, 1991.
Silvermann et al., *J. Clin. Invest.*, 96:417-426, 1995.
Sleigh and Lockett, *J. EMBO*, 4:3831, 1985.
Solodin et al., *Biochemistry*, 34:13537-44, 1995.
Spalholz et al., *Cell*, 42:183, 1985.
Spandau and Lee, *J. Virology*, 62:427, 1988.
Spandidos and Wilkie, *EMBO J.*, 2:1193, 1983.
Spanjer and Scherphof, *Biochim. Biophys. Acta*, 734:40-7, 1983.
Sperti et al., *Ital. J. Biochem.*, 35:266-71, 1986.
Stephens and Hentschel, *Biochem. J*, 248:1, 1987.
Stirpe et al., *A Journal of Biological Chemistry* 1992; 255: 6947-53, 1992.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Szoka et al., *Proc. Natl. Acad. Sci.*, 1978, 75:4194-4198.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (ed.), New York: Plenum Press, pp. 149-188, 1986.

Templeton et al., *Nat. Biotechnol.*, 15(7):647-52, 1997.
Thierry et al., *Proc. Nat'l. Acad. Sci., USA*, 92:9742-6, 1995.
Thiesen et al., *J. Virology*, 62:614, 1988.
Treisman, *Cell*, 46:567-74, 1986.
Trimble and Hozumi, *FEBS Lett.*, 219:70-4, 1987.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsujimoto and Croce, *Proc. Natl. Acad. Sci. USA*, 83(14): 5214-8, 1986.
Tsujimoto et al., *Science*, 228(4706):1440-3, 1985.
Tsukamoto et al., *Nat. Genet.*, 9:243-8, 1995.
Tsumaki et al., *J Biol. Chem.* 273(36):22861-22864, 1998.
Tyndall et al., *Nuc. Acids. Res.*, 9:6231, 1981.
Vannice and Levinson, *J. Virology*, 62:1305, 1988.
Vasseur et al., *Proc. Nat'l Acad. Sci. USA.*, 77:1068, 1980.
Wagner et al., *Science*, 260:1510-1513, 1990.
Wahl et al., *Cancer* 1994; 73:989-92, 1994.
Walker et al., *Proc. Nat'l Acad. Sci. USA*, 89:392-396 1992.
Wang and Calame, *Cell*, 47:241, 1986.
Watt et al., *Proc. Natl. Acad. Sci.*, 83(2): 3166-3170, 1986.
Weber et al., *Cell*, 36:983, 1984.
Weinberg, *Science*, 254:1138-1145, 1991.
Weinberger et al. *Mol. Cell. Biol.*, 8:988, 1984.
Wels et al., *Journal of Steroid Biochemistry & Molecular Biology* 1992; 43:1-7, 1992.
Williams et al., *Cancer Res* 1990; 50:974s-79s, 1990.
Wilson et al., *Int J Cancer* 1981; 28:293-30, 1981.
Winoto and Baltimore, *Cell*, 59:649, 1989.
Wolff et al., *Ther Immunol* 1995; 2:137-45, 1995.
Wong et al., *Gene*, 10:87-94, 1980.
Wool et al., *Biochem Cell Biol.*, 73(11-12):933-47, 1995
Worn et al., *Biochemistry* 1998; 22:13120-127, 1998.
Wu and Wu, *Adv. Drug Delivery Rev.*, 12:159-167, 1993.
Wu and Wu, *J. Biol. Chem.*, 262:4429-4432, 1987.
Wu et al., *Biochem. Biophys. Res. Commun.*, 233(1):221-6, 1997.
Xu et al., *Leukemia* 1996; 10:321-26, 1996.
Yang and Huang, *Gene Therapy*, 4 (9):950-960, 1997.
Yutzey et al. *Mol. Cell. Biol.*, 9:1397, 1989.
Zhao-Emonet et al., *Biochem. Biophys. Acta.*, 1442(2-3):109-19, 1998.
Zhu et al., *Science*, 261:209-11, 1993.

---

What is claimed is:

1. A method of killing a cancer cell comprising providing to the cell an effective amount of an immunotoxin comprising a recombinant getonin toxin and single chain antibody that specifically targets the cancer cell, wherein the recombinant gelonin toxin is modified relative to full-length, wild-type gelonin through the removal of one or more sequence regions that are antigenic in humans.

2. The method of claim 1, wherein the antibody targets a tumor antigen.

3. The method of claim 1, wherein the antibody is a mouse antibody.

4. The method of claim 1, wherein the cancer cell is a melanoma cell.

5. The method of claim 4, wherein the immunotoxin is scfvMEL-2025.

6. A method of treating cancer in a patient comprising administering to the patient an effective amount of a composition comprising an immunotoxin comprising a recombinant gelonin toxin and single chain antibody that specifically targets a cancer cell, wherein the recombinant gelonin toxin is modified relative to full-length, wild-type gelonin through the removal of one or more sequence regions that are antigenic in humans.

7. The method of claim 6, wherein the cancer is cancer of the prostate, lung, brain, skin, liver, breast, lymphoid, stomach, testicular, ovarian, pancreatic, bone, bone marrow, head and neck, cervical, esophagus, eye, gall bladder, kidney, adrenal glands, heart, colon, or blood.

8. The method of claim 6, wherein the antibody targets a melanoma cell.

9. The method of claim 8, wherein the immunotoxin is scfvMEL-2025.

10. The method of claim 6, wherein the composition comprises an scFvMEL/rGel recombinant toxin fusion construct.

11. A method for treating cancer in a patient comprising administering to the patient an effective amount of a composition comprising a ligand that selectively targets cells of the patient's cancer, wherein the ligand is conjugated or fused to a recombinant gelonin toxin, wherein the recombinant gelonin toxin is modified relative to full-length, wild-type gelonin through the removal of one or more sequence regions that are antigenic in humans.

12. The method of claim 11, wherein the targeting ligand is an antibody.

13. The method of claim 12, wherein the antibody is human or humanized.

14. The method of claim 12, wherein the antibody is a single chain antibody.

15. The method of claim 12, wherein the antibody binds to an antigen on the cancer cell.

16. The method of claim 15, wherein the cancer cell is a bone, brain, breast, cervical, colon, glioma, gum, head and neck, kidney, leukemia, liver, lung, melanoma, ovarian, prostate stomach, or tongue cell.

17. The method of claim 16, wherein the cancer cell is a melanoma cell.

18. The method of claim 12, wherein the antibody is 9.2.27 or ZME-018.

19. The method of claim 11, further comprising administering to the patient chemotherapy, radiotherapy, or a second immunotherapy.

20. The method of claim 11, further comprising resecting a pre-cancerous or cancerous lesion or tumor from the patient.

21. The method of claim 11, wherein the ligand is a cytokine or growth factor.

22. The method of claim 21, wherein the ligand is a VEGF.

23. A method of treating cancer in a patient comprising administering to the patient an effective amount of a composition comprising an immunotoxin comprising a recombinant gelonin toxin and single chain antibody that specifically targets a cancer cell, wherein the immunotoxin is scfvMEL-2018 having the sequence of SEQ ID NO: 11.

24. A method of killing a cancer cell comprising providing to the cell an effective amount of an immunotoxin comprising a recombinant getonin toxin and single chain antibody that specifically targets the cancer cell, wherein the recombinant gelonin toxin is modified relative to full-length, wild-type gelonin through the replacement of one or more sequence regions that are antigenic in humans with an amino acid sequence that is less antigenic in humans.

25. The method of claim 24, wherein the antibody targets a tumor antigen.

26. The method of claim 24, wherein the antibody is a mouse antibody.

27. The method of claim 24, wherein the cancer cell is a melanoma cell.

28. The method of claim 27, wherein the immunotoxin is scfvMEL-2025.

29. A method of treating cancer in a patient comprising administering to the patient an effective amount of a composition comprising an immunotoxin comprising a recombinant gelonin toxin and single chain antibody that specifically targets a cancer cell, wherein the recombinant gelonin toxin is modified relative to full-length, wild-type gelonin through the replacement of one or more sequence regions that are antigenic in humans with an amino acid sequence that is less antigenic in humans.

30. The method of claim 29, wherein the cancer is cancer of the prostate, lung, brain, skin, liver, breast, lymphoid, stomach, testicular, ovarian, pancreatic, bone, bone marrow, head and neck, cervical, esophagus, eye, gall bladder, kidney, adrenal glands, heart, colon, or blood.

31. The method of claim 29, wherein the antibody targets a melanoma cell.

32. The method of claim 31, wherein the immunotoxin is scfvMEL-2025.

33. A method for treating cancer in a patient comprising administering to the patient an effective amount of a composition comprising a ligand that selectively targets cells of the patient's cancer, wherein the ligand is conjugated or fused to a recombinant gelonin toxin, wherein the recombinant gelonin toxin is modified relative to full-length, wild-type gelonin through the replacement of one or more sequence regions that are antigenic in humans with an amino acid sequence that is less antigenic in humans.

34. The method of claim 33, wherein the targeting ligand is an antibody.

35. The method of claim 34, wherein the antibody is human or humanized.

36. The method of claim 34, wherein the antibody is a single chain antibody.

37. The method of claim 34, wherein the antibody binds to an antigen on the cancer cell.

38. The method of claim 37, wherein the cancer cell is a bone, brain, breast, cervical, colon, glioma, gum, head and neck, kidney, leukemia, liver, lung, melanoma, ovarian, prostate stomach, or tongue cell.

39. The method of claim 38, wherein the cancer cell is a melanoma cell.

40. The method of claim 34, wherein the antibody is 9.2.27 or ZME-018.

41. The method of claim 33, further comprising administering to the patient chemotherapy, radiotherapy, or a second immunotherapy.

42. The method of claim 33, further comprising resecting a pre-cancerous or cancerous lesion or tumor from the patient.

43. The method of claim 33 wherein the ligand is a cytokine or growth factor.

44. The method of claim 43, wherein the ligand is a VEGF.

* * * * *

UNITED STATES PATENT AND TRADEMARK OFFICE
CERTIFICATE OF CORRECTION

PATENT NO. : 7,741,278 B2
APPLICATION NO. : 11/856606
DATED : June 22, 2010
INVENTOR(S) : Michael G. Rosenblum et al.

It is certified that error appears in the above-identified patent and that said Letters Patent is hereby corrected as shown below:

In claim 1, column 111, line 4, delete "getonin" and insert --gelonin-- therefor.

In claim 24, column 112, line 9, delete "getonin" and insert --gelonin-- therefor.

Signed and Sealed this

Seventh Day of September, 2010

David J. Kappos
*Director of the United States Patent and Trademark Office*